United States Patent
Mortier et al.

(10) Patent No.: US 6,746,471 B2
(45) Date of Patent: Jun. 8, 2004

(54) TRANSVENTRICULAR IMPLANT TOOLS AND DEVICES

(75) Inventors: Todd J. Mortier, Minneapolis, MN (US); Cyril J. Schweich, Jr., St. Paul, MN (US); Robert M. Vidlund, Maplewood, MN (US); Peter T. Keith, St. Paul, MN (US); Thomas M. Paulson, Minneapolis, MN (US); David A. Kusz, Minneapolis, MN (US)

(73) Assignee: Myocor, Inc., St. Paul, MN (US)

( * ) Notice: Subject to any disclaimer, the term of this patent is extended or adjusted under 35 U.S.C. 154(b) by 306 days.

(21) Appl. No.: 09/864,320

(22) Filed: May 25, 2001

(65) Prior Publication Data

US 2001/0025171 A1 Sep. 27, 2001

Related U.S. Application Data

(63) Continuation of application No. 09/123,977, filed on Jul. 29, 1998, now Pat. No. 6,260,552.

(51) Int. Cl.⁷ .............................................. A61B 17/28
(52) U.S. Cl. ........................ 606/207; 606/206; 600/201
(58) Field of Search ................................ 606/205–207, 606/210, 211, 174; 600/210, 211, 16, 37, 201, 231

(56) References Cited

U.S. PATENT DOCUMENTS

| | | | |
|---|---|---|---|
| 3,019,790 A | * | 2/1962 | Militana ..................... 606/205 |
| 3,980,086 A | * | 9/1976 | Kletschka et al. .......... 606/174 |
| 4,192,293 A | | 3/1980 | Asrican |
| 4,261,342 A | | 4/1981 | Aranguren Duo |
| 4,300,564 A | * | 11/1981 | Furihata ..................... 606/207 |
| 4,372,293 A | | 2/1983 | Vijil-Rosales |
| 4,409,974 A | | 10/1983 | Freedland |
| 4,536,893 A | | 8/1985 | Parravicini |
| 4,690,134 A | | 9/1987 | Snyders |
| 4,936,857 A | | 6/1990 | Kulik |

(List continued on next page.)

FOREIGN PATENT DOCUMENTS

| | | |
|---|---|---|
| DE | 296 19 294 | 8/1987 |
| DE | 36 14 292 | 11/1987 |
| DE | 42 34 127 | 5/1994 |
| DE | 199 47 885 A1 | 4/2000 |
| DE | 298 24 917 U1 | 6/2000 |

(List continued on next page.)

OTHER PUBLICATIONS

US 6,197,052, 3/2001, Cosgrove et al. (withdrawn)
Kay et al., "Surgical Treatment of Mitral Insufficiency," *The Journal of Thoracic Surgery*, 29: 618–620, 1995.
Harken et al., "The Surgical Correction of Mitral Insufficiency," *The Journal of Thoracic Surgery*, 28:604–627, 1954.
Bailey et al., "Closed Intracardiac Tactile Surgery," *Diseases of the Chest*, XXII:1–24, Jul. 1952.

(List continued on next page.)

*Primary Examiner*—Julian W. Woo
(74) *Attorney, Agent, or Firm*—Finnegan, Henderson, Farabow, Garrett & Dunner, LLP

(57) ABSTRACT

A method and implantation tools for placing a transventricular splint including a tension member. The method includes gaining access to the patient's hearts and identifying entry or exit points for the tension member, marking those locations and delivering the tension member. Anchors for the tension member are also delivered. The length of the tensions member is measured and the walls of the heart drawn together. The pads are secured to the tension member and the tension member is trimmed to length. The pads are secured to the heart surface.

22 Claims, 31 Drawing Sheets

U.S. PATENT DOCUMENTS

| | | | |
|---|---|---|---|
| 4,944,753 A | 7/1990 | Burgess et al. | |
| 4,960,424 A | 10/1990 | Grooters | |
| 4,997,431 A | 3/1991 | Isner et al. | |
| 5,104,407 A | 4/1992 | Lam et al. | |
| 5,106,386 A | 4/1992 | Isner et al. | |
| 5,131,905 A | 7/1992 | Grooters | |
| RE34,021 E | 8/1992 | Mueller et al. | |
| 5,169,381 A | 12/1992 | Snyders | |
| 5,192,314 A | 3/1993 | Daskalakis | |
| 5,250,049 A | 10/1993 | Michael | |
| 5,284,488 A | 2/1994 | Sideris | |
| 5,300,087 A * | 4/1994 | Knoepfler | 606/207 |
| 5,360,444 A | 11/1994 | Kusuhara | |
| 5,385,528 A | 1/1995 | Wilk | |
| 5,417,709 A * | 5/1995 | Slater | 606/205 |
| 5,433,727 A | 7/1995 | Sideris | |
| 5,450,860 A | 9/1995 | O'Connor | |
| 5,452,733 A | 9/1995 | Sterman et al. | |
| 5,458,574 A | 10/1995 | Machold et al. | |
| 5,496,305 A | 3/1996 | Kittrell et al. | |
| 5,509,428 A | 4/1996 | Dunlop | |
| 5,533,958 A | 7/1996 | Wilk | |
| 5,571,215 A | 11/1996 | Sterman et al. | |
| 5,584,803 A | 12/1996 | Stevens et al. | |
| 5,593,424 A | 1/1997 | Northrup III | |
| 5,665,092 A | 9/1997 | Mangiardi et al. | |
| 5,682,906 A | 11/1997 | Sterman et al. | |
| 5,702,343 A | 12/1997 | Alferness | |
| 5,713,954 A | 2/1998 | Rosenberg et al. | |
| 5,718,725 A | 2/1998 | Sterman et al. | |
| 5,755,783 A | 5/1998 | Stobie et al. | |
| 5,800,334 A | 9/1998 | Wilk | |
| 5,800,528 A | 9/1998 | Lederman et al. | |
| 5,800,531 A | 9/1998 | Cosgrove et al. | |
| 5,814,097 A | 9/1998 | Sterman et al. | |
| 5,849,005 A | 12/1998 | Garrison et al. | |
| 5,855,601 A | 1/1999 | Bessler et al. | |
| 5,855,614 A | 1/1999 | Stevens et al. | |
| 5,865,791 A | 2/1999 | Whayne et al. | |
| 5,902,229 A | 5/1999 | Tsitlik et al. | |
| 5,928,281 A | 7/1999 | Huynh et al. | |
| 5,944,738 A | 8/1999 | Amplatz et al. | |
| 5,957,977 A | 9/1999 | Melvin | |
| 5,961,440 A | 10/1999 | Schweich, Jr. et al. | |
| 5,961,549 A | 10/1999 | Nguyen et al. | |
| 5,971,910 A | 10/1999 | Tsitlik et al. | |
| 5,971,911 A | 10/1999 | Wilk | |
| 5,972,022 A | 10/1999 | Huxel | |
| 5,972,030 A | 10/1999 | Garrison et al. | |
| 5,984,857 A | 11/1999 | Buck et al. | |
| 5,984,917 A | 11/1999 | Fleischman et al. | |
| 6,001,126 A | 12/1999 | Nguyen-Thien-Nhon | |
| 6,019,722 A * | 2/2000 | Spence et al. | 600/37 |
| 6,024,096 A | 2/2000 | Buckberg | |
| 6,024,756 A | 2/2000 | Huebsch et al. | |
| 6,045,497 A | 4/2000 | Schweich, Jr. et al. | |
| 6,050,936 A | 4/2000 | Schweich, Jr. et al. | |
| 6,059,715 A | 5/2000 | Schweich, Jr. et al. | |
| 6,071,303 A | 6/2000 | Laufer | |
| 6,077,214 A | 6/2000 | Mortier et al. | |
| 6,077,218 A | 6/2000 | Alferness | |
| 6,079,414 A | 6/2000 | Roth | |
| 6,085,754 A | 7/2000 | Alferness et al. | |
| 6,086,532 A | 7/2000 | Panescu et al. | |
| 6,095,968 A | 8/2000 | Snyders | |
| 6,102,944 A | 8/2000 | Huynh et al. | |
| 6,110,100 A | 8/2000 | Talpade | |
| 6,113,536 A * | 9/2000 | Aboul-Hosn et al. | 600/231 |
| 6,117,159 A | 9/2000 | Huebsch et al. | |
| 6,123,662 A | 9/2000 | Alferness et al. | |
| 6,125,852 A | 10/2000 | Stevens et al. | |
| 6,126,590 A | 10/2000 | Alferness | |
| 6,132,438 A | 10/2000 | Fleischman et al. | |
| 6,143,025 A | 11/2000 | Stobie et al. | |
| 6,155,968 A | 12/2000 | Wilk | |
| 6,155,972 A | 12/2000 | Nauertz et al. | |
| 6,162,168 A | 12/2000 | Schweich, Jr. et al. | |
| 6,165,119 A | 12/2000 | Schweich, Jr. et al. | |
| 6,165,120 A | 12/2000 | Schweich, Jr. et al. | |
| 6,165,121 A | 12/2000 | Alferness | |
| 6,165,122 A | 12/2000 | Alferness | |
| 6,165,183 A | 12/2000 | Kuehn et al. | |
| 6,169,922 B1 | 1/2001 | Alferness et al. | |
| 6,174,279 B1 | 1/2001 | Girard | |
| 6,179,791 B1 | 1/2001 | Krueger | |
| 6,182,664 B1 | 2/2001 | Cosgrove | |
| 6,190,408 B1 | 2/2001 | Melvin | |
| 6,193,648 B1 | 2/2001 | Krueger | |
| 6,197,053 B1 | 3/2001 | Cosgrove et al. | |
| 6,206,820 B1 | 3/2001 | Kazi et al. | |
| 6,217,610 B1 | 4/2001 | Carpentier et al. | |
| 6,221,013 B1 | 4/2001 | Panescu et al. | |
| 6,221,103 B1 | 4/2001 | Melvin | |
| 6,221,104 B1 | 4/2001 | Buckberg et al. | |
| 6,224,540 B1 | 5/2001 | Lederman et al. | |
| 6,230,714 B1 | 5/2001 | Alferness et al. | |
| 6,238,334 B1 | 5/2001 | Easterbrook, III et al. | |
| 6,241,654 B1 | 6/2001 | Alferness | |
| 6,245,102 B1 | 6/2001 | Jayaraman | |
| 6,245,105 B1 | 6/2001 | Nguyen et al. | |
| 6,250,308 B1 | 6/2001 | Cox | |
| 6,258,021 B1 | 7/2001 | Wilk | |
| 6,261,222 B1 | 7/2001 | Schweich, Jr. et al. | |
| 6,264,602 B1 | 7/2001 | Mortier et al. | |
| 6,269,819 B1 | 8/2001 | Oz et al. | |
| 6,283,993 B1 | 9/2001 | Cosgrove et al. | |
| 6,314,322 B1 | 11/2001 | Rosenberg | |
| 6,332,863 B1 | 12/2001 | Schweich, Jr. et al. | |
| 6,332,864 B1 | 12/2001 | Schweich, Jr. et al. | |
| 6,332,893 B1 | 12/2001 | Mortier et al. | |
| 6,338,712 B2 * | 1/2002 | Spence et al. | 600/201 |
| 6,375,608 B1 | 4/2002 | Alferness | |
| 6,379,366 B1 | 4/2002 | Fleischman et al. | |
| 6,402,680 B2 | 6/2002 | Mortier et al. | |
| 6,406,420 B1 | 6/2002 | McCarthy et al. | |
| 6,409,760 B1 | 6/2002 | Melvin | |
| 6,416,459 B1 | 7/2002 | Haindl | |
| 6,439,237 B1 | 8/2002 | Buckberg et al. | |
| 6,450,171 B1 | 9/2002 | Buckberg et al. | |
| 6,461,366 B1 | 10/2002 | Seguin | |
| 6,494,825 B1 | 12/2002 | Talpade | |
| 6,508,756 B1 | 1/2003 | Kung et al. | |
| 6,514,194 B2 | 2/2003 | Schweich, Jr. et al. | |
| 6,520,904 B1 | 2/2003 | Melvin | |
| 6,572,529 B2 | 6/2003 | Wilk | |
| 6,589,160 B2 | 7/2003 | Schweich, Jr. et al. | |
| 2001/0003986 A1 | 6/2001 | Cosgrove | |
| 2001/0005787 A1 | 6/2001 | Oz et al. | |
| 2001/0009976 A1 | 7/2001 | Panescu et al. | |
| 2001/0021874 A1 | 9/2001 | Carpentier et al. | |
| 2001/0029314 A1 | 10/2001 | Alferness et al. | |
| 2002/0007216 A1 | 1/2002 | Melvin | |
| 2002/0022880 A1 | 2/2002 | Melvin | |
| 2002/0026092 A1 | 2/2002 | Buckberg et al. | |
| 2002/0029783 A1 | 3/2002 | Stevens et al. | |
| 2002/0058855 A1 | 5/2002 | Schweich, Jr. et al. | |
| 2002/0065465 A1 | 5/2002 | Panescu et al. | |
| 2002/0091296 A1 | 7/2002 | Alferness | |
| 2002/0111533 A1 | 8/2002 | Melvin | |
| 2002/0111636 A1 | 8/2002 | Fleischman et al. | |
| 2002/0133055 A1 | 9/2002 | Haindl | |

| | | | |
|---|---|---|---|
| 2002/0143250 | A1 | 10/2002 | Panescu et al. |
| 2002/0161275 | A1 | 10/2002 | Schweich, Jr. et al. |
| 2002/0169359 | A1 | 11/2002 | McCarthy et al. |
| 2002/0173694 | A1 | 11/2002 | Mortier et al. |
| 2003/0028077 | A1 | 2/2003 | Alferness et al. |
| 2003/0032979 | A1 | 2/2003 | Mortier et al. |
| 2003/0045771 | A1 | 3/2003 | Schweich, Jr. et al. |

FOREIGN PATENT DOCUMENTS

| | | |
|---|---|---|
| EP | 0 583 012 | 2/1994 |
| EP | 0 820 729 A1 | 1/1998 |
| WO | 91/19465 | 12/1991 |
| WO | 95/06447 | 3/1995 |
| WO | 95/16476 | 6/1995 |
| WO | 96/04852 | 2/1996 |
| WO | 96/40356 | 12/1996 |
| WO | WO 97/14286 | 4/1997 |
| WO | WO 97/24082 | 7/1997 |
| WO | WO 97/24083 | 7/1997 |
| WO | 97/24101 | 7/1997 |
| WO | 98/03213 | 1/1998 |
| WO | 98/14136 | 4/1998 |
| WO | WO 98/17347 | 4/1998 |
| WO | 98/18393 | 5/1998 |
| WO | 98/26738 | 6/1998 |
| WO | 98/29041 | 7/1998 |
| WO | 98/32382 | 7/1998 |
| WO | WO 98/58598 | 12/1998 |
| WO | WO 99/00059 | 1/1999 |
| WO | 99/11201 | 3/1999 |
| WO | 99/13777 | 3/1999 |
| WO | WO 99/16350 | 4/1999 |
| WO | WO 99/22784 | 5/1999 |
| WO | WO 99/30647 | 6/1999 |
| WO | 99/30647 | 6/1999 |
| WO | 99/44534 | 9/1999 |
| WO | 99/44680 | 9/1999 |
| WO | WO 99/44969 | 9/1999 |
| WO | 99/52470 | 10/1999 |
| WO | WO 99/53977 | 10/1999 |
| WO | 99/56655 | 11/1999 |
| WO | WO 99/66969 | 12/1999 |
| WO | 00/02500 | 1/2000 |
| WO | WO 00/03759 | 1/2000 |
| WO | 00/06026 | 2/2000 |
| WO | 00/06028 | 2/2000 |
| WO | 00/13722 | 3/2000 |
| WO | 00/18320 | 4/2000 |
| WO | 00/27304 | 5/2000 |
| WO | 00/28912 | 5/2000 |
| WO | 00/28918 | 5/2000 |
| WO | 00/36995 | 6/2000 |
| WO | 00/42919 | 7/2000 |
| WO | 00/45735 | 8/2000 |
| WO | 00/61033 | 10/2000 |
| WO | 00/62727 | 10/2000 |
| WO | 01/03608 A1 | 1/2001 |
| WO | 01/21070 A1 | 3/2001 |
| WO | 01/21098 A1 | 3/2001 |
| WO | 01/21099 A1 | 3/2001 |
| WO | 01/50981 A1 | 7/2001 |

OTHER PUBLICATIONS

Sakakibara, "A Surgical Approach to the Correction of Mitral Insuffiency," *Annals of Surgery*, 142:196–203, 1955.

Glenn et al., "The Surgical Treatment of Mitral Insufficiency: The Fate of A Vascularized Transchamber Intracardiac Graft," *Annals of Surgery*, 141:510–518, Apr. 1955.

Kay et al., "Surgical Treatment of Mitral Insufficiency," *Surgery*, 37:697–706, May 1955.

Bailey et al. "The Surgical Correction of Mitral Insufficiency By The Use of Pericardial Grafts," *The Journal of Thoracic Surgery*, 28:551–603, Dec. 1954.

Harken et al., "The Surgical Correction of Mitral Insufficiency," *Surgical Forum*, 4:4–7, 1953.

Shumacker, Jr., "Attempts to Control Mitral Regurgitation," *The Evolution of Cardiac Surgery*, 203–210, 1992.

Edie, M.D. et al., "Surgical repair of single ventricle,"*The Journal of Thoracic and Carciov ascular Surgery*, vol. 66, No. 3, Sep., 1973, pp. 350–360.

McGoon, M.D. et al., "Correction of the univentricular heart hav ing two atriov entricular valves," *The Journal of Thoracic and Cardiov ascular Surgery*, vol. 74, No. 2, Aug., 1977, pp. 218–226.

Lev, M.D., et al., "Single (Prim itive) Ventricle," *Circulation*, vol. 39, May, 1969, pp. 577–591.

Westaby with Bosher, "Landm arks in Cardiac Surgery," 1997, pp. 198–199.

Shumacker, "Carciac Aneury sms," *The Evolution of Cardiac Surgery*, 1992, pp. 159–165.

Feldt, M.D., "Current status of the septation procedure for univentricular heart," *The Journal of Thoracic and Cardiov ascular Surgery*, vol. 82, No. 1, Jul., 1981, pp. 93–97.

Doty, M.D., "Septation of the univentricular heart," *The Journal of Thoracic and Carciov ascular Surgery*, vol. 78, No. 3, Sep., 1979, pp. 423–430.

Carpentier et al., "M yocardial Substitution with a Stim ulated Sk eletal Muscle: First Successful Clinical Case," Letter to the Editor, p. 1267, Sep. 25, 1996.

Ianuzzo et al., "Preservation of the Latissimus Dorsi Muscle During Cardiom yoplasty Surgery," *J. Card. Surg.*, 1996:11:99–108.

Ianuzzo et al., "On Preconditioning of Skeletal Muscle: Application to Dy namic Cardiom yoplasty," Invited Commentary, *J. Card. Surg.*, 1996:11:109–110.

Chachques et al., "Latissim us Dorsi Dynamic Cardiom yoplasty," *Ann. Thorac. Surg.*, 1989:47:600–604.

Moreira et al., "Latissim us Dorsi Cardiom yoplasty in the Treatment of Patients with Dilated Cardiom yopathy," Supplem ent IV Circulation, Sep. 25, 1996, 7 pgs.

Lucas et al., "Long–T erm Follow–Up (12 to 35 W eeks) After Dynamic Cardiomyoplasty," *JACC*, vol. 22, No. 3, Sep. 1993:758–67.

Batista et al., "Partial Lef t Ventriculectom y to Improve Left Ventricular Function in End–Stage Heart Disease," *J. Card. Surg.*, 1996:11:96–98.

"Congestive Heart Failure in the United States: A New Epidem ic" Data Fact Sheet, National Heart, Lung, and Blood Institute, National Institutes of Health, Dec. 9, 1996, pp. 1–6.

Kormos et al., "Experience with Univ entricular Support in M ortally Ill Cardiac Transplant Candidates," *Ann. T horac. Surg.*, 1990:49:261–71.

Wampler et al., "Treatment of Cardiogenic Shock with the Hem opump Left Ventricular Assist Device," *Ann. Thorac. Surg.*, 1991:52:506–13.

McCarthy et al., "Clinical Ex perience with the Nov acor Ventricular Assist Sy stem," *J. Thorac. Cardiovasc. Surg.*, 1991:102–578–87.

Burnett et al., "Im proved Survival After Hemopump Insertion in Patients Ex periencing Postcardiotomy Cardiogenic Shock During Cardiopulm onary Bypass," From the Section of Transplantation, Div ision of Cardiovascular Surgery, Texas Heart Institute and St. Luk e's Episcopal Hospital, Houston, T exas, dated even with or prior to Jan. 2, 1997, pp. 626–628.

Phillips et al., "Hem opump Support for the Failing Heart," From the Department of Cardiovascular Medicine and Surgery, Mercy Hospital Medical Center, Des M oines, Iowa, date ev en with or prior to Jan. 2, 1997, pp. 629–631.

Deeb et al., "Clinical Ex perience with the Nim bus Pump," From the University of Michigan Medical Center Section of Thoracic Surgery and Division of Cardiology, Ann Arbor, Michigan, date ev en with or prior to Jan. 2, 1997, pp. 632–636.

Bearnson et al., "Dev elopment of a Prototype Magnetically Suspended Rotor Ventricular Assist Device," *ASAIO Journal*, 1996, pp. 275–280.

Sakakibara et al., "A Muscle Powdered Cardiac Assist Dev ice for Right Ventricular Support: T otal Assist or Partial Assist?," *T rans. Am.Soc. Artif. Intern. Organs*, vol. XXXVI, 1990, pp. 372–375.

Medtronic, Inc. 1996 Annual Shareholders Report, 79 pages.

Abiomed, Inc. Annual Report 1996, 32 pages.

Press Release dated Sep. 16, 1996, "Abio med Wins $8.5 Million Federal Contract to Qualify its Artificial Heart for Human Trials," 5 pages.

Press Release dated Sep. 26, 1996, Abio Med's Temporary Artificial Heart System Reaches 200 U.S. M edical Center M ilestone, 1 page.

Press Release dated M ay 17, 1996, "Abio med Receives FDA Approval to Expand Indications for Use of Cardiac Assist System," 1 page.

Press Release dated O ct. 3, 1995, "Abio med Wins $4.35 Million Contract from the National Heart, Lung and Blood Institutes to Dev elop Implantable Heart Booster," 1 page.

Press Release dated Sep. 29, 1995, "Abio med" Wins NIH Grant to Develop Calcification–Resistant Plastic Heart Valve, 1 page.

Press Release dated Aug. 25, 1995, "Abio med Wins Research Grant from NIH to Develop Suturing Instrum ent for Abdominal surgery," 1 page.

Press Release dated Aug. 11, 1995, "Abio med Receives Grant from NIH to Develop Disposable Bearingless Centrif ugal Blood Pump," 1 page.

Press Release dated Jun. 9, 1995, "Abio med Receives Grant from National Institutes of Health to Develop a Laser W elding Technique for Tissue Repair," 1 page.

Press Release dated Apr. 27, 1995, "Abio med's Temporary Artificial Heart System Reaches 1,000 Patient Milestone; BVS–5000 in M ore Than 100 U.S. Medical Centers," 1 page.

"Reversible Cardiom yopathy," *Thoratec's Heartbeat*, vol. 10.2, Aug. 1996, 4 pages.

Tsai et al., "Surface Modifying Additiv es for Improved Device–Blood Com patibility," *ASAIO Journal*, 1994, pp. 619–624.

Farrar et al., "A New Sk eletal Muscle Linear–Pull Energy Convertor as a Power Source for Prosthetic Support Dev ices," *The Journal of Heart & Lung Transplantation*, vol. 11, No. 5, Sep., 1992, pp. 341–349.

Brochure entitled "T horatec Ventricular Assist Dev ice System—Because Heart Patients Com e in All Sizes," date even with or prior to Jan. 2, 1997, 5 pages.

Press Release dated O ct. 3, 1994, "Heartm ate System Becomes First Implantable Cardiac–Assist Device to be Approv ed for Commercial Sale in the U.S.," 2 pages.

Bocchi et al., "Clinical O utcome after Surgical Rem odeling of Left Ventricle in Candidates to Heart Transplantation with Idiopathic Dilated Cardiom ypathy—Short Term Results," date ev en with or prior to Jan. 2, 1997, 1 page.

Bach et al., "Early Improvement in Congestiv e Heart Failure after Correction of Secondary Mitral Regurgitation in End–Stage Cardiom yopathy," *American Heart Journal*, Jun. 1995, pp. 1165–1170.

Schuler et al., "Temporal Response of Left Ventricular Performance to Mitral Valve Surgery," vol. 59, No. 6, Jun. 1979, pp. 1218–1231.

Huikuri, "Effect of Mitral Valve Replacement on Left Ventricular Function in M itral Regurgitation," *Br. Heart J.*, vol. 49, 1983, pp. 328–333.

Pitarys II et al., "Long–Term Effects of Excision of the Mitral Apparatus on G lobal and Regional Ventricular Function in Hum ans," *JACC*, vol. 15, No. 3, Mar. 1, 1990, pp. 557–563.

Bolling et al., "Surgery for Acquired Heart Disease/Early Outcome of Mitral Valve Reconstruction in Patients with End–Stage Cardiom yopathy," *The Journal of Thoracic and Carciov ascular Surgery*, vol. 109, No. 4, Apr. 1995, pp. 676–683.

Masahiro et al., "Surgery for Acquired Heart Disease/Ef fects of Preserving Mitral Apparatus on Ventricular Sy stolic Function in M itral Valve Operations in Dogs," *T he Journal of Thoracic and Cardiovascular Surgery*, vol. 106, No. 6, Dec. 1993, pp. 1138–1146.

Dickstein et al., "Heart Reduction Surgery : An Analysis of the Impact on Cardiac Function," *T he Journal of Thoracic and Cardiov ascular Surgery*, vol. 113, No. 6, Jun. 1997, 9 pages.

McCarthy et al., "Early Results with Partial Left Ventriculectom y," From the Departments of Thoracic and Cardiov ascular Surgery, Cardiology, and Transplant Center, Clev eland Clinic Foundation, Presented at the 77th Annual M eeting of the American Association of Thoracic Surgeons, May 1997, 33 pages.

Alonso–Lej, M.D., "Adjustable Annuloplasty for Tricuspid Insufficiency," *The Annals of Thoracic Surgery*, vol. 46, No. 3, Sep. 1988, 2 pages.

Kurlansky et al., "Adjustable Annuloplasty for Tricuspid Insufficiency," *Ann. Thorac. Surg.*, 44:404–406, Oct. 1987.

Savage, M.D., "Repair of left ventricular aneurysm," *The Journal of Thoracic and Cardiov ascular Surgery*, vol. 104, No. 3, Sep., 1992, pp. 752–762.

Melvin, "Ventricular Radius Reduction W ithout Resection: A Com putational Analy sis," *ASAIO Journal*, 45:160–165, 1999.

Cox, "Left Ventricular Aneury sms: Pathophysiologic Observations and Standard Resection," *Seminars in Thoracic and Carciov ascular Surgery*, vol. 9, No. 2, Apr., 1997, pp. 113–122.

Boyd et al., "Tricuspid Annuloplasty," *The Journal of Thoracic Cardiov ascular Surgery*, vol. 68, No. 3, Sep. 1974, 8 pages.

acorn cardiovascular, inc., "Acorn Cardiov ascular Summary", undated.

acorn cardiovascular, inc., "Acorn Cardiovascular Company Overview", undated.

Batista, MD et al., "Partial Left Ventriculectomy to Treat End–Stage Heart Disease", *Ann. Thorac. Surg.*, 64:634–8, 1997.

Melvin DB et al., Reduction of Ventricular Wall Tensile Stress by Geometric Remodeling Device, *Poster text, ASAIO* 1999.

McCarthy, Transcription of Mar. 13, 2000 Presentation.

acorn cardiovascular, inc., "Acorn Cardiovascular Abstracts", Nov. 13, 2000.

Nation's First "Heart Jacket" Surgery to Treat Heart Failure Performed at HUP: Novel "Cardiac Support Device" Comes to America After Promising Results in Europe, Jun. 26, 2000.

acorn carciovascular, inc., Acorn Cardiovascular Company Overview, Jun. 2000.

acorn carciovascular, inc., Acorn Cardiovascular Business Plan, May 2000.

acorn cardiovascular, inc., "Acorn Cardiovascular Highlights Abstracts", Mar. 10, 1999.

acorn cardiovascular, inc., "Acorn Cardiovascular Highlights Abstracts", Apr. 19, 1999.

acorn cardiovascular, inc., "Acorn Cardiovascular Highlights Abstracts", Oct. 1, 1999.

acorn cardiovascular, inc., "Acorn Cardiovascular Highlights Abstracts", Nov. 9, 1999.

Melvin DB, "Ventricular Radius–Reduction Without Resection A Computational Assessment", undated.

Melvin DB et al., Reduction of Ventricular Wall Tensile Stress by Geometric Remodeling Device, undated.

* cited by examiner

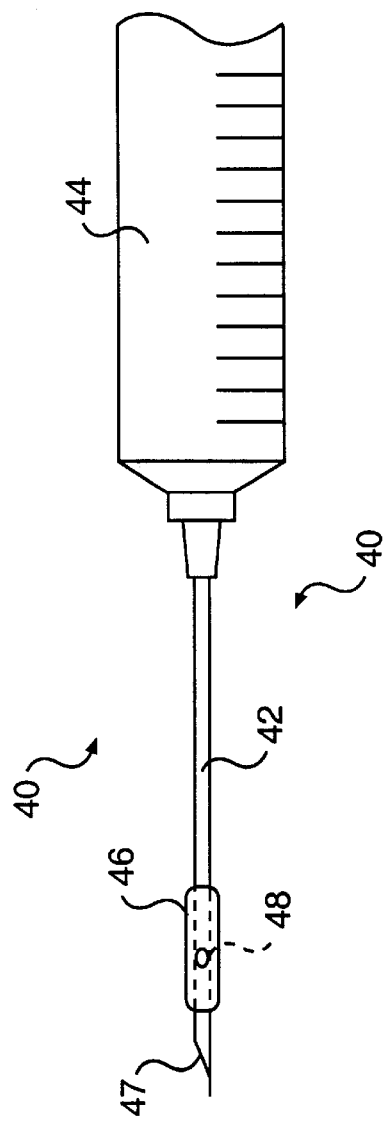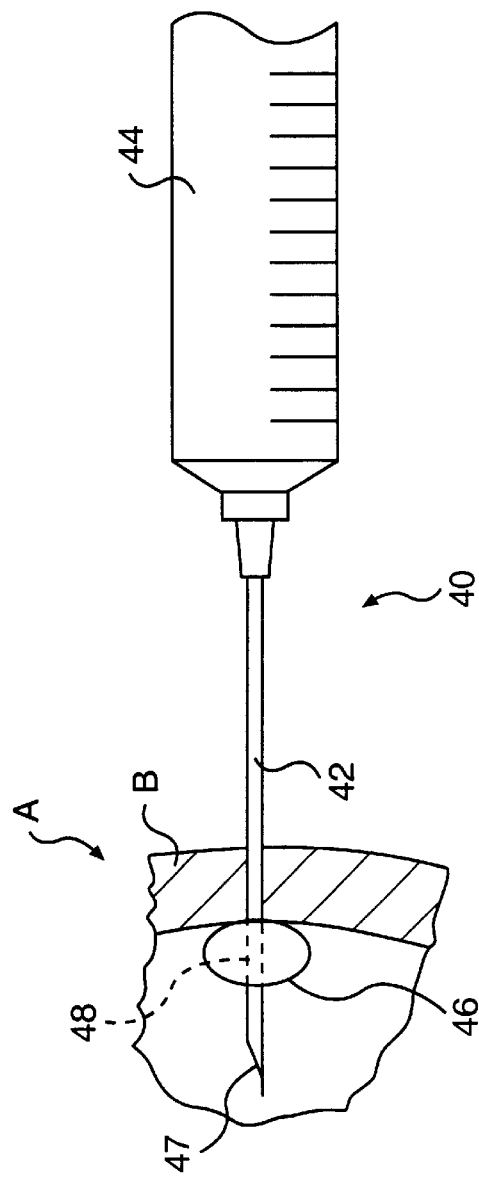

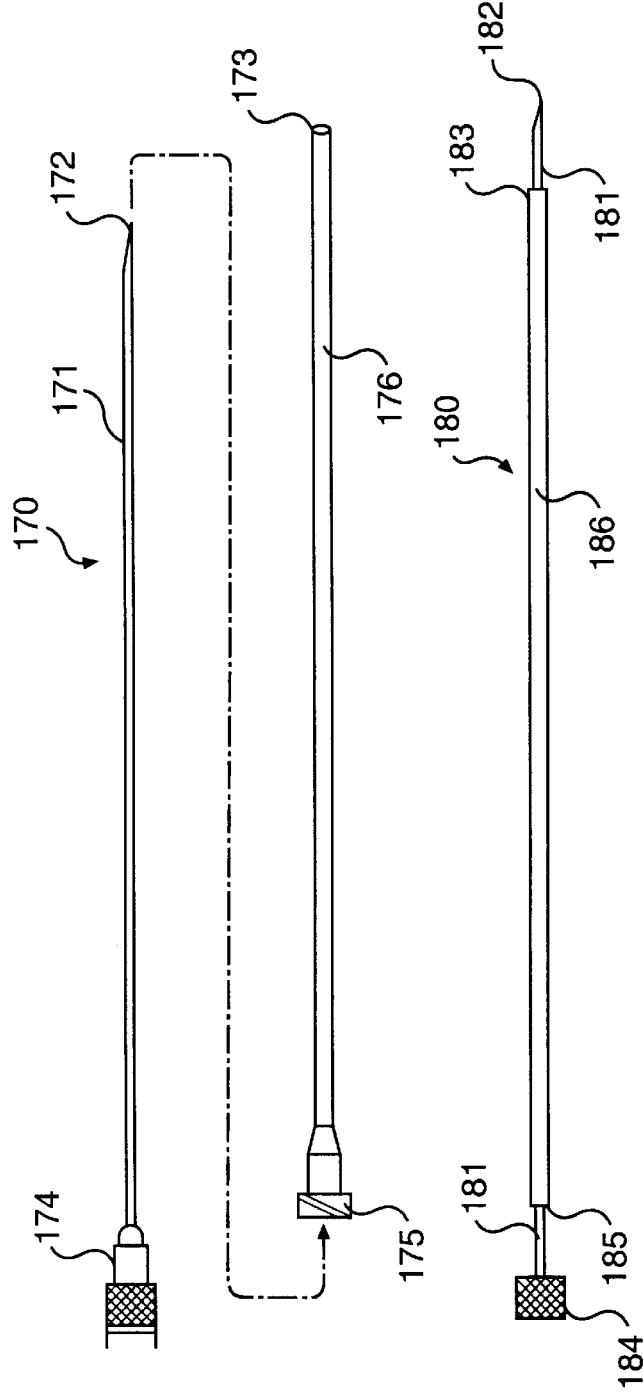

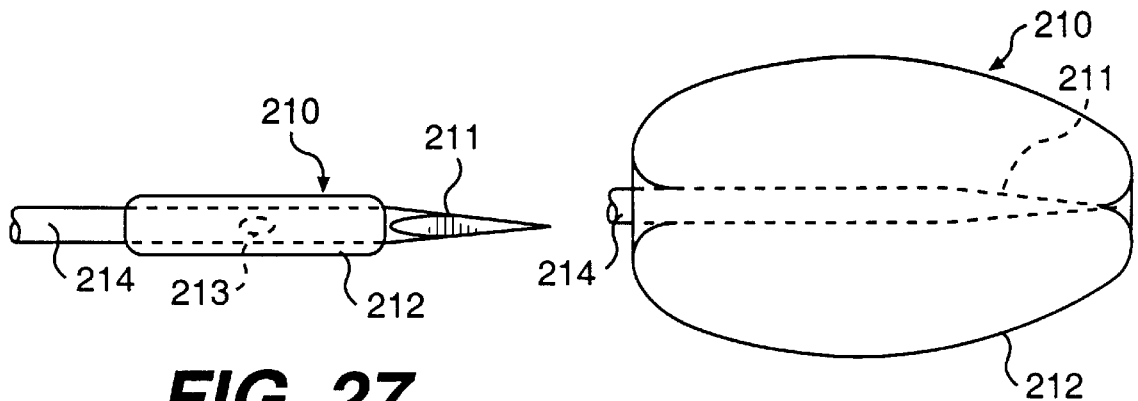
FIG. 27
FIG. 28
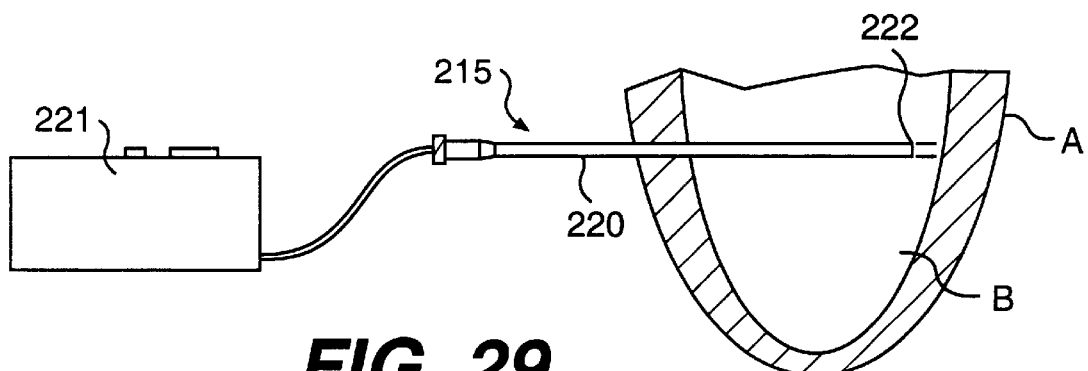
FIG. 29
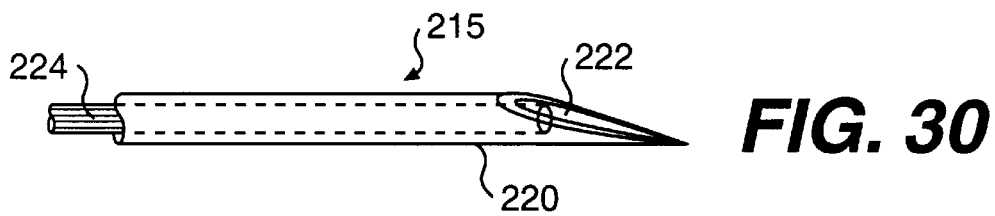
FIG. 30
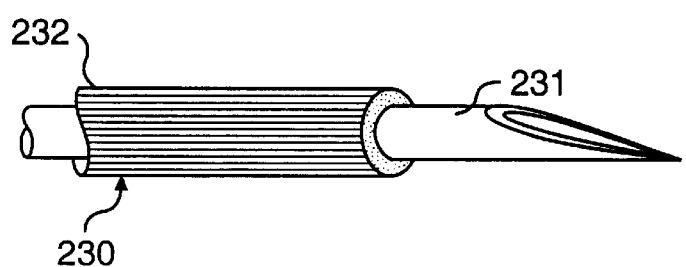
FIG. 31
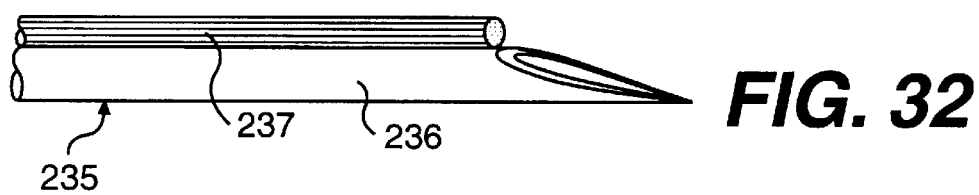
FIG. 32

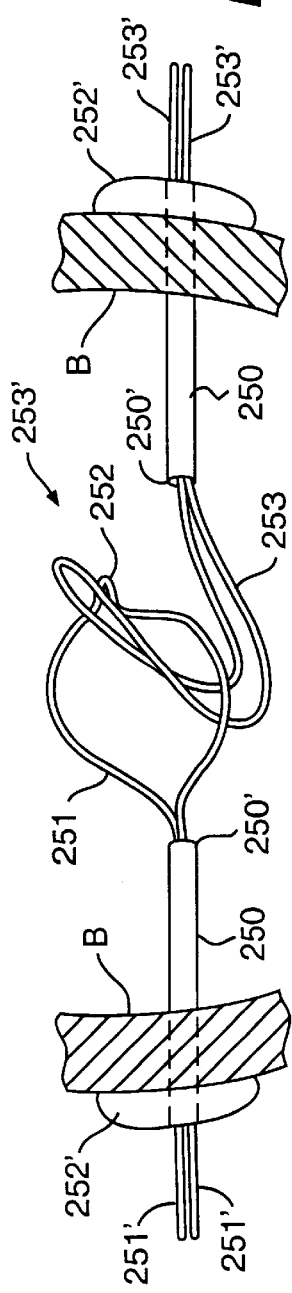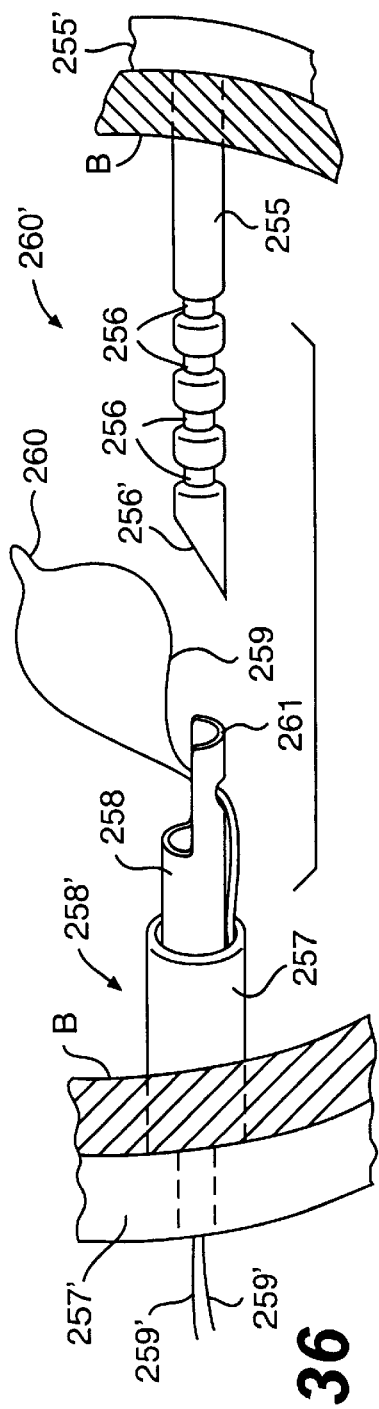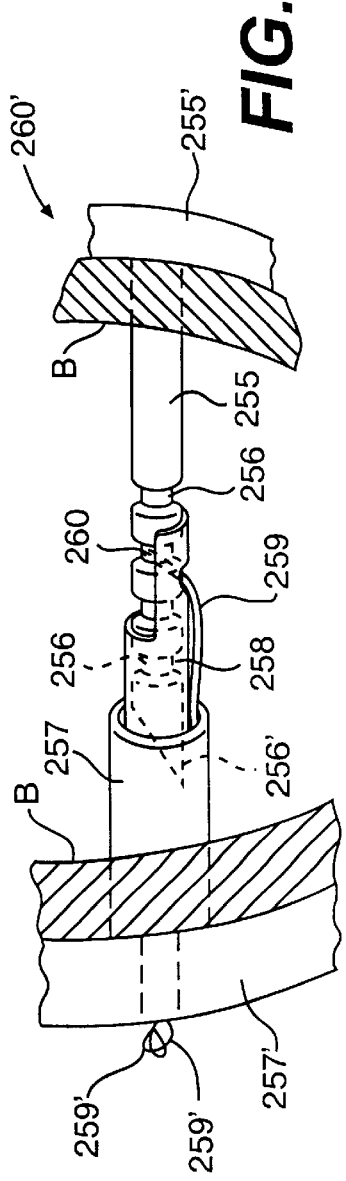

TRANSVENTRICULAR IMPLANT TOOLS AND DEVICES

RELATED APPLICATIONS

This application is a continuation of U.S. application Ser. No. 09/123,977 filed Jul. 29, 1998, now U.S. Pat. No. 6,260,552, and is related to U.S. application Ser. No. 09/124,321, filed Jul. 29, 1998 now U.S. Pat. No. 6,077,214, entitled "Stress Reduction Apparatus and Method" and U.S. application Ser. No. 09/124,286, filed Jul. 29, 1998, now U.S. Pat. No. 6,045,497, entitled "Heart Wall Tension Reduction Apparatus and Method", both of which are incorporated herein by reference.

FIELD OF THE INVENTION

The present invention pertains to the field of apparatus for treatment of a failing heart. In particular, the apparatus of the present invention is directed toward implanting a device for reducing wall stress in the failing heart.

BACKGROUND OF THE INVENTION

The syndrome of heart failure is a common course for the progression of many forms of heart disease. Heart failure may be considered to be the condition in which an abnormality of cardiac function is responsible for the inability of the heart to pump blood at a rate commensurate with the requirements of the metabolizing tissues, or can do so only at an abnormally elevated filling pressure. There are many specific disease processes that can lead to heart failure with a resulting difference in pathophysiology of the failing heart, such as the dilatation of the left ventricular chamber. Etiologies that can lead to this form of failure include idiopathic cardiomyopathy, viral cardiomyopathy, and ischemic cardiomyopathy.

The process of ventricular dilatation is generally the result of chronic volume overload or specific damage to the myocardium. In a normal heart that is exposed to long term increased cardiac output requirements, for example, that of an athlete, there is an adaptive process of ventricular dilation and myocyte hypertrophy. In this way, the heart fully compensates for the increased cardiac output requirements. With damage to the myocardium or chronic volume overload, however, there are increased requirements put on the contracting myocardium to such a level that this compensated state is never achieved and the heart continues to dilate.

The basic problem with a large dilated left ventricle is that there is a significant increase in wall tension and/or stress both during diastolic filling and during systolic contraction. In a normal heart, the adaptation of muscle hypertrophy (thickening) and ventricular dilatation maintain a fairly constant wall tension for systolic contraction. However, in a failing heart, the ongoing dilatation is greater than the hypertrophy and the result is a rising wall tension requirement for systolic contraction. This is felt to be an ongoing insult to the muscle myocyte resulting in further muscle damage. The increase in wall stress is also true for diastolic filling. Additionally, because of the lack of cardiac output, there is generally a rise in ventricular filling pressure from several physiologic mechanisms. Moreover, in diastole there is both a diameter increase and a pressure increase over normal, both contributing to higher wall stress levels. The increase in diastolic wall stress is felt to be the primary contributor to ongoing dilatation of the chamber.

Prior art treatments for heart failure fall into three generally categories. The first being pharmacological, for example, diuretics. The second being assist systems, for example, pumps. Finally, surgical treatments have been experimented with, which are described in more detail below.

With respect to pharmacological treatments, diuretics have been used to reduce the workload of the heart by reducing blood volume and preload. Clinically, preload is defined in several ways including left ventricular end diastolic pressure (LVEDP), or left ventricular end diastolic volume (LVEDV). Physiologically, the preferred definition is the length of stretch of the sarcomere at end diastole. Diuretics reduce extra cellular fluid which builds in congestive heart failure patients increasing preload conditions. Nitrates, arteriolar vasodilators, angiotensin converting enzyme inhibitors have been used to treat heart failure through the reduction of cardiac workload through the reduction of afterload. Afterload may be defined as the tension or stress required in the wall of the ventricle during ejection. Inotropes such as digoxin are cardiac glycosides and function to increase cardiac output by increasing the force and speed of cardiac muscle contraction. These drug therapies offer some beneficial effects but do not stop the progression of the disease.

Assist devices include, for example, mechanical pumps. Mechanical pumps reduce the load on the heart by performing all or part of the pumping function normally done by the heart. Currently, mechanical pumps are used to sustain the patient while a donor heart for transplantation becomes available for the patient.

There are at least three surgical procedures for treatment of heart failure: 1) heart transplant; 2) dynamic cardiomyoplasty; and 3) the Batista partial left ventriculectomy. Heart transplantation has serious limitations including restricted availability of organs and adverse effects of immunosuppressive therapies required following heart transplantation. Cardiomyoplasty includes wrapping the heart with skeletal muscle and electrically stimulating the muscle to contract synchronously with the heart in order to help the pumping function of the heart. The Batista partial left ventriculectomy includes surgically remodeling the left ventricle by removing a segment of the muscular wall. This procedure reduces the diameter of the dilated heart, which in turn reduces the loading of the heart. However, this extremely invasive procedure reduces muscle mass of the heart.

SUMMARY OF THE INVENTION

The present invention relates to methods and devices for placing a transventricular splint to reduce mechanical heart wall muscle stress. Heart wall muscle stress is a stimulus for the initiation and progressive enlargement of the left ventricle in heart failure. Although the primary focus of the methods of the present invention is heart failure and thus placement of a splint on the left ventricle, the methods and devices of the present invention could be used to place a splint or reduce stress in the heart's other chambers.

The transventricular splints placed by the tools and methods of the present invention can reduce heart wall stress throughout the cardiac cycle including end diastole and end systole. Alternately, they can be used to reduce wall stress during the portions of the cardiac cycle not including end systole. The splints which operate throughout the cardiac cycle are referred to herein as "full cycle splints". Those splints which do not operate to reduce wall stress during end systole are referred to as "restrictive devices" or, more specifically, "restrictive splints". Splints reduce left ventricle wall stress by altering the geometric shape of the left ventricle.

In the preferred embodiment of the present invention, tools are provided to interconnect oppositely disposed ventricular walls by a transventricular splint, including a tension member and anchors disposed on opposite ends of the tension member. First access is gained to the heart either by opening a patient's chest or less invasively by port or trocar. The points on the ventricular walls to be interconnected by the splint are then identified. The locations are preferably marked. The tension member is then placed to extend between the marked locations. The distance between the marked location is preferably measured. The wall of the ventricles are drawn toward each other. The anchors are secured to the tension member. The tension member is trimmed or cut to size in view of the relative spacing of the anchors. The anchors are then secured to the heart.

In this manner, portions of the walls of the ventricle are fixed in a drawn position reducing the radius of curvature of the majority of the ventricle and thereby reducing the tension within the ventricle wall.

BRIEF DESCRIPTION OF THE FIGURES

Referring now to the drawings wherein like reference numerals refer to like elements throughout the several views.

FIG. 8 is a side view of a balloon locator device;

FIG. 9 is a side view of balloon locator device with balloon inflated;

FIG. 22 is a side view of a splint delivery guide;

FIG. 23 is an alternate embodiment of a splint delivery guide;

FIG. 24 is an alternate embodiment of a stylet;

FIG. 25 is yet another alternate embodiment of a stylet including a retractable sheath in a retracted position;

FIG. 26 is a view of the stylet of FIG. 25 showing the sheath covering the tip of the stylet;

FIG. 27 is a yet another alternate embodiment of a stylet including a balloon disposed proximate the tip;

FIG. 28 is a view of the stylet of FIG. 27 wherein the balloon is inflated to cover the tip of the stylet;

FIG. 29 is a view of yet another alternate embodiment of a splint delivery guide including an optical fiber;

FIG. 30 is a view of the tip of the guide of FIG. 29;

FIG. 31 is an alternate embodiment of a guide including an optical fiber;

FIG. 32 is a view of yet another alternate embodiment of a guide including an optical fiber;

FIG. 35 is a view of an alternate embodiment of a splint and delivery device;

FIG. 36 is a view of yet another alternate embodiment of a splint and delivery device;

FIG. 37 is a view of the device of FIG. 36 connected in a left ventricle;

DETAILED DESCRIPTION OF THE INVENTION

The present invention relates to methods and tools for implanting a transventricular splint. The transventricular splint reduces heart wall stress by changing ventricular geometry. A splint can be full cycle or restrictive. If a splint is full cycle, it engages, i.e., alters the generally globular ventricular shape throughout the cardiac cycle. If the splint is restrictive, it does not change the generally globular shape of the ventricle at end systole.

Figure 1:
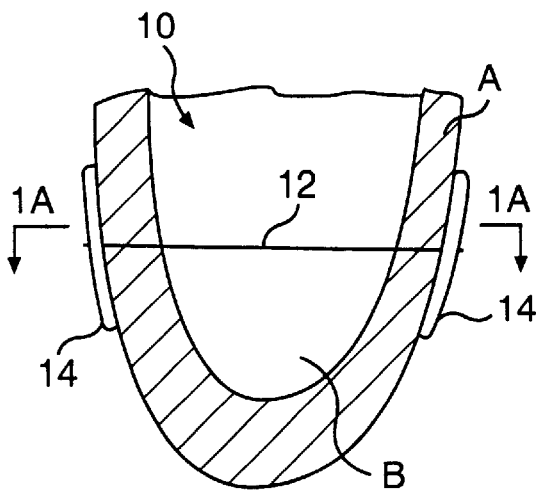
FIG. 1 is a cross sectional view of the left ventricle including a transventricular splint.
Figure 1A:
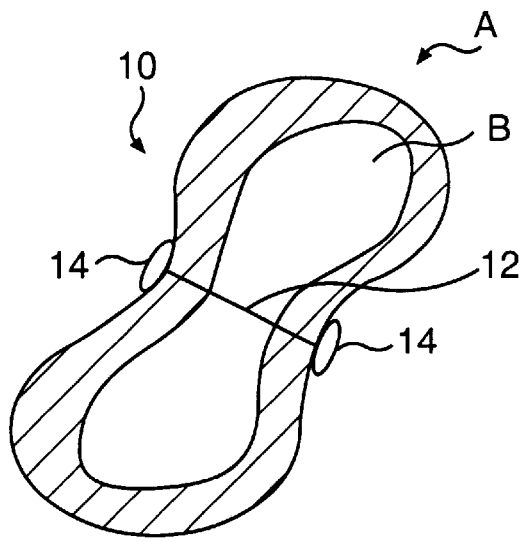
FIG. 1A is a generally horizontal cross sectional view of a left ventricle including the transventricular splint of FIG. 1.
Figure 2:
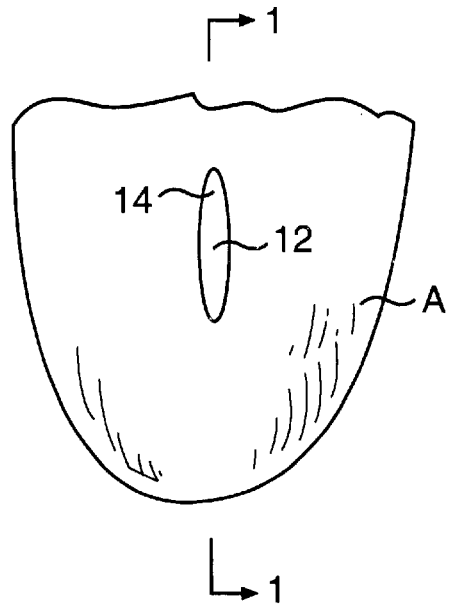
FIG. 2 is an exterior view of the heart of FIG. 1 and anchor pad of the transventricular splint.

FIG. 1 is a vertical cross sectional view of a left ventricle view B of a heart A. A typical transventricular splint 10 is disposed across ventricle B. Splint 10 includes a tension member 12. Connected to opposite ends of tension member 12 are anchors 14. Anchors 14 engage the walls of ventricle B to create a shape change either full cycle or restrictively. FIG. 1A is a horizontal cross sectional view of left ventricle B taken from FIG. 1 showing left ventricle B in a bi lobe shape as a result of the implantation of splint 10. FIG. 2 is a vertical exterior view of heart A showing splint 10, one end of tension member 12 and an anchor 14.

In a preferred method of implanting a transventricular splint, access is gained to the heart. The entry and/or exit points for the splint's tension member are identified. These locations are preferably marked. The tension member is then delivered transventricularly either from outside the heart to the inside, or from the inside of the heart to the outside. The anchors are delivered or deployed. The epicardial length is preferably measured to calibrate the magnitude of the shape change, tension member length, and thus heart wall stress reduction. The magnitude of the stress reduction is a function of the tension member length. (See U.S. patent application Ser. No. 08/933,456, filed Sep. 18, 1997 and incorporated herein by reference.) The heart walls are then drawn together by adjusting the tension member length and/or anchor spacing. The heart walls are drawn toward each other in view of the desired tension member length. The anchors are secured to maintain the length of the tension member. Preferably any portion of the tension member not lying between the anchors is removed. The anchors are preferably secured to the heart to limit relative movement between the anchors and the heart.

Some of the devices and methods disclosed in this application lend themselves to open chest procedures, whereas others lend themselves either to open chest procedures or less invasive procedures. Various cardiac surgical procedures are being done via partial thoracotomy between ribs. Thoroscopes and trocars are often utilized. Certain embodiments of the invention are amenable to these types of less invasive surgery. As is known to one skilled in the art, ports, windows and trocars are available to access the heart to limit patient trauma relative to open chest procedures. One or more access sites can be used during a less invasive procedure to gain access to the heart through the chest wall from a left lateral direction, right lateral direction, anterior and/or posterior direction. For example, during a less invasive splint implantation procedure, opposite ends of a tension member can be accessed by left and right lateral ports, where an anterior port is used to deliver the tension member. During less invasive procedures, the surgeon's hands preferably remain outside of the patient'; body.

When gaining access to the heart by way of a window trocar, both the diaphragm and lungs should be avoided. If the lungs are an obstruction to placement of the trocar and tension member, in some instances they may be moved without deflation. In yet other instances, if the lungs are substantially disposed between the selected chest access point and the heart, the patient may be placed on heart lung bi-pass and the patient's lungs deflated. Ventilation with or without deflation of the lungs may be desirable.

Once access to the heart through the chest wall has been gained, the splint placement location should be determined. Determining the desirable location of the splint is important to the performance and safety of the device. It is desirable to avoid external structures such as coronary vessels to avoid negatively effecting the perfusion of blood through the heart wall muscle. It is also desirable to avoid internal structures such as valve apparatus including chordae. To determine where to place the splint, the heart can be viewed with the naked eye, echo imaging, echo transesophageally or epicardially and fluoroscopy. Various devices can be used to locate entry or exit points by echo imaging or fluoroscopy.

Figure 3:
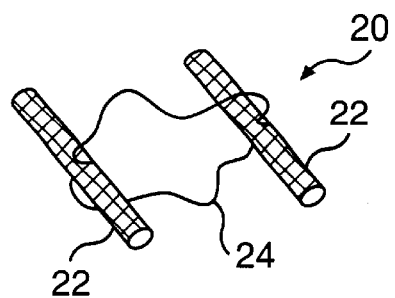
FIG. 3 is a location device with bars.
Figure 4:
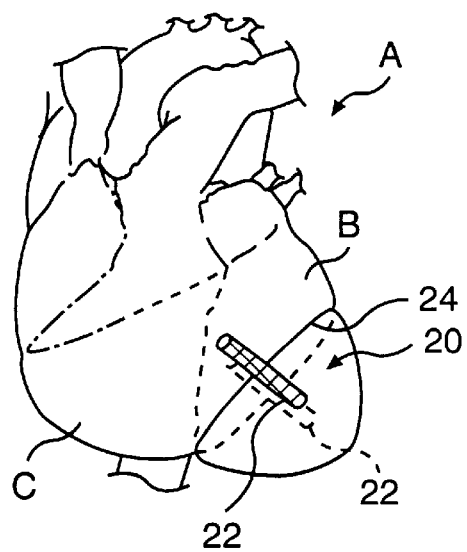
FIG. 4 is an exterior view of a heart including the location device of FIG. 3.

FIG. 3 is a perspective view of a locating device 20 including two knurled bars 22 interconnected by an elastic member 24. FIG. 4 is a view of a heart A including a left ventricle B and right ventricle C. Device 20 is shown disposed on left ventricle B. Bars 22 can be echo imaged or viewed by fluoroscopy simultaneously with the left ventricle. When viewed by fluoroscopy, coronary vessels can be advantageously visualized by introducing contrast medium therein. Additionally, bars 22 should be made from a substantially radiopaque material if used for fluoroscopic imaging.

In use, bars 22 are placed on heart A as shown in FIG. 4. Bars 22 appear to be positioned such that the coronary vessels and internal structures would be avoided, were the tension member to be extended through the heart between the location of bars 22. The location of the bars can be the location of the splint tension member. If not, the bars should be shifted into a better location until an acceptable location is found.

In addition to avoiding coronary vessels and internal anatomical structures, imaging can be used to determine if the proposed location of the splint will produce the desired shape change of the chamber. This could be accomplished with device 20 by pushing knurled bars 22 into the left ventricle and observing the change in chamber geometry by imaging.

Figure 5:
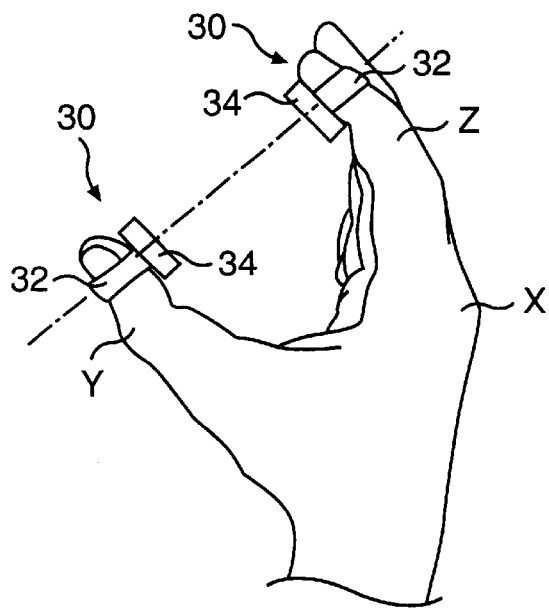
FIG. 5 is a hand including a finger echo locator device.
Figure 6:
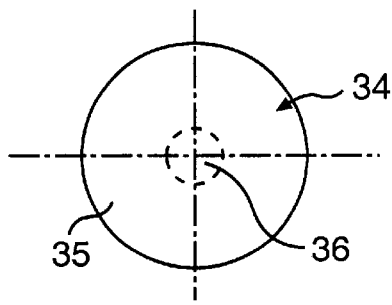
FIG. 6 is a top view of the echo locator device of FIG. 5.
Figure 7:
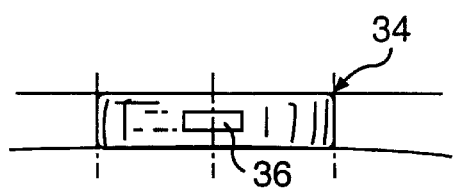
FIG. 7 is a side view of the echo locator device of FIG. 6.

FIG. 5 is a view of a human hand X including a thumb Y and a forefinger Z. An alternate locating device 30 is shown attached to thumb Y and forefinger Z by rings 32. Device 30 also includes a echo visible pad 34. Pads 34 can be used in the same way as knurled bars 22, but rather than being held together by a string 24, pads 34 can be held in place by the user. FIG. 6 is a view of the surface of pad 34 which would be in contact with heart A during use. Pad 34 preferably includes an echogenic marker 36 enclosed within a material which has a similar density to the heart wall. The similar density material will reduce echo scatter/reflection versus transmission at the surface and provide easier visualization of echo marker 36. FIG. 7 is a side view of pad 34 of FIG. 6.

FIG. 8 is a side view of a locating device 40. Device 40 can include a syringe 44 having a hypodermic needle 42 in which end 47 preferably does not include an exit lumen or orifice. The lumen does, however, extend through the remainder of hypodermic needle 42. A balloon envelope is connected to a portion of hypodermic needle 42 proximate its end 47. An orifice provides fluid communication between the lumen through hypodermic needle 42 and inside balloon 46. Balloon 46 can be inflated with a echo visible or fluoroscopic visible medium.

FIG. 9 is a view of locating device 40 in which balloon 46 is shown inflated within left ventricle B of heart A. By using locator 40 tension member entry/exit points can be evaluated in closer proximity to internal structures than when a locator is placed on the external surface of the heart.

Figure 10:
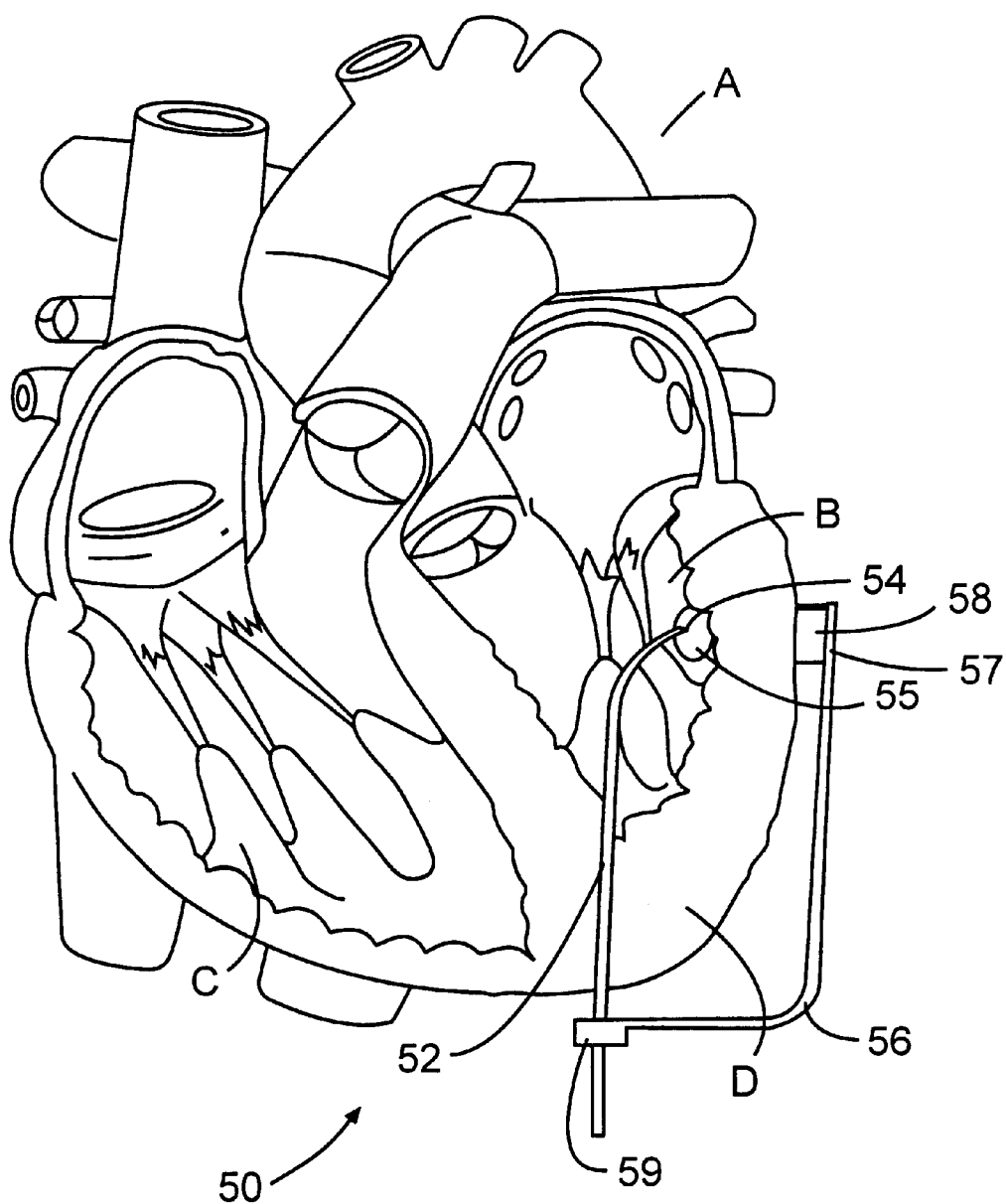
FIG. 10 is a view of a mechanical locator disposed within and outside of a left ventricle.

FIG. 10 is a vertical cross sectional view of heart A including left ventricle B, right ventricle C and an apex D. A locator device 50 is shown disposed on heart A. Locator device 50 includes apical insert branch 52 which preferably includes an elongate shaft having an inflation lumen and a tension member delivery lumen extending therethrough. The shaft preferably bends transversely near its distal end 54. A balloon 55 similar to the balloon of locator device 40 of FIGS. 8 and 9 is connected to the distal end of branch 52. Balloon 55 can be inflated with a medium visible by echo imagery or fluoroscopy to locate a tension member entry or exit point on the internal surface of the ventricle wall in a manner similar to locating device 40 of FIGS. 8 and 9. An optical fiber could be extended through branch 52 and used as described with respect to the device of FIG. 29.

Locator device 50 preferably includes an external branch arm 56 connected to branch 52 at connector 59. Branch 56 is bent such that its distal end 57 is disposed adjacent distal end 54 of branch arm 52. An additional marker 58 is preferably connected to distal end 57 of branch arm 56. Marker 58 is preferably made of material visible either through echo imaging or fluoroscopy. Branch arm 56 is preferably connected to branch arm 52 such that as branch arm 52 is rotated, marker 55 and marker 58 will maintain their relative position to each other, even as their position changes with respect to left ventricle B.

Figure 11:
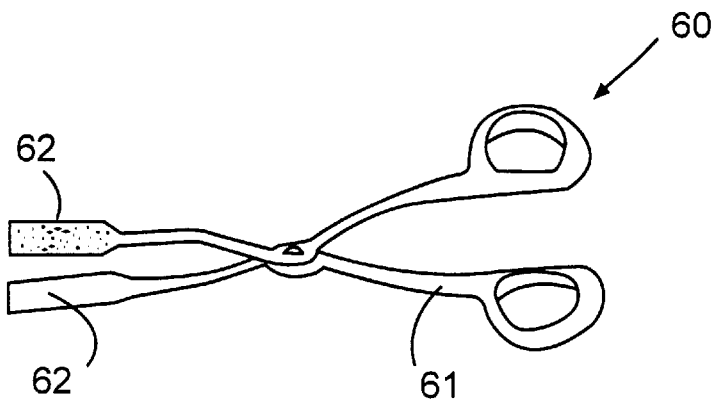
FIG. 11 is a clamp locator device.
Figure 12:
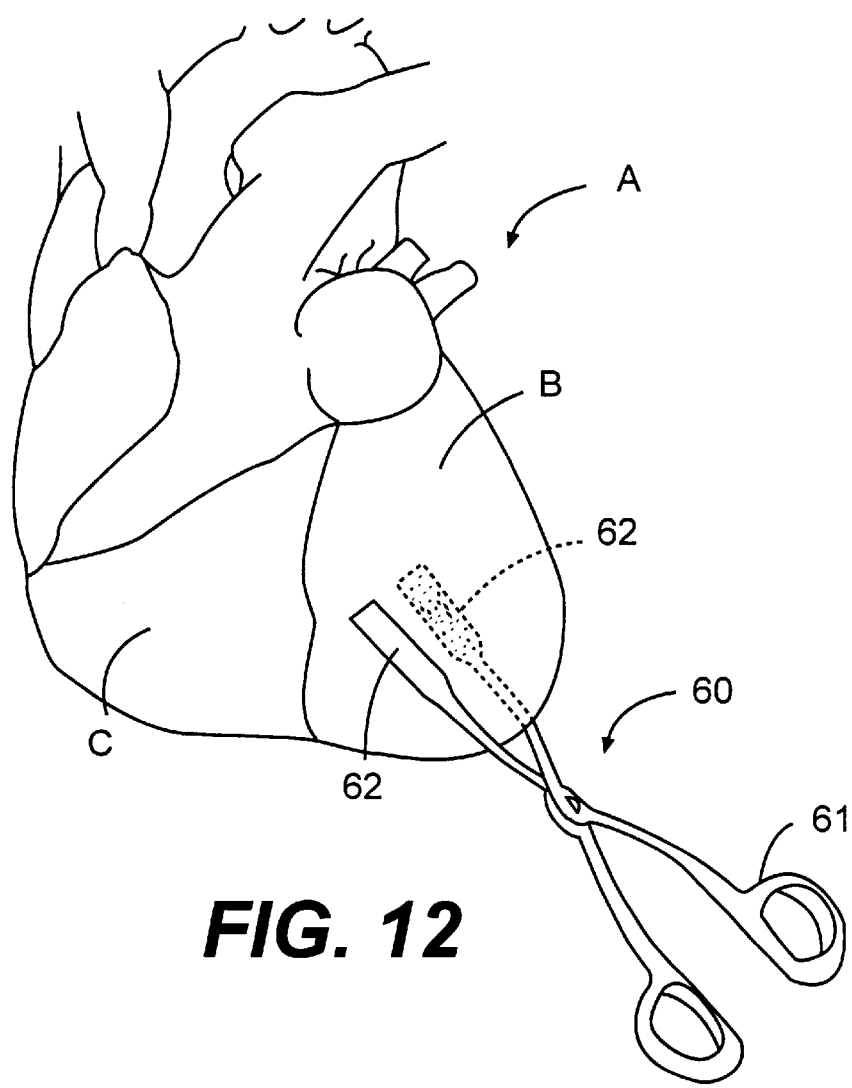
FIG. 12 is a view of the device of FIG. 11 disposed on a left ventricle.

FIG. 11 is a perspective view of a scissor-like clamp 60 which has a handle 61 and two clamps ends 62 which are made of a material which is echogenic or by fluoroscopy. Clamp 60 can be opened or closed freely as a pair of scissors or have a locking mechanism to releasably fix the spacing between ends 62. FIG. 12 is a vertical view of a heart A similar to that view of heart A in FIG. 4. Here rather than placing bars 22 on the heart, ends 62 of clamp 60 are placed on the heart. Ends 62 can be used in a manner similar to bars 22 as described above to locate a desirable positioning of a splint on left ventricle B.

After the tension member entrance/exit points or anchor points on the heart have been identified for the transventricular splint, the locations can be marked in various ways to assist a surgeon in accurate placement of a splint when the locator has been removed. Tissue marking pens can be used to mark the location for splint placement. Additionally, sutures can also be placed to provide a marker. For example, a purse string suture with or without pledgets could be used to enhance sealing of the tissue around the tension member to reduce bleeding as the tension member is advanced through the heart wall.

Figure 13:
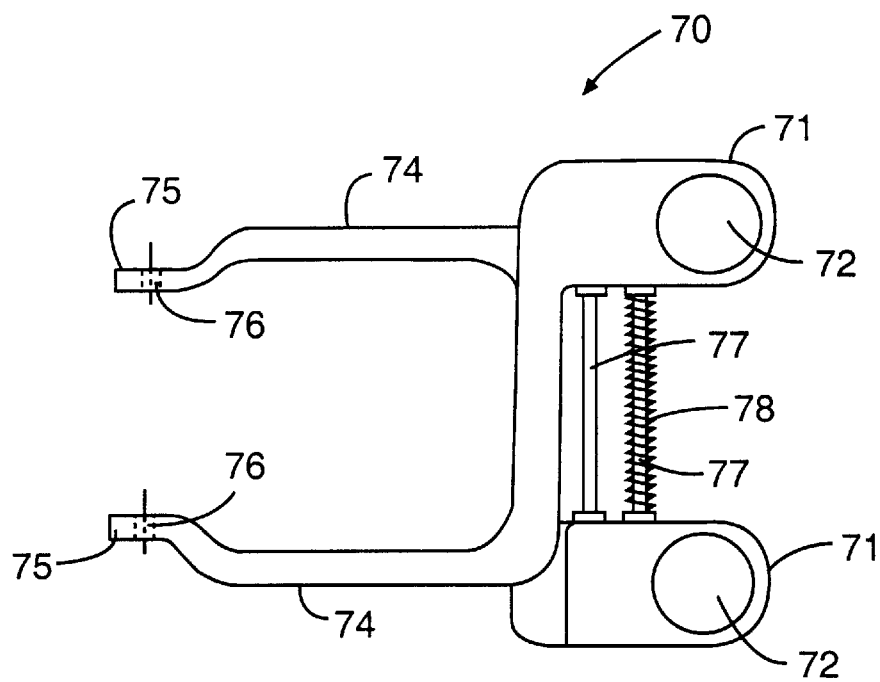
FIG. 13 is a view of an alignment tool.

After marking tension member entry/exit points or anchoring points, an open chest alignment device, such as alignment device 70 of FIG. 13, can be placed on the heart to aid in the insertion of the tension member through the chamber from outside of the heart. Alignment device 70 includes a handle 71 including holes 72 for the thumb and index finger of an operator. Alignment device 70 includes two alignment arms having distal pad ends 75. Ends 75 include apertures 76 for receiving a tension member guide and/or tension member therethrough. Pads 75, arm 74 and handles 71 are preferably aligned on shaft 77 such that as handle 71 are drawn toward each other by an operator. Arms 74 and pads 75 will remain generally parallel to each other. A spring 78 biases handles 71 apart, and arms 74 and pads 75 together. A locking mechanism can be provided to fix pads 75 in position when a desired spacing has been achieved. Apertures 76 preferably remain axially aligned throughout the operational spacing of pads 75.

In use, pads 75 are disposed on the heart such that apertures 76 are placed over the location or markings previously determined for the exit/entry points. Handles 71 are pulled apart until pads 75 are in engagement with the exterior surface of the heart. Alignment device 70 is now in position for the next step of the splint placement procedure.

Figure 14:
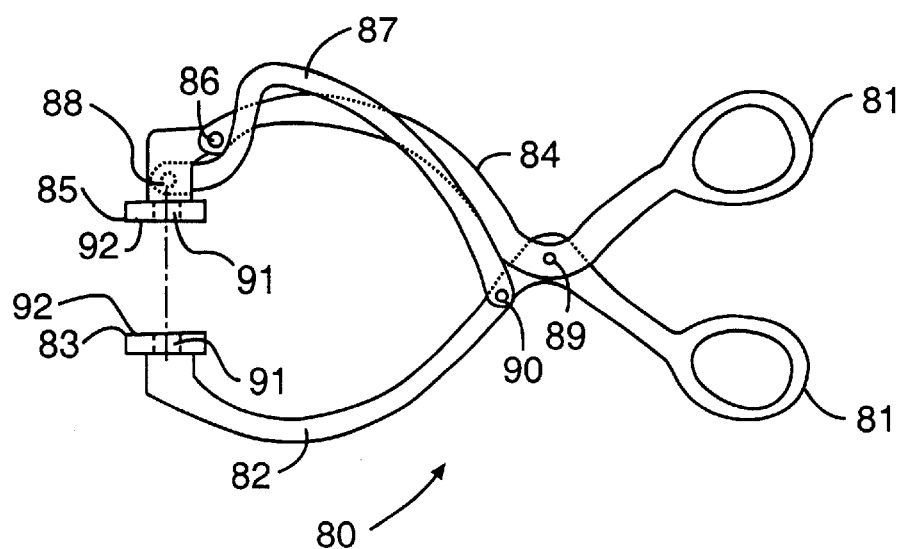
FIG. 14 is a view of an alternative alignment tool.

FIG. 14 is an alternate embodiment of an alignment device 80. Alignment device 80 includes handles 81 and an arm 84 and 86 which are pivotable about a pin 89. Disposed at the end of arm 82 is an alignment pad 83. An alignment pad 85 is rotatably connected by pin 86 to arm 84. A third arm 87 is pivotally connected to arm 82 by pin 90 and pivotally connected to pad 85 by a pin 88. Pads 83 and 85 each have an aperture 91 therethrough. Pads 83 and 85 have heart engaging surfaces 92 which are preferably parallel to each other within an operational spacing of pads 83 and 85. Apertures 91 are preferably axially aligned within that operational spacing of pads 83 and 85.

The spacing of pads 83 and 85 can be manipulated by moving handles 81 toward each other to increase the spacing of pads 83 and 85 or away from each other to decrease the spacing. Pads 83 and 85 preferably engage the heart such that apertures 91 are axially aligned and disposed on the desired entry/exit point for the tension member. The closer handles 81 are moved together, the further pads 83 and 85 move apart.

Figure 15:
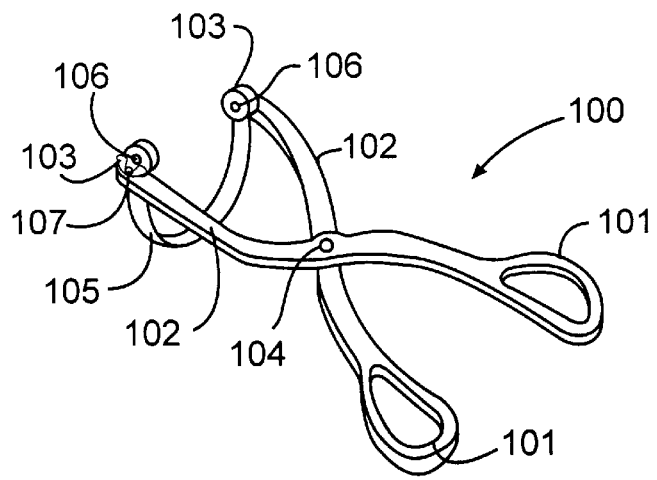
FIG. 15 is yet another alternative alignment tool.

FIG. 15 is yet an another alternate embodiment of an alignment device 100. Alignment device 100 includes handles 101 and elongate arms 102 pivotable about pin 104. At the end of elongate arms 102, opposite handles 101, are alignment pads 103 having orifices 106 extending therethrough. A flexible band 105 extends between pads 103.

Figure 15A:
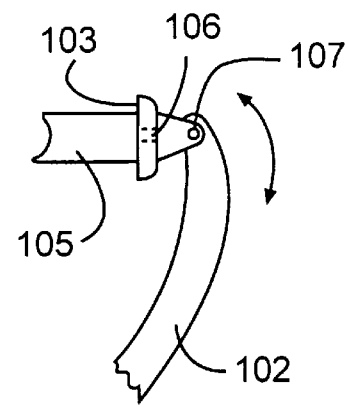
FIG. 15A is a detail of the alignment tool of FIG. 15.

As described above with respect to the alignment devices of FIGS. 13 and 14, the opposite pad orifices should be in axial alignment when placed on the heart. In the case of device 100, this can be accomplished by pivotally mounting pads 103 on arms 102 about a pin 107. FIG. 15A is a detail of a pad 103 pivotally mounted about pin 107 to arm 102. The arrow in FIG. 15A shows the direction that pad 13 can pivot about point 107. It can be appreciated that if opposite pads 103 are mounted as shown in FIG. 15A and if band 105 is sufficiently rigid, band 105 can hold orifices 106 of opposite pads 103 in axial alignment while arms 102 are pivoted about pin 104.

Since during the typical implant procedure the heart is still beating, it is preferable to equip the pads of the alignment devices 70, 80 and 100 with stabilizing apparatus. The apparatus of FIGS. 16–20 could be incorporated into the pads of alignment devices 70, 80 and 100.

Figure 16:
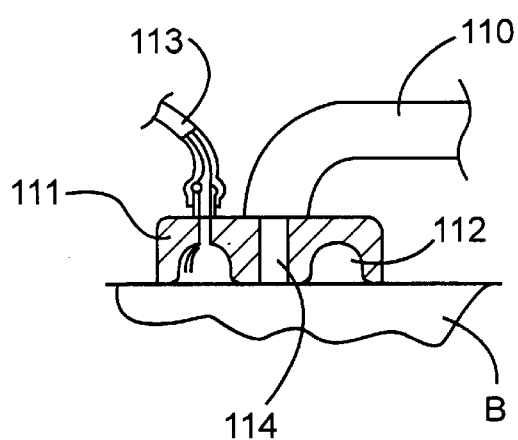
FIG. 16 is a cross sectional view of an alignment tool pad with stabilizing apparatus.

FIG. 16 is a cross sectional view of a pad 111 disposed at an end of an alignment device arm 110. The pad is shown in engagement with the external wall of left ventricle B. Pad 111 includes an aperture 114 extending therethrough for receiving a tension member guide (described in more detail below) and/or tension member. An annular trough 112 is disposed around aperture 114. Annular trough 112 is connected to a vacuum source line 113 such that a vacuum source can be fluidly connected to trough 112. When the vacuum source is applied to trough 112 as shown in FIG. 16, a suction force will be created in trough 112 drawing pad 111 and the wall of the left ventricle B together.

Figure 17:
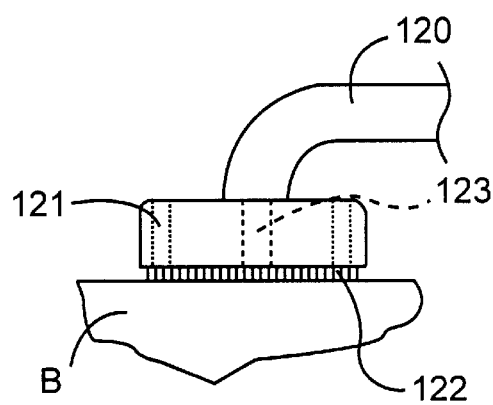
FIG. 17 is a side view of an alternate embodiment of an alignment device pad with stabilizing apparatus.

FIG. 17 is a side view of an alignment device pad 121 disposed at the end of an arm 120 including an alternate stabilization device 122. An aperture 123 for receiving a tension member guide and/or tension member extends through pad 121. Stabilization apparatus 122 is preferably a roughened surface disposed on pad 121 to increase the friction between pad 121 and the external wall surface of left ventricle B. Apparatus 122 could be made from, for example, either the hook or the loop portion of a hook and loop type fastener.

If a tension member guide or tension member is inserted into the heart using alignment device 70, 80 or 100, it is preferable that the pad of the aperture through the pad at the tension member exit point is over sized in comparison to the pad aperture of the alignment device at the tension member entry point. This is because as the tension member guide or tension member passes through the heart, motion of the heart may cause some minor misalignment of the tension member guide or tension member where it exits the heart.

Figure 18:
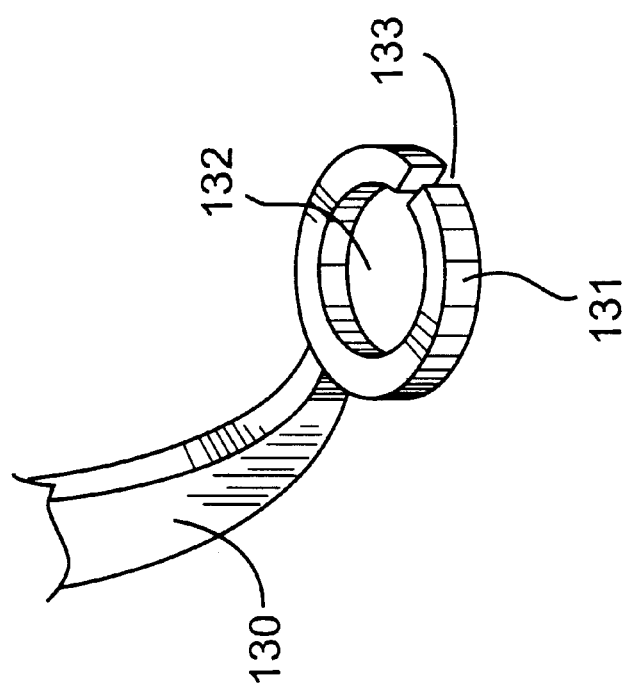
FIG. 18 is a perspective view of an alignment device pad.

FIG. 18 is a perspective view of a pad 131 disposed on the end of an alignment device arm 130. Pad 131 includes an aperture 132 therethrough. This aperture has a diameter preferably between 1.5 and 15 times greater than the aperture to the opposite pad. FIG. 18 also shows a notch 133 through pad 131 which extends from the exterior of the pad into aperture 132. Notch or opening 133 would preferably allow a tension member guide or tension member to be removed transversely from aperture 132 without aperture 132 having to moved over an end of the tension member guide or tension member.

Figure 19:
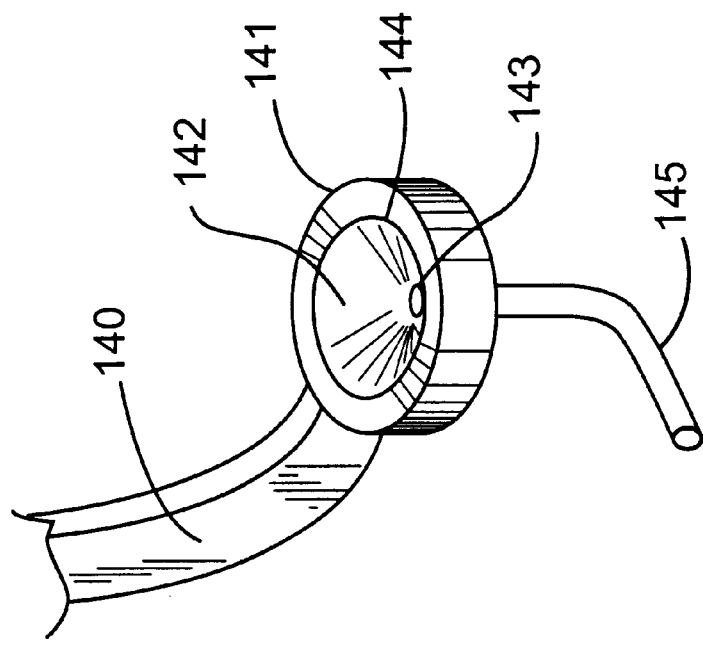
FIG. 19 is a perspective view of an alternate embodiment of an alignment device pad.

FIG. 19 is a perspective view of an alternate embodiment of an alignment device pad 141. Alternate embodiment 141 is disposed at the end of an alignment device arm 140. Pad 141 includes a funnel shape aperture 142. Aperture 142 includes a large diameter end 144 and a small diameter end 143. Large diameter end 144 is preferably disposed adjacent the heart and tension member exit point during use. A guide tube 145 can lead out from smaller diameter end 143 of aperture 142. Guide tube 145 preferably includes a bend passing through an arc of preferably between about 45° to about 135° and more preferably about 90°. The radius of the bend is preferably long enough that devices advanced through guide tube 145 are not permanently bent as a consequence of being advanced through the arc of guide tube 145. The radius of the arc is preferably about 0.05 inches to about 2 inches, and more preferably between about 0.75 inches and, most preferably about 1 inch as measured to the central axis of guide tube 145.

Figure 20:
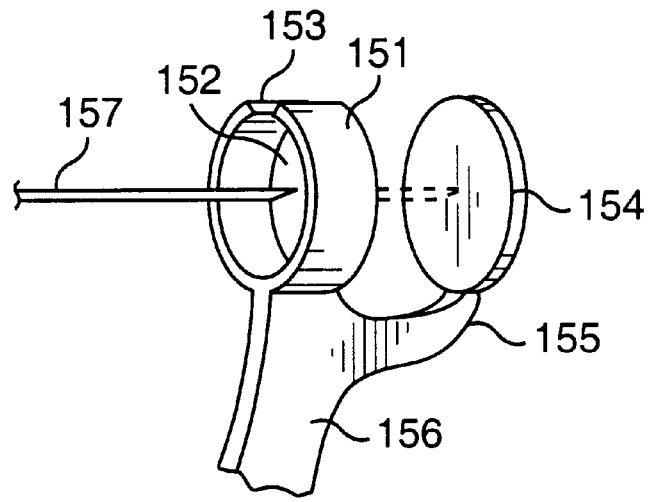
FIG. 20 is yet another alternate embodiment of an alignment device receiving pad.

FIG. 20 is a perspective view of yet another alternate pad embodiment 151. Pad 151 has a similar shape to that of FIG. 18 and is disposed at the end of an alignment device arm 156. Pad 151 has an aperture 152 therethrough and a side notch 153 for transverse removal of a tension member guide and/or tension member. Extending from arm 156 is a stop arm 155 having a tension member guide stop 154 aligned with aperture 156 and spaced from pad 151. In use, stop 154 is disposed on the opposite side of pad 151 from the heart. As a tension member guide 157 is advanced from the heart through aperture 152, advancement of the tip of guide 157 is limited by needle stop 154. Stop 154 thus can limit additional advancement of guide 157 which might injure tissue adjacent to the heart.

Figure 21:
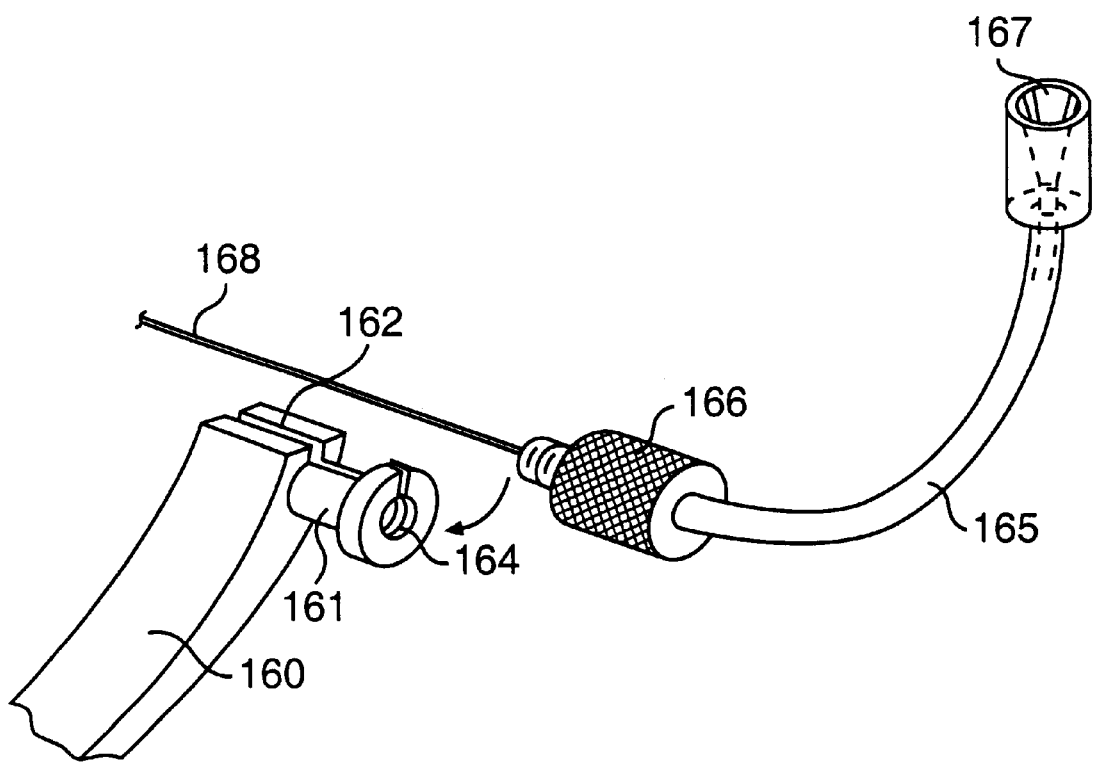
FIG. 21 is a perspective view of an alignment device guide tube.

FIG. 21 is a perspective view of an alignment device guide tube 165. Alignment device guide tube 165 preferably includes a luer lock or similar coupling 166 releasably connectable to a corresponding coupling 161 connected to an alignment device such as 70, 80 or 100 shown above. Coupling 161 of FIG. 21 is shown connected to an alignment branch arm 160. The end of the alignment branch arm 160 opposite coupling 161 preferably includes a heart engaging pad or surface such as those shown in FIGS. 16 and 17. An aperture 169 extends through coupling 161 in the end of arm 160. A transverse aperture or notch extends into aperture 169 such that a tension member guide or tension member can be withdrawn from aperture 169 transversely without moving aperture 169 over the end of the tension member guide or tension member. Guide tube 165 preferably includes a funnel shaped guide tube entry port 167 opposite connector 166. Guide tube 165 preferably includes a bend passing through an arc of preferably between about 45° to about 135° or more preferably about 90°. The radius of the bend is preferably long enough that the devices advanced through guide tube 165 are not permanently bent as a consequence of being advanced through the arc of guide tube 165. The radius of the arc is preferably about 0.25 inches to about 2 inches, and more preferably between about 0.75 inches to about 1.5 inches and, most preferably about 1 inch as measured to the central axis of guide tube 165.

In use, aperture 169 is preferably aligned with the desired entry point for the tension member. Guide tube 165 can be coupled to coupling 161 of the alignment device. If it is difficult to gain access to aperture 169 in order to insert the tension member therethrough because coupling 161 is directed transversely or posteriorly within the patient's chest cavity, guide tube 165 can be adjusted to dispose guide tube entry port 167 generally anteriorly for improved access.

Once alignment device 70, 80 or 100 is in place on the entry/exit points, a tension member guide or the tension member can be advanced through the alignment device transventricularly through the heart. Preferably, a tension member guide is used to advance the tension member transventricularly. It is anticipated, however, that if the tension member were sufficiently rigid that it could be advanced transventricularly without a guide.

FIG. 22 is a side view of a tension member guide 170 including a guide tube 176 and stylet 171. Stylet 171 preferably includes a sharpened distal end 172 for advancement into and from the heart. The proximal end of stylet 171 can include a luer lock or similar type connector. A tube 176 defines an elongate lumen therethrough sized to receive stylet 171 or a tension member. Tube 176 preferably includes a luer fitting at its proximal end 175 opposite its distal end 173.

In use, stylet 171 is advanced through tube 176 as shown by the arrow in FIG. 22. Distal tip 172 of stylet 171 preferably extends distally beyond distal end 173 of tube 176. Stylet 171 and tube 176 can be coupled by fittings 174 and 175. Then with one of the alignment devices 70, 80 or 100 in place, the tension member guide 170, including tube 176 and stylet 171 is advanced either directly through one of the alignment device apertures or by way of a guide tube such as guide tube 165 of FIG. 21. Tension member guide 170 is then advanced through the opposite aperture of the alignment device such as shown in, for example, FIG. 20. The length of tube 176 should be long enough to extend through the heart such that proximal end 175 and distal end 173 are disposed outside of the heart. If the alignment device includes transverse notches or slots such as notch 133 of FIG. 18, the alignment device can be removed transversely from needle 170. Stylet 171 is preferably removed from tube 176. The lumen through tube 176 is now unobstructed, providing a passageway for advancing a tension member therethrough.

The primary function of guide 170 and, in particular, tube 176, is to provide a passageway across the heart. Guide 170 should be flexible and resilient such that guide 170 could be advanced through the bend of, for example, guide tube 165. Yet, to maintain accurate delivery of guide 170, it preferably does not permanently bend when passing through tube 165. Column/buckling strength of tension member guide 170 is preferably sufficiently high such that the needle is not deflected as it engages the heart wall as guide 170 is advanced from the heart.

Tube 176 is preferably made from Nitinol, polyimide, reinforced polyimide or other sufficiently flexible biocompatible material. Tube 176 preferably has an inside diameter of about 0.01 inch to about 0.05 inch and, more preferably between about 0.02 inches to about 0.03 inches. The outside diameter of tube 176 is preferably between about 0.015 inches to about 0.07 inches and more preferably between about 0.02 inches and about 0.05 inches. Stylet 171 is preferably formed from Nitinol, stainless steel or other sufficiently rigid biocompatible material. Stylet 171 preferably has a diameter of between about 0.005 inches and about 0.05 inches and more preferably about 0.26 inches.

FIG. 23 is an alternate embodiment of a tension member guide 180 including a stylet 181 having a handle 184 disposed at its proximal end and a sharpened point 182 disposed at its distal end. Stylet 181 is shown extending through a tube 186 having a proximal end 185 and a distal end 183. Guide 180 is essentially similar to guide 170 of FIG. 22 except that tube 186 and stylet 181 do not include a coupling mechanism.

FIG. 24 shows a distal end of a stylet 190 similar to stylet 171 of FIG. 22. The sharpened tip 191 is shown rounded in comparison to the sharp tip 172 of stylet 171 shown in FIG. 22. Tip 191 is rounded such that it can be advanced through the heart wall without undue pressure or trauma yet be deflected from, i.e., not pierce, chordae within the left ventricle which may be encountered as the guide is being advanced transventricularly. It should be understood that such a tip could be used on stylets of guides 170 or 180 above.

As an alternative to providing a rounded tip for stylets such as tip 191 of stylet 90, a retractable sheath 203 can be placed around a stylet 200 having a sharpened tip 202. In FIG. 25, sheath 203 is shown in a first position retracted away from sharpened tip 202, such that tip 202 is exposed. In FIG. 26, sheath 203 is shown in a second position covering sharpened tip 202. Sheath 203 and stylet 202 are preferably advanced transventricularly in a tube similar to tubes 176 or 186 of tension member guides 170 and 180. Sheath 203 is preferably spring biased into the second position shown in FIG. 26 and moved into the first position as shown in. FIG. 25 only as it is advanced through the heart wall. To bias sheath 203 into the second position, a helical coil spring could be placed around stylet 200 between a proximal end of sheath 203 and the stylet handle.

FIG. 27 is a view of yet another alternate embodiment 210 of a stylet for a tension member guide. Stylet 210 includes a sharpened tip 211 at the distal end of a shaft 214 which defines an inflation lumen therethrough. Tip 211 is sealed such that inflation fluid forced through stylet 214 will exit an orifice 213 disposed within a balloon 212 connected to stylet 210 proximate its distal end.

FIG. 28 is a view of stylet 210 of FIG. 27 wherein balloon 212 has been inflated to cover sharpened tip 211. In use, balloon 212 would be inflated after stylet 214 has been advanced into the left ventricle and deflated prior to being advanced from the heart and ventricle through the heart wall. Stylet 214 preferably is used in conjunction with a guide tube in a manner similar to stylets 171 and 181.

FIG. 29 is yet another alternate embodiment 215 of a tension member guide 215 in accordance with the present invention. Guide 215 is shown including an elongate tube 220 having a distal tip 222 partially advanced through left ventricle B of heart A. FIG. 30 is a view of distal tip 222 of guide 215. By reference to FIG. 30, it can be seen that shaft 222 defines a lumen therethrough in which an optical fiber 224 is disposed.

To guide 215 transventricularly, rather than advancing guide 215 through an alignment device, such as devices 70, 80 or 100, guide 215 is advanced through a first left ventricular wall where a tension member entry point has previously been identified. Light is transmitted axially through the lumen within shaft 220 by optical fiber 224. The light axially exits distal end 222. If the light is sufficiently bright, it should be visible from outside of the heart when guide 215 is being advanced through the left ventricle. If the visible light is directed at a predetermined exit point, marked on the outside of the heart, needle 215 can be advanced through the exit point to outside the heart. Fiber optic 214 can then be removed from the lumen through shaft 212. The lumen can then be used as the passageway for advancement of a tension member therethrough.

FIG. 31 is an alternate embodiment of a tension member guide 230 including an optical fiber 232 disposed around a shaft 231. Shaft 231 is essentially similar shaft 220. Guide 230 can be advanced transventricularly in a manner similar to that described with respect to guide 215 except that optical fiber 232 need not be removed and shaft 231 which defines an elongate lumen extending therethrough.

FIG. 32 is yet another embodiment of a tension member guide 235 having a shaft 236 essentially similar to shaft 220. An optical fiber 237 is disposed parallel to shaft 236 and connected thereto. In addition to the fiber optic guides of FIGS. 29–32, real time guidance of the tension member guide transventricularly can be accomplished by echo imagery or fluoroscopy. The guide in such instances should be echogenic or substantially radiopaque.

The fiber optic guides of FIGS. 29–30 lend themselves particularly well to both open chest and less invasive procedures. When the fiber optic guides are configured for less invasive procedures, the shaft is preferably advanced through the heart through a lateral port and advanced out the opposite side of the heart and body through an oppositely disposed lateral port. Opposite ends of the shaft then preferably extend outside of the body through the oppositely disposed lateral ports.

Figure 33:
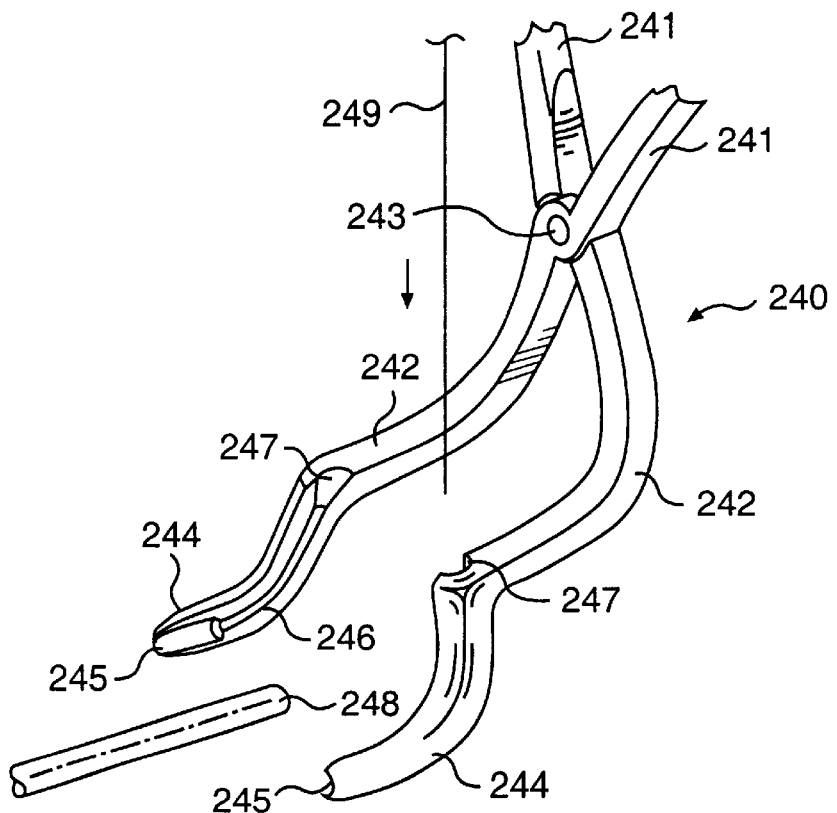
FIG. 33 is a perspective view of a guide clamp.

FIG. 33 is a perspective view of a scissor-like guide clamp 240 which can be used to guide a tension member 249 into the tube 248 of a tension member guide. Device 240 includes scissor-like handles 241. Handles 241 extend to respective arms 242. Each handle 241 and arms 242 form a unit which are pivotable about a pin 243. At an end of arms 242 opposite handles 241, a half conical recess is formed in arm 242. Recess 247 leads to a generally semi-circular cross sectional channel 246 which in turn leads distally to a generally semi-circular cross sectional tube receiving groove at distal end 244 of arm 242.

Figure 34:
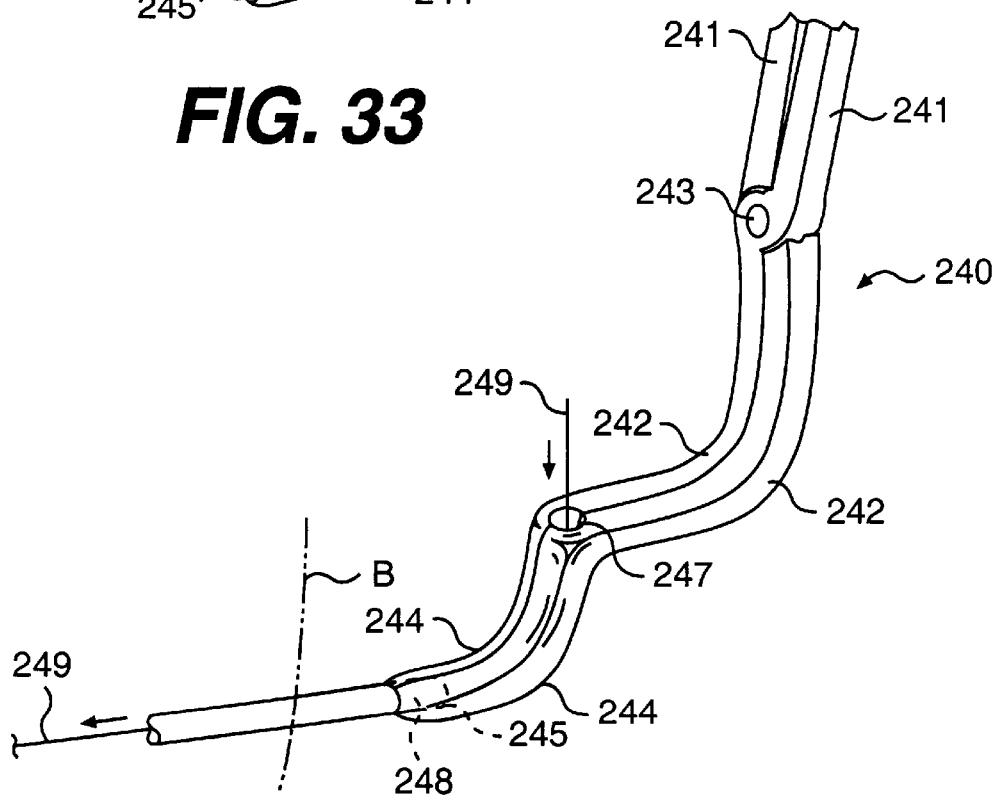
FIG. 34 is a perspective view of a wire guide clamp connected to a delivery tube.

When arms 242 are brought together as shown in FIG. 34, receiving grooves 245 form a receiving aperture to receive an end of tension member guide 248. Recesses 247 form a tension member receiving opening leading to a tube formed by channels 246. A tension member 249 is shown being advanced through tube 248 in the direction of the arrows. Tension member 249 could also be advanced from tube 248 through device 240. Channel 246 preferably includes a bend passing through an arc of between about 45° and 135° and more preferably through about 90°.

Once a tension member guide has been delivery transventricularly, and a passageway is created across the chamber, the tension member is delivered through the passageway. When delivering the tension member, the end of the tension member not being advanced through the passageway preferably has an anchor or anchor pad fixably connected thereto. This eliminates the need to attach the pad later, but it may not be possible in the case where the guide includes a hub such as hub 175 of tube 176 of FIG. 22. In the case of guide 180 where tube 186 does not include a hub, tube 186 can be withdrawn from the heart over the end of the tension member which was advanced transventricularly. In order to remove a tube 176 from a tension member which has been advanced therethrough and has an anchor pad fixably connected to the end of the tension member which was not advanced through tube 176, the tension member should be advanced through tube 176 beginning at distal end 173 such that the end of the tension member not having the anchor pad emerges from the heart at hub 175. Then tube 176 can be removed over the end of the tension member to which a pad has not yet been attached.

Rather than using a tension member guide and/or tension alignment device to align the tension member for delivery through the preselected exit and entry points, tubular members 250 such as those shown in FIG. 35 can be advanced into the left ventricle from oppositely disposed predetermined entry points on the heart wall to form a splint 253'. Members 250 preferably have ends 250' which are sufficiently sharp that members 250 can advance through the heart wall without excessively injuring the wall. Members 250 preferably have anchor pads 252' fixed at their opposite ends 250'. Members 250 preferably have a lumen defined therethrough in fluid communication with a lumen defined through pads 252'.

After members 250 are advanced into the ventricle through the predetermined entrance points, a wire hook 253 is advanced from one member 250 and a wire loop 251 is advanced from the opposite member 250. Hook 253 is then guided into loop 251 either by feel, or by echo imagery or fluoroscopy. Loop 251 preferably has a hook guide 252 to channel hook 253 into the member 250 disposed to the left in FIG. 35, as loop 251 is drawn through that member 250 by pulling ends 251' of loop 251 to the left. Loop 253 is preferably drawn through member 250 disposed to the left in drawing FIG. 35 such that it can be knotted to the left of pad 252' to form a tension member. The knot will restrain hook 253 from being pulled back in the heart. The opposite ends 253' of hook 253 can be knotted to the right of pad 252' disposed to the right in FIG. 35. The knot should be sufficiently large to prevent ends 253' from being pulled into ventricle B.

It can be appreciated that members 250 can be placed as shown without pads 252'. Loop 251 can be placed across left ventricle B to form a tension member as described above. Members 250 can then be withdrawn and pads placed on opposite ends of hook or tension member 23. Alternately, hook 253, once placed across left ventricle B, could be used as a tension member lead by fastening a tension member to one end of hook 253 and drawing the attached tension member across left ventricle B by withdrawing hook 253 from the left ventricle B.

FIG. 36 is an alternate embodiment of a splint 260'. A tension member 255 is advanced into left ventricle B. An anchor pad 255' is shown connected to one end of tension member 255 outside of chamber B. Tension member 255 includes a sharpened end 256 which is advanced through the myocardium. Proximate sharpened tip 256 are a plurality of circumferential grooves 256. To the left in FIG. 36 is a tension member 258' extending into chamber B. Connected to one end of tension member 258' is a anchor pad 257'. Tension member 258' includes an outer tube 257 and inner receiving tube 258. A loop 259 extends to a side of receiving tube 258 and out of the ventricle through a lumen defined between tube 257 and 258. Ends 259' of loop 259 are shown to the left of pad 257'. An end 261 of tube 258 is preferably thin or sharp enough to be advanced through heart wall of chamber B.

Tension members 255 and 258' are advanced into chamber B similarly to tension members 250 of splint 253'. Once tension members 258' and 255 have been advanced into chamber B, end 256' of tension member 255 is advanced into loop 259. This can be accomplished by feel, or echo imaging or fluoroscopy if loop 259 and tension member 255 are echogenic or radiopaque respectively. After tension member 255 is advanced into loop 259, loop 259 is drawn to the left by pulling ends 259' to the left. Tension member loop guide 260 engages with a groove 265 and tension member 255 and end 256' are drawn into receiving tube 258 to unite tension members 258' and 255. Ends 259' are then tied to prevent loop 259 from shifting to the right in FIG. 37.

It can be appreciated that members 255 and 258' can be advanced into left ventricle B while not having pads 255' and 257' attached thereto, respectively. Once members 255 and 258' are placed across left ventricle B and connected as shown in FIG. 37 they can be used as a tension member guide tube such as guide tube 176 of FIG. 22.

Figure 38:
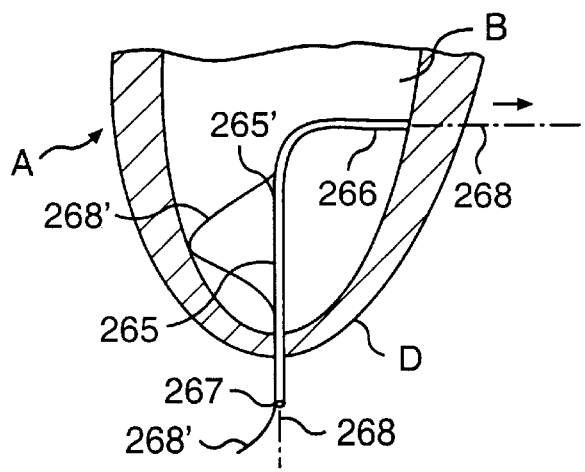
FIG. 38 is a tension member delivery catheter shown in a left ventricle.

FIG. 38 is a vertical cross sectional view of left ventricle B of heart A including apex D showing an alternate device for placing a tension member. A catheter 265 having an elongate shaft 265' is disposed in part within ventricle B. Shaft 265' has a distal end 266 and a transverse bend proximate end 266. Shaft 265' has a proximal end 267. An elongate lumen is defined through shaft 265' between proximal end 267 and distal end 266. Shaft 265' is sufficiently rigid that distal end 266 can be advanced through apex D. A purse string suture is preferably placed on apex D around shaft 265' to control bleeding. Catheter 265 is advanced into ventricle B such that distal tip 266 is brought into contact with the ventricular wall at a location where the tension member will exit chamber B. Catheter 265 preferably include a retractable brace wire 268' having a distal end fixably connected to shaft 265 proximate the transverse bend. Brace wire 268' extends proximally outside of shaft 265' to an orifice where it enters shaft 265. Wire 268' then extends within shaft 265' proximal to the proximal end of shaft 265'. When advancing catheter 265 into ventricle B, wire 268' can be pulled proximally drawing wire 268' parallel and adjacent to shaft 265'. Once catheter 265 is disposed within ventricle B, wire 268' can be shifted distally to bow transversely and brace catheter 265 against a ventricular wall opposite distal end 266.

Distal tip 266 preferably includes a radiopaque marker such as that shown in FIG. 10, so that tip 266 can be viewed by fluoroscopy or an echo marker for echo visualization. The radiopaque or echo marker can be used to locate the tension member exit points. Once a tension member exit point is determined, a tension member 268 can be advanced through the lumen of catheter 265. The tension member should be sufficiently rigid and have a distal end sufficiently narrow or sharpened that it can be advanced through the ventricular wall. After tension member 268 is passed through the ventricular wall, catheter 265 is removed from ventricle B and wire 268. Catheter 265 is then reinserted into left ventricle B through apex D along side tension member 268.

Figure 39:
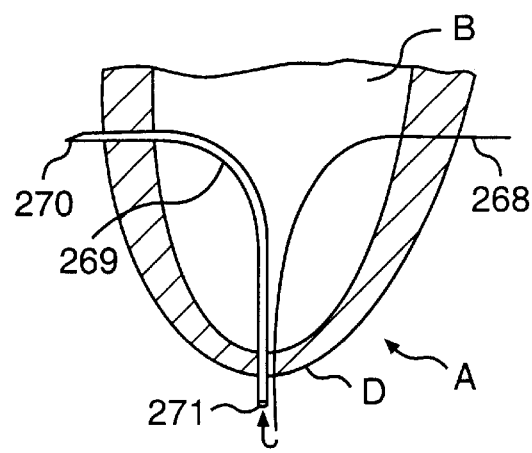
FIG. 39 is a view of a hypotube placed in the left ventricle using the catheter of FIG. 38.

The location of a second tension member exit point is determined, this time rather than advancing a tension member through the lumen of catheter 265, a hypotube 269 having a distal tip 270 and shown in FIG. 39, is advanced through catheter 265. Distal tip 270 passes through the heart wall at the location of the second tension member exit point. Tube 269 need not be a hypotube but could be another tube having sufficient pushability to be advanced through the heart wall at the second tension member exit point. Distal tip 270 should be narrow enough or sufficiently sharpened to traverse the heart wall. A proximal end of hypotube 268 should remain outside the heart and proximal apex D. In FIG. 39, catheter 265 has been removed proximally from hypotube 269 as it was from tension member 268. After hypotube 269 has been placed as shown in FIG. 39, the proximal end of tension member 268 is advanced into proximal end 271 of hypotube 269. The proximal end of tension member 268 is advanced through hypotube 269 until it exits chamber B by way of the distal end 270 of hypotube 269.

Figure 40:
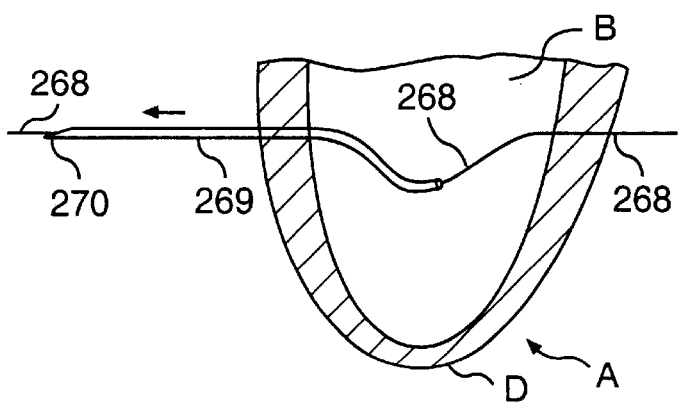
FIG. 40 is a view of the hypotube of FIG. 39 being removed from the left ventricle.

In FIG. 40, tension member 268 is shown extending from distal end 270 of hypotube 269. Hypotube 269 is shown being withdrawn in the direction of the arrow over tension member 268. After hypotube 269 is withdrawn, the tension member 268 is then in place across ventricle B It can appreciated that tension member 268 has been placed without an alignment device such as alignment devices 70, 80 or 100. Anchors or anchor pads can be placed on the tension member on opposite sides of the heart and adjusted as described in more detail below. The remainder of the steps necessary to complete the placement of the transventricular splint will be discussed in detail below.

Figure 41:
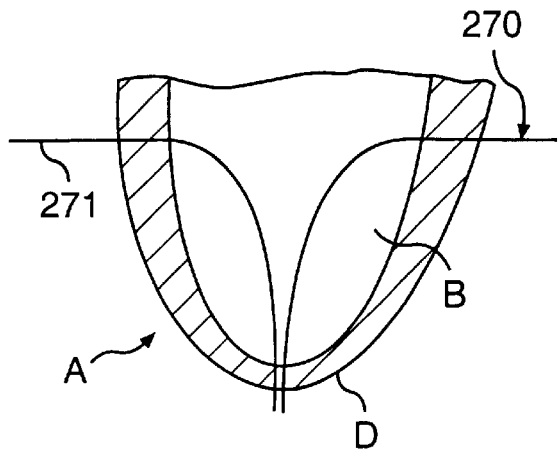
FIG. 41 is a view of two guide members placed in the left ventricle using the catheter of FIG. 38.

FIG. 41 is a vertical cross section of left ventricle B of heart A including apex D showing an alternate method of placing a tension member. Two guide members 270 and 271 are shown advanced through apex D and out opposite sides of chamber B. Guide members 270 and 271 have been placed in this position in a manner similar to the way that tension member 268 was placed as shown in FIG. 39.

Figure 42:
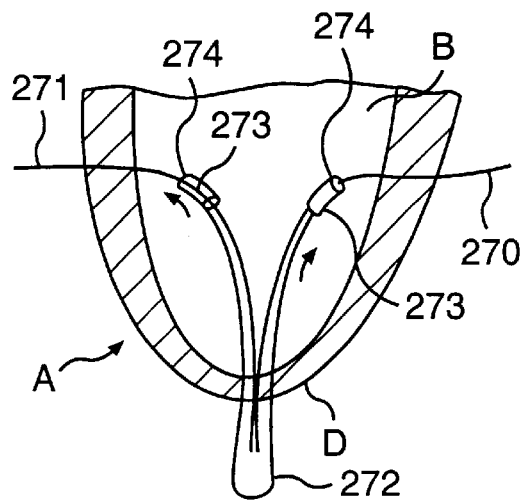
FIG. 42 is a view of a tension member being advanced over the guide members of FIG. 41.

FIG. 42 is a view of a tension member 272 including guide tubes 273 disposed at each of its ends. Guide tubes 273 have distal ends 274 which must be sufficiently narrow or sharpened to penetrate the ventricular walls. Guide tubes 273 as shown, have been advanced through apex D over guide members 270 and 271. Tension member 272 must be sufficiently rigid to provide sufficient pushability to advance guide tubes 273 through apex D over guidewires 270 and 271 and through the ventricular walls. Once guide tubes 273 have been advanced through oppositely disposed ventricular walls, tension member 272 can be pulled taunt across ventricle B. Once tension member 272 is drawn across ventricle B, anchors can be disposed on tension member 272 on opposite sides of heart A as described in more detail below.

Figure 43:
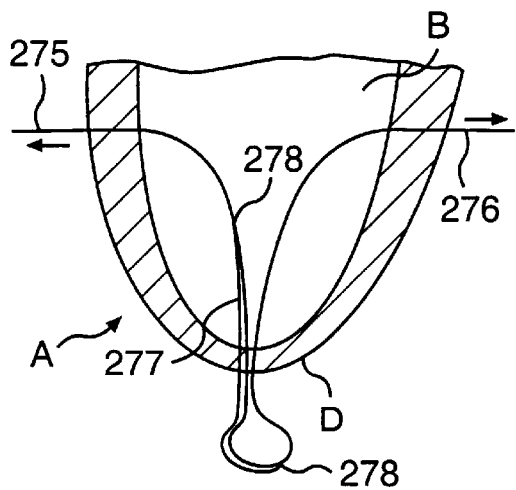
FIG. 43 is a view of a tension member and leads placed in a left ventricle using the catheter of FIG. 38.

FIG. 43 is a vertical cross section of left ventricle B of heart A including apex D. As shown in FIG. 43, leads 275 and 276 have been advanced through apex D and opposite ventricular walls in a manner similar to guidewires 270 and 271 as shown in FIG. 41. Connected to leads 275 and 276 by connectors 278 is a tension member 277. This arrangement may be used in a situation wherein tension member 277 is substantially less pushable or rigid than leads 275 and 276. Leads 275 and 276 must first be placed in a manner similar to guide members 270 and 271 of FIG. 41, such that the ends of leads 275 and 276 extend through the side walls of ventricle B and apex D. Then the relatively flexible tension member can be drawn into ventricle B. As shown in FIG. 43, tension member 277 is partially drawn into ventricle B. Ultimately leads 275 and 276 are drawn in opposite directions until tension member 277 extends transventricularly across ventricle B and passes through the ventricular wall to the exterior of heart A. Once tension member 277 is disposed on opposite sides of the heart, anchors or pads can be attached to opposite ends of the tension member to form the transventricular splint. The splint can be adjusted as described in more detail below.

Figure 44:
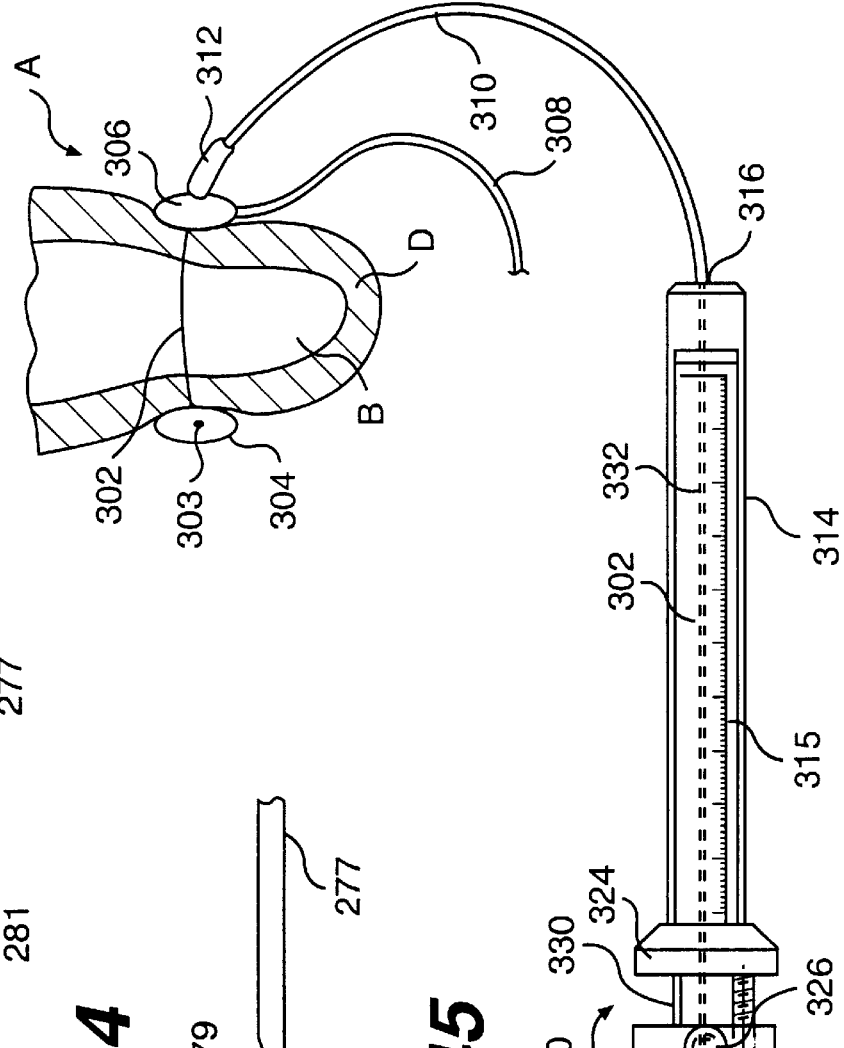
FIG. 44 is a view of a connector for connecting the lead and tension member of FIG. 43.
Figure 45:
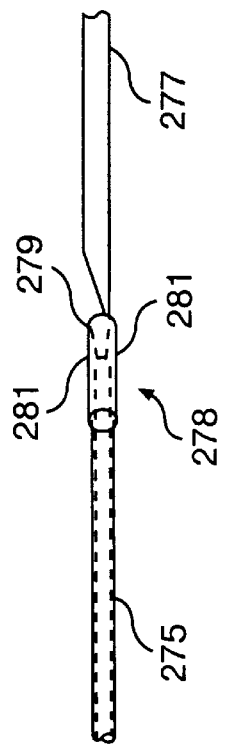
FIG. 45 is a view of the connector of FIG. 44 connecting a lead and tension member.

FIG. 44 is a view of connector 278 of FIG. 43. Lead 275 includes a loop 280 disposed at one end. Tension member 277 includes a hook 279 disposed at one end. A locking tube 281 is slidably disposed over a portion of hook 279. To complete the connection between lead 275 and tension member 277, hook 279 is hooked to loop 280. Hook 279 is then collapsed such that hook lock 281 can be slid over the collapsed portion of hook 279 to retain loop 280 in place on hook 279 as shown in FIG. 45.

The tools and methods shown and described with respect to FIGS. 38–43 lend themselves both to open chest and less invasive implantation procedures. They are particularly suited to less invasive procedures where the apex of the heart is accessed through an anterior port and the ventricular walls are accessed through oppositely disposed lateral ports such that opposite ends of the tension member can extend into oppositely disposed lateral ports. Rather than gaining access through the apex, those tools shown in FIGS. 38–43 gaining access the left ventricle through the apex could instead access to the left ventricle through the aortic valve or mitral valve. Access through the aortic valve is preferably obtained through the aorta by way of either a carotid or femoral artery access point. Access to the mitral valve can be obtained by way of a port, window or the like and may be a particularly desirable route if mitral valve replacement or repair is done in conjunction with splint implantation.

With respect to those tension members placed ventricularly through tension member guides as described above, it was indicated that it is preferable to connect an anchor or anchor pad to the end of the tension member not being advanced through the guide tube prior to advancing the tension member through the guide tube. It is not necessary to connect the pad to the tension member at that time, however. In the case of those embodiments where the tension member is advanced into the ventricle from opposite sides as shown in FIGS. 35–37, it is preferable that the anchors or anchor pads are connected to the tension members prior to advancement of the tension members into the ventricle. Here again, having the anchors connected to the tension members at this time is not required, however. With respect to those methods and tools shown in FIGS. 38–43, the pads are preferably placed on opposite ends of the tension member after the tension member is disposed transventricularly and both ends of the tension member are exposed outside of the heart.

Once the pads or anchors are disposed on the tension member, the length of the tension member disposed between the pads is preferably adjusted. This adjustment is preferably made by fixing the position of one of the pads on the tension member and allowing the other pad to slide along the tension member. With respect to the splints of FIGS. 35–37, however, both pads can be affixed to the respective tension members prior to adjusting the overall length of the splint (by placement of the knots as described above). The pad which is fixed to the tension member is drawn into engagement with the external wall of the heart by pulling on the end of the tension member opposite the fixed pad. Then the other pad is brought into engagement with the external wall of the heart by sliding it along the tension member toward the pad which is fixed on the tension member. The pads can be placed on opposite ends of the tension member by way of left lateral and right lateral ports to perform the transventricular splint implant less invasively.

The effective length of the tension member, i.e., the distance between the pads measured along the tension member, can be correlated with the magnitude of heart wall stress reduction. For an idealized calculation of this relationship, please see U.S. patent application Ser. No. 08/933,456, filed Sep. 18, 1997, and incorporated herein by reference. It is also anticipated that the force exerted axially along the tension member by the heart engaging the pads can also be correlated with heart wall stress reduction.

Figure 46:
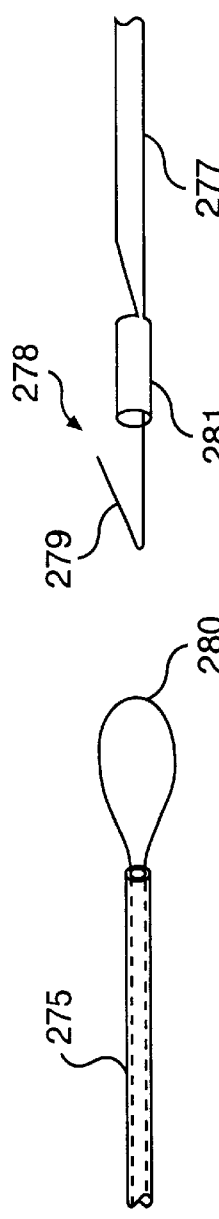
FIG. 46 is a view of the tension member measuring and tightening device.

FIG. 46 is a view of a measuring device 300 through which a tension member 302 has been threaded. One end of tension member 302 extends through left ventricle B of heart A. An anchor pad 304 has been fixedly attached to tension member 302 and end 303 and drawn into engagement with heart A. The second pad 306 has been placed on tension member 302 but has not been tightened, i.e., fixedly attached to tension member 302. Pad 306 is free to slide along tension member 302. Extending from anchor pad 306 is a tether or string 308. In general, it may be desirable to attach a tether to the anchor pads as shown herein. This would make them easier to retrieve if they were dropped within the chest cavity during a splint implantation procedure.

Measuring device 300 includes an elongate tension member receiving tube 310 having a distal end including a pad engagement member 312 and a proximal end 316 connected to a preferably clear measuring tube 314 having a measuring scale 315 marked thereon. Tension member 302 has been threaded through tube 310 and tube 314. Tension member 302 has also been threaded through a tube 318 having a retaining block 319 and a screw 320 at one end tightened to releasably hold tension member 302. Screw 320 is preferably connected to a force transducer. Another block 322 is disposed at the opposite end of tube 318. A screw 326 extends into block 322 to releasably hold guidewire 302. Block 322 is disposed adjacent block 324 connected to tube 314. Interconnecting block 322 and 324 is a guide rail 330 and adjustment screw 328. Adjustment screw 328 can be rotated to move screw and block 320, tube 318, block 322, screw 326, and thus tension member 302 through tube 314.

Tension member 302 preferably has a visible index mark 332 placed along its length a known distance from end 303 of tension member 302. Measuring tube 314 preferably magnifies mark 332. The length of tube 310 and pad engaging member 312 as well as tube 314 should also be known and correlated to scales 315 such that by determining the location of mark 332 relative to scale 315, the length of tension member disposed between pads 304 and 306 can be determined. Set screw 328 can be adjusted until the desired length of tension member 302 between pads 304 and 306 is achieved. Then pad 306 can be fixed in place along tension member 302. Tether 308 is preferably removed. It can be appreciated that tube 310 can be sufficiently long to be advanced through a port for adjusting the length of tension member 302 less invasively.

The distance between pads 304 and 306 is preferably related to the radius $R_1$ of the unsplinted left ventricle. For purposes of this explanation, $2R_1$ can be viewed as the length of the tension member between pads 34 and 36 at end diastole where the pads are spaced such that no shape change is induced by the splint. When pads 306 and 304 are fixed along tension member 302 the distance along the tension member between the pads can be considered l. It can be appreciated that if l were greater than $2R_1$ no shape change to the left ventricle would be induced throughout the cardiac cycle. At the opposite extreme, l could be so short that the opposite walls of the left ventricle are held or pressed together between pads 304 and 306 throughout the cardiac cycle. Preferably, however, the ratio $l/2R_1$ is preferably between about 0.4 to about 0.8 and more preferably between about 0.5 to about 0.7 and most preferably about 0.6.

In addition to measuring the length of tension member 302 between pads 304 and 306 to determine their desired spacing, it is anticipated that device 300 can be used to measure axial force on the tension member as pad 306 is engaged against heart A and advanced toward 304 along tension member 302. To accomplish this, in the preferred embodiment, the device 300 also includes a force transducer 334 and pin vice 336. Pin vice 336 can be tightened to fixably hold tension member 302. If screws 320 and 326 are loosened such that only pin vice 336 retains tension member 302 from sliding distally within the device 300, the distally directed force in tension 302 will be transferred by pin vice 336 to force transducer 334. The axial force detected by the transducer can be observed by calibrating the transducer or connecting it to a monitor in a manner known to those skilled in the art of force transducers. Set screw 328 can be adjusted until the desired force is obtained. The surface of the pad itself could also be centered to create pores for tissue ingrowth. When the desired force level is achieved, pad 306 could be fixed in place along tension member 302.

With respect to any of the transventricular splints disclosed herein, the length of the tension member can be adjusted to form a full cycle splint or restrictive splint. If the length of the tension member is such that the anchors or anchor pads engage the heart to create a shape change throughout the cardiac cycle, the splint created is a full cycle splint. If the anchor or anchor pads do not engage at end systole to create a shape change, the splint formed is a restrictive splint.

Figure 47:
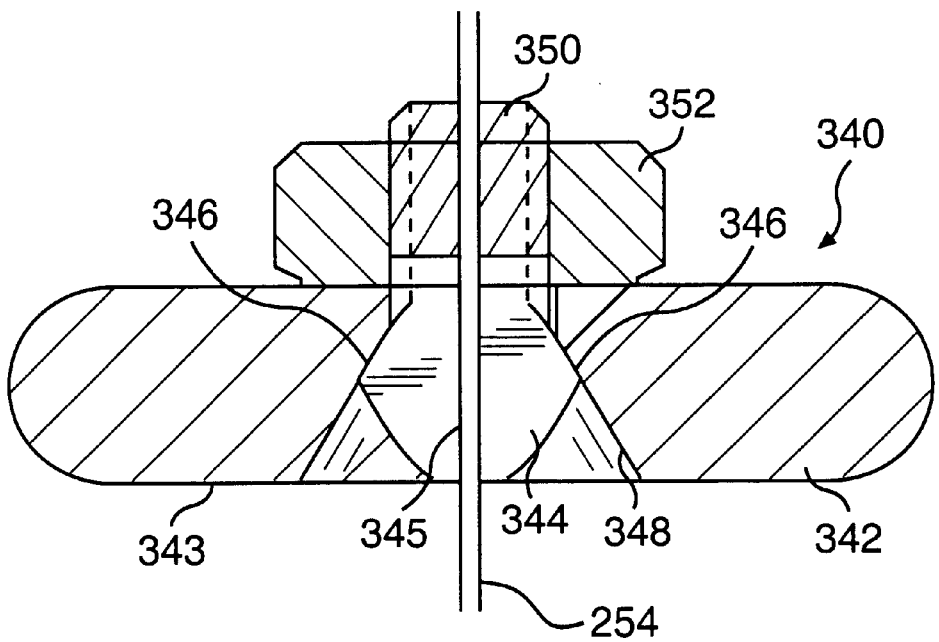
FIG. 47 is a cross sectional view of an anchor pad.

FIG. 47 is a cross sectional view of an embodiment of anchor pad 340 in accordance with the present invention. Anchor pad 340 preferably includes a disc shaped pad portion 342. Disc shape pad portion 342 includes side 343, which in use is disposed toward the heart. A conical aperture 348 having sloping sides 346 extends through pad 342. Collet 344 is disposed within orifice 348. A threaded portion 350 of collet 344 extends from orifice 348 opposite side 343, nut 352 is threaded over threaded portion 350. Lumen 345 extends through collet 344. A tension member 354 is shown extending through lumen 345. Lumen 345 has a diameter such that when nut 352 is not tightened on threaded portion 350, tension member 354 can slide freely through lumen 345. When nut 352 is tightened, it draws collet 344 away from side 343. Collet 344 is then pinched between walls 346 of orifice 348. When collet 344 is pinched, the size of lumen 345 is reduced such that tension member 354 can no longer move freely within lumen 345, fixing the position of pad 340 on tension member 354.

Figure 48:
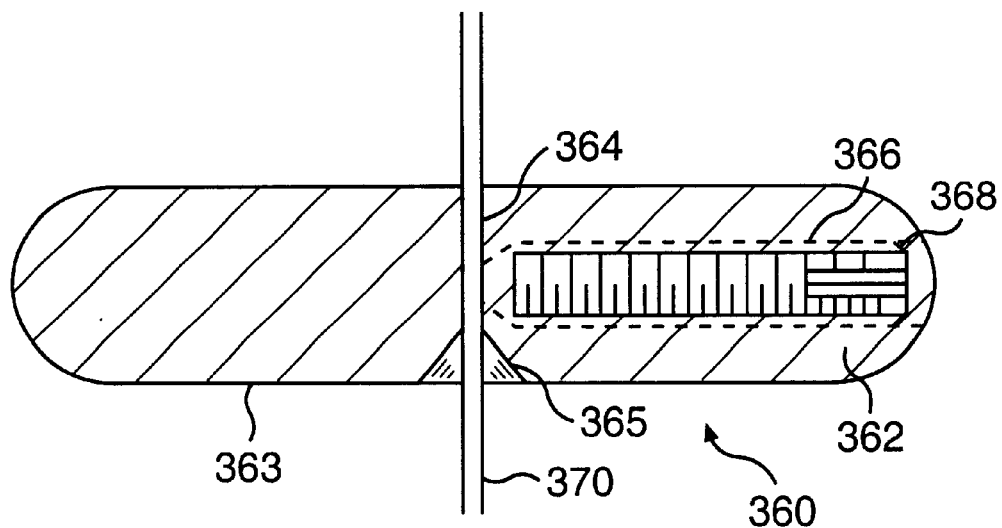
FIG. 48 is a cross sectional view of an alternate anchor pad.

FIG. 48 is a cross sectional view of an alternate embodiment an anchor pad 360 in accordance with the present invention. Anchor pad 360 includes a generally disc-shaped pad portion 362. Pad 362 includes a side 363 which when the pad is in use, is disposed toward the heart. A tension member lumen 364 extends through pad 362. Lumen 364 preferably has a generally conical shaped portion 365 disposed toward side 363. Tension member 370 is shown disposed through lumen 364 in FIG. 48. Pad 362 includes a threaded passage 366 extending from an edge of pad 362 to lumen 364. A set screw 368 is threaded into passage 366. Set screw 368 can be tightened to engage tension member 370 to fix the position of anchor pad 360. When set screw 368 is not tightened, the size of lumen 364 is preferably large enough that anchor pad 360 can slide relatively freely over tension member 370.

Figure 49:
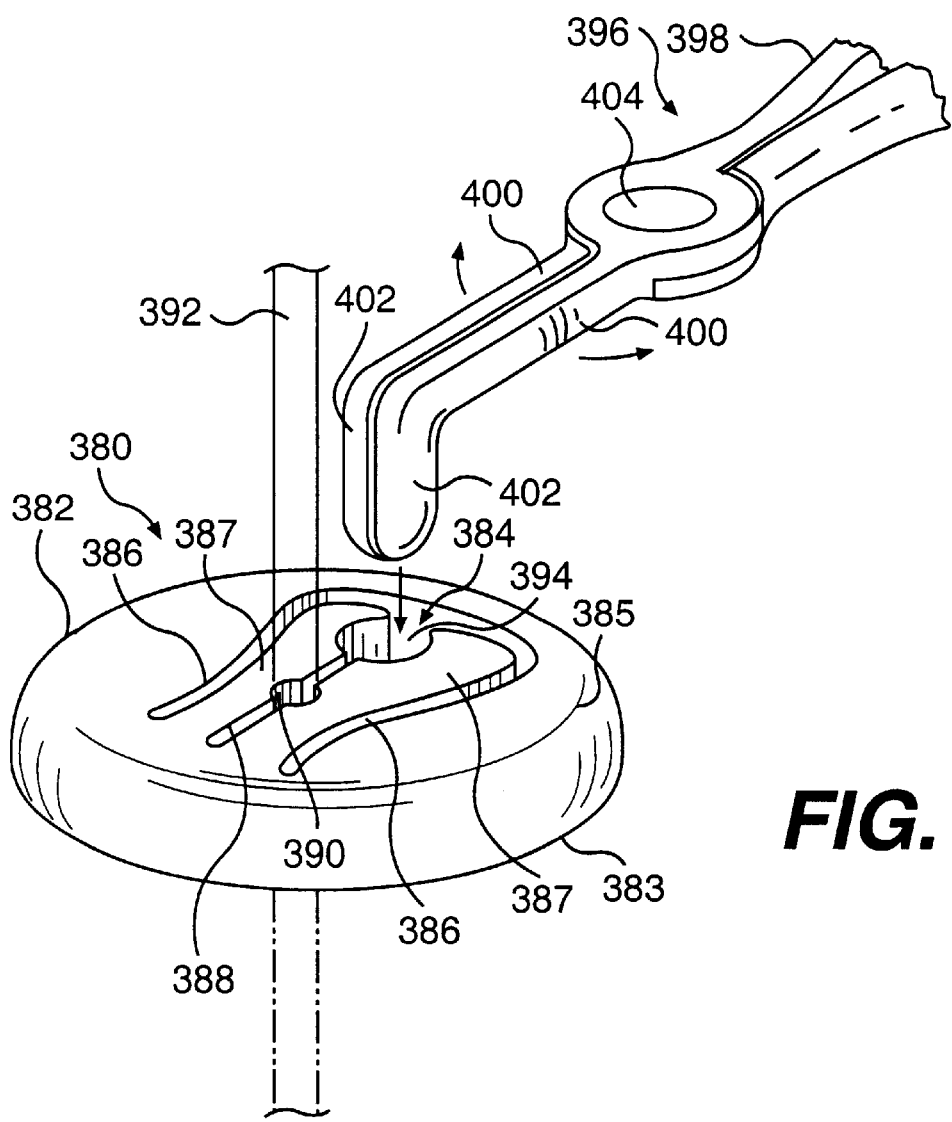
FIG. 49 is a perspective view of yet another alternate embodiment of an anchor pad including an anchor pad loosening device.

FIG. 49 is a perspective view of yet another embodiment of anchor pad 380 in accordance with the present invention. Anchor pad 380 preferably includes a generally disc-shaped pad portion 382 having a first side 383 which in use would be disposed toward the heart and a second side 385. Pad 382 as well as pads 342 and 362 are preferably formed from a metal such as stainless steel alloys or titanium alloys.

A tension member fastener 384 is formed in pad 382 by cutting a series of grooves and apertures through pad 382 from side 385 to side 383. A first groove 386 has a generally horseshoe shape. Second groove 388 extends between opposite portions of horseshoe shaped groove 386 to form two oppositely disposed cantilever members 387. A relatively large aperture 394 is formed between cantilever members 387 proximate their free ends. A second and smaller aperture 390 is formed closer to the fixed ends of cantilever members 387. Tension member 392 is shown extending through aperture 390.

As shown in FIG. 49, tension member 392 is clamped between cantilever members 387 such that the location of pad 382 is fixed along tension member 392. Pad 382 can be released by using a spreading device 396 to spread cantilever members 387 apart. Spreading device 396 includes handle 398 to spreading arms 400 each having a finger 402. Fingers 402 can be placed within aperture 394 then arms 400 and fingers 402 can be spread apart by pivoting them around a pin 404 such that cantilevers 387 are spread apart and pad 382 can move freely along tension member 392. It can be appreciated that although spreader 396 is shown extending transversely from tension member 392, it could also be configured such that fingers 402 do not curve transversely from arms 400 and thus spreader 396 could be disposed parallel to tension member 392. This would be particularly desirable in a situation where anchor pad 380 was being placed through a port or window during a less invasive splint implantation procedure. It can be appreciated that cantilever members 387 can be held apart such that pad 380 can be moved along tension member 392 by placement of a temporary wedge or pin in groove 388. For example, grooves 388 may include an additional small aperture disposed between aperture 390 and aperture 394 into which a pin could be placed to hold open members 387. When it is desired to fix the position of anchor pad 380 on tension member 392, device 396 could be used to spread cantilever members 387 to remove the pin. The cantilever members could then be released to engage tension member 392. Aperture 390 of pad 380 can also include a conical portion disposed toward side 383 such as conical portion 365 of pad 360.

Cantilever arms 384 are preferably configured such that they do not stress tension member 392 beyond its elastic limit. It can also be appreciated that the force developed by cantilever members 387 impinging on tension member 392 is operator independent and defined by the geometry and material characteristics of members 387.

Figure 50:
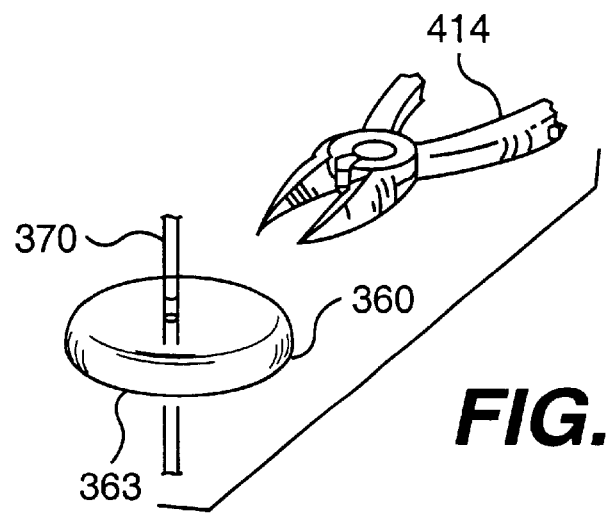
FIG. 50 is a perspective view of a tension member clip.

FIG. 50 is a perspective view of an anchor pad 360 having a tension member 370 extending therethrough. After pad 360 is secured to tension member 370, that portion of tension member 370 which extends from the side of anchor pad 360 opposite side 363 is preferably removed. This can be accomplished by trimming tension member 370 with wire cutter 414 or scissors. Although anchor pad 360 is used here to illustrate trimming tension member 370, it can be appreciated that in each of the embodiments disclosed herein there may be an excess portion of tension member extending from an anchor, which is preferably removed or trimmed.

Figure 51:
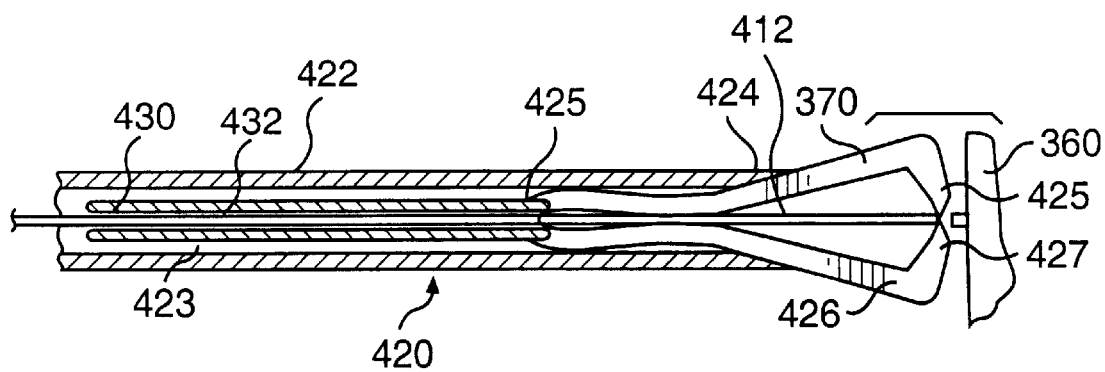
FIG. 51 is a cross sectional view of an alternate embodiment of the tension member clip.

FIG. 51 is a cross sectional view of an alternate embodiment 420 of a tension member cutter. Device 420 includes an elongate outer tube 422 having a distal end 424. Tube 424 defines a lumen 423 through which extends a second tube 430 having a distal end 428. Extending distally from distal end 428 are two cutting arms 424 and 426 which are shown partially withdrawn into lumen 423 and transversely restrained by distal end 424 of outer tube 422. When unrestrained by distal end 424, arms 424 and 426 are biased apart. Each arm 424 and 426 has a cutting element 425 and 427, respectively. Elements 425 and 427 are shown in contact with each other in FIG. 51. A tension member 370 extends between arms 424 and through lumen 432 of inner tube 430. A representative anchor pad 360 is disposed adjacent elements 425 and 427. Device 420 of FIG. 51 is particularly useful when trimming excess tension member using less invasive techniques as it can be readily advanced over a tension member through a port or window.

Figure 52:
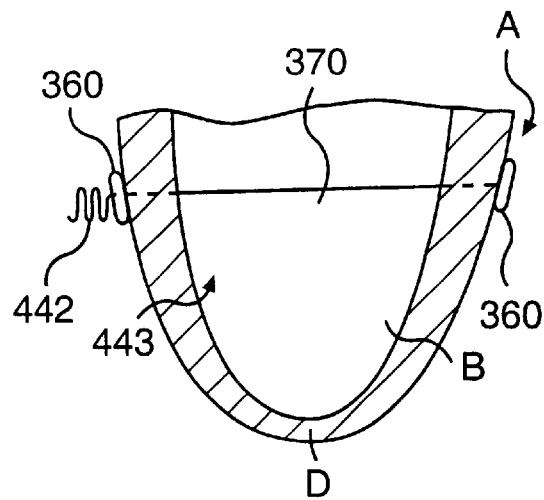
FIG. 52 is a cross sectional view of a heart including a tension member having a heat set end.

FIG. 52 is a vertical cross sectional view of left ventricle B of heart A. A transventricular splint 443 including a tension member 370 and anchor pads 360 are shown disposed on heart A. To the left of heart A as shown in the figure is a coiled portion 442 of tension member 470. As an alternative to trimming an excess length of tension member, tension member 370 could be formed from a shape memory alloy such that portion 442 could be preset to assume a coil shape when warmed to near body temperature.

Once the length of the tension member has been adjusted, the anchors are secured in place along the tension member and the excess length of tension member removed if desired, the anchor or anchor pads are preferably secured in place on the heart. The anchor or anchor pads are secured such that relatively movement between the anchors or anchor pads and the heart is limited to reduce abrasion of the heart wall. To secure the anchor or anchor pads to heart A, a biocompatible adhesive could be placed between the pad and the heart to adhere the pad to the heart. Alternately, apertures could be provided in the pad such that sutures could be extended through the apertures and into the heart to secure the pad. In addition to sutures, the pad could include threaded apertures into which anchor screws could be advanced through the pad and into the heart wall to secure the pad to the heart.

Figure 53:
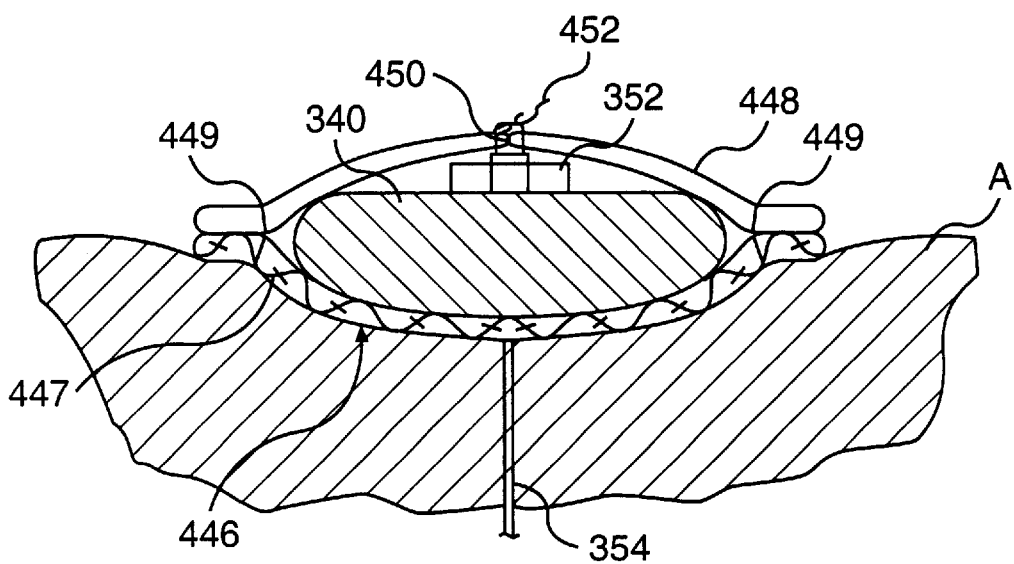
FIG. 53 is a cross sectional view of a pad including an anchor envelope.

FIG. 53 illustrates yet another alternative approach to securing the anchors or anchor pads to the heart surface. FIG. 53 is a cross sectional view of an anchor pad 340 disposed on heart A. Anchor pad 340 is disposed within an envelope 446. Envelope 446 includes a bottom layer 447 disposed between anchor pad 340 and heart A and a top layer 448 disposed on the opposite side of anchor pad 340. Layers 347 and 340 are held together by sutures 449. Bottom layer 447 is preferably a mesh dacron or expanded PTFE which has a pore size or intranodial dimension sufficient to promote tissue ingrowth. The pore size is preferably between about 10 and about 100 microns and more preferably, between about 20 and about 40 microns. With respect to expanded PTFE, the intranodial dimension is preferably between about 10 to about 100 microns and more preferably between about 20 to about 40 microns. The top material could also be dacron or expanded PTFE or the like having a pore size which preferably does not promote ingrowth and thus resists adhesion to surrounding tissue.

Figure 54:
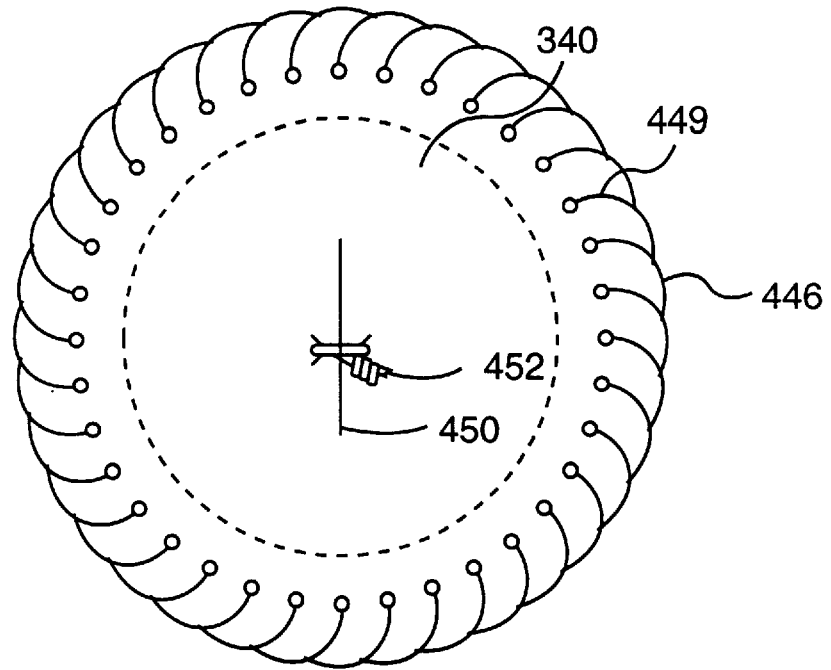
FIG. 54 shows the envelope of FIG. 53.

Envelope 446 would preferably be placed around pad 340 prior to placing pad 340 on tension member 354. A window 450 can be provided to provide access to nut 352 to secure pads to tension member 354. After tightening nut 352, window 450 can be closed by suture 452. FIG. 54 is a top view of pad 340 and envelope 446 of FIG. 53. It can be appreciated that a similar envelope can be placed around the various anchor pads disclosed herein. The location of the window may have to vary, however, to provide access to the respective means for securing the anchor pads to the tension member.

Figure 55:
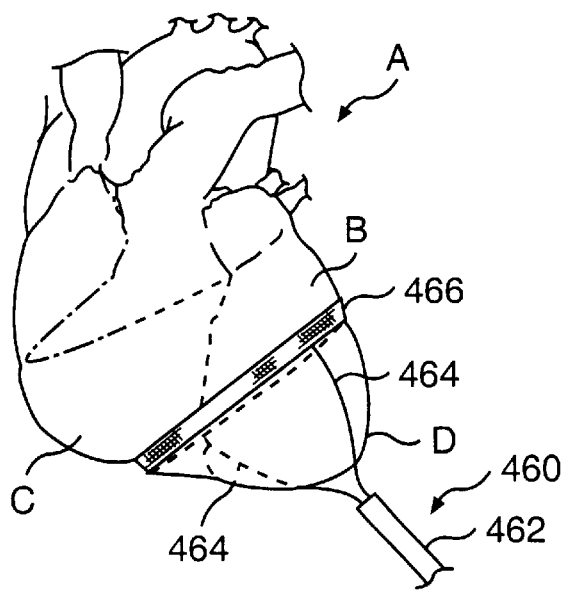
FIG. 55 is a view of a heart including a external locating device.

FIG. 55 shows an alternate embodiment of a splint locating device 460 disposed on heart A. It can be appreciated, however, that alternate locating device such as that shown in FIGS. 13–15 could also be used. Heart A includes left ventricle B, right ventricle C and apex D. Splint locating device 460 which is particularly useful in performing less invasive procedures. Device 460 can be advanced through an anterior port or window to apex D and onto heart A as shown in FIG. 55. Device 460 includes an elongate catheter shaft 462 having a lumen extending therethrough. Extended from the distal end of catheter shaft 462, are two arms 464 preferably biased to spread apart from each other when advanced distally from catheter shaft 462. Connected to the distal end of wires 464 is a band 466. Band 466 preferably readily elongates, i.e., increases in diameter as it is advanced onto heart A, such that band 466 does not substantially alter the pumping performance of heart A.

Figure 56:
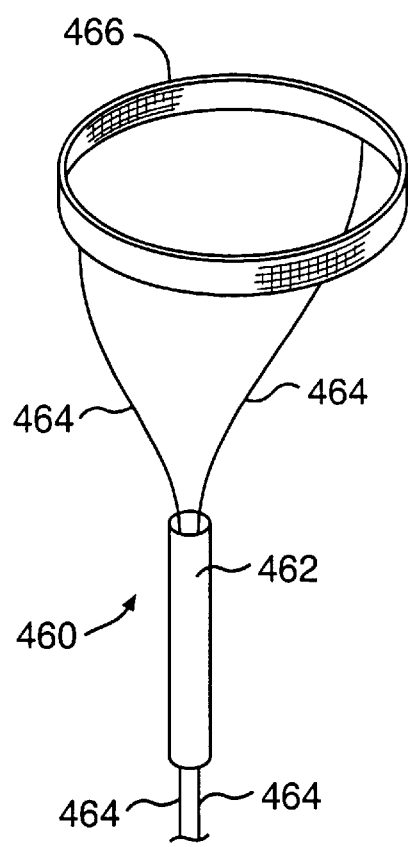
FIG. 56 is a perspective view of the external locating device of FIG. 55.

FIG. 56 is a view of the device 460 disposed on heart A. Wires 464 are shown extending from catheter shaft 462 distally to band 466 and proximally from catheter shaft 462. Prior to advancing catheter 460 through a port or window to apex D, wires 464 are preferably pulled proximally into shaft 462. Band 466 can also be folded and pulled into shaft 462 or folded and disposed parallel to shaft 462 for advancement through the port or window. Once the distal end of shaft 462 is advanced to apex D of heart A, wires 464 can be shifted distally to deploy band 466 and the adjacent portions of wires 464 in heart A.

Figure 57:
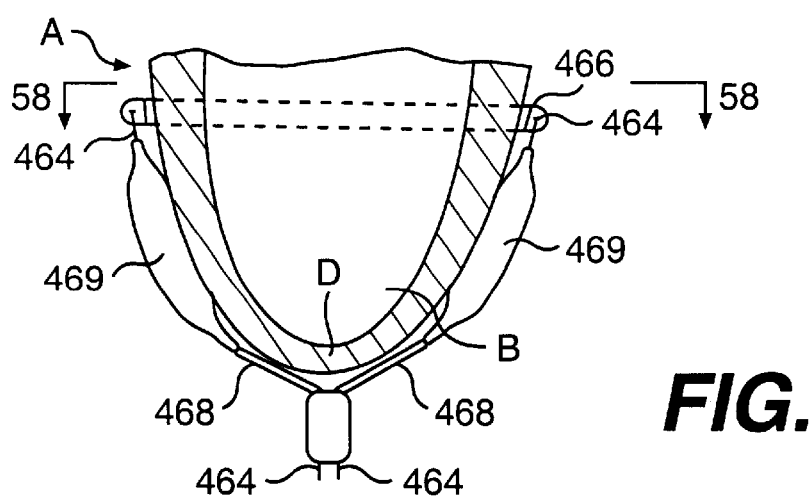
FIG. 57 is a cross sectional view of the locating device of FIG. 55 including inflated locating balloons.

FIG. 57 is a generally vertical cross sectional view of left ventricle B of heart A including apex D. Catheter 460 is shown deployed on heart A. Band 466 has been advanced sufficiently high on heart A such that the adjacent portions of wires 464 will lie proximate potential entry/exit points for the tension member guide or tension member. As can be seen in FIG. 57, two balloon catheters 468 have been advanced over wires 464. Those skilled in the art will recognize that catheters 468 could be configured similarly to an over-the-wire or rapid exchange angioplasty catheter. Balloon catheters 468 include a distally disposed balloon 469 which would be larger than angioplasty balloons, however.

Figure 58:
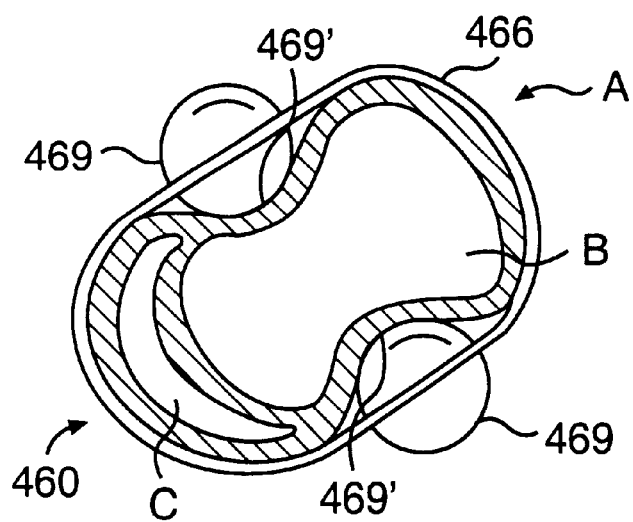
FIG. 58 is a transverse cross section of FIG. 57.

FIG. 58 is a transverse cross sectional view of chamber B and catheter 460 taken from FIG. 57. Balloons 469 have been inflated to induce a shape change in chamber B similar to that shown in FIG. 1A. Balloons 469 can be inflated with a radiopaque or echogenic inflation fluid such that they can be visualized by fluoroscope or echo imagery. If the balloons are imaged in this way, a portion 469' of each balloon 469 engages heart A can be considered as a location for the exit/entry points for the tension member. The criteria for evaluating the location is similar to that described above with respect to the locators of FIGS. 3–12 above. Device 460 can also be used acutely as a temporary splint.

Figure 59:
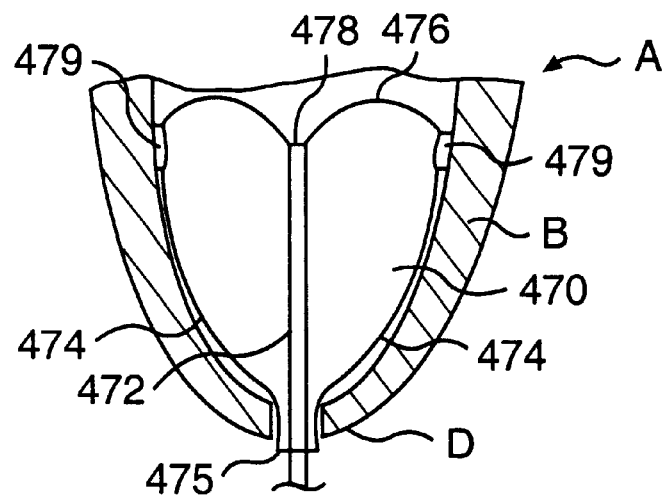
FIG. 59 is a vertical cross section of the heart including an internal locating device.

FIG. 59 is a vertical cross sectional view of left ventricle B of heart A having an apex D on which another alternate embodiment 470 of a locator device is shown disposed within chamber B. Locator device 470 includes an elongate catheter shaft 472 having a distal end 478. Extending from distal end 478 is a wire or elastic ribbon 476. Wire 476 is shown extending transversely from distal end 478 to radiopaque or echogenic markers 479. Additional wires or leads 474 extend proximally from markers 479 to a ring or hub 475 disposed outside of heart A. To advance catheter 470 into chamber B or withdraw it therefrom, hub 475 is pulled distally along shaft 472 to draw wires 474, markers 479 and wires 476 generally parallel to and adjacent shaft 472. In this position, catheter 470 can be advanced through or withdrawn from chamber B by way of a port or window used for less invasive procedures. Catheter 470 and markers 479 can be used to locate the entry/exit points similarly to the locators shown in FIGS. 4–12 and in particular, the marker 55 of FIG. 10.

Figure 60:
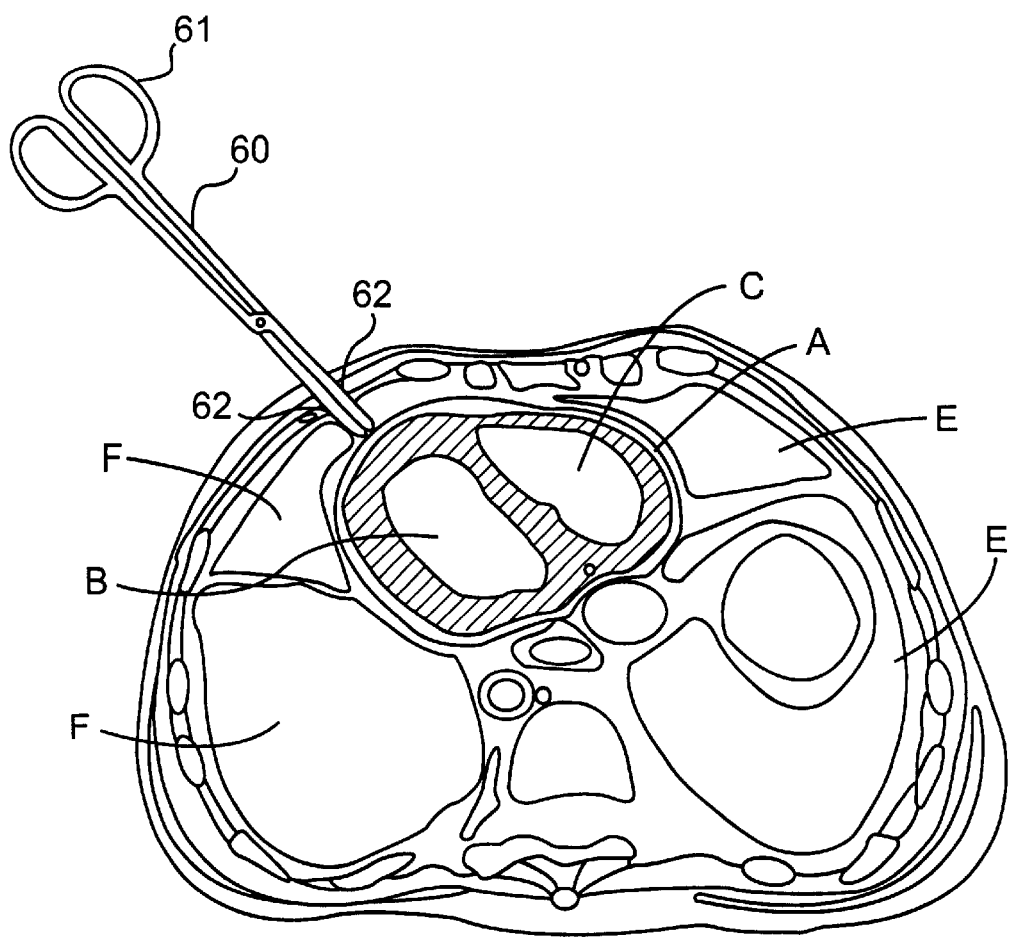
FIG. 60 is a cross section of a torso taken through the left and right ventricles including a locating clamp.
Figure 61:
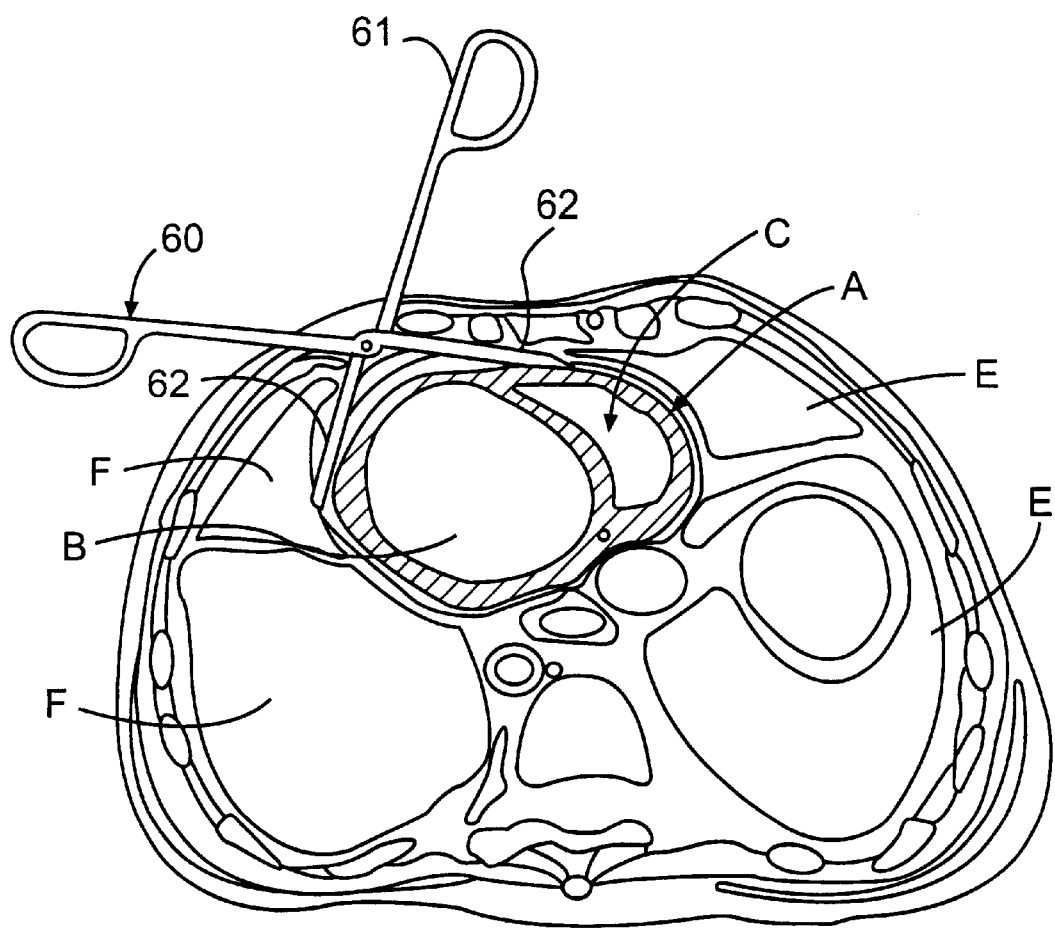
FIG. 61 is a view of the locating clamp of FIG. 60.
Figure 62:
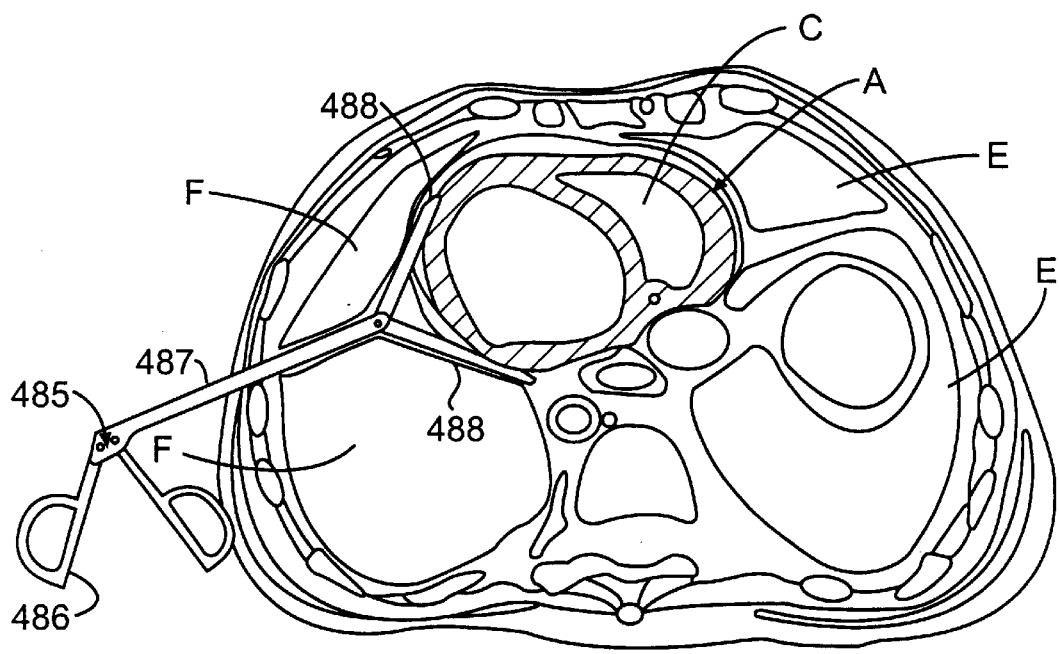
FIG. 62 is a view of an alternate embodiment of a marking clamp.

FIG. 60 is a transverse cross section of a human torso through heart A, left ventricle B and right ventricle C, right lung E and left lung F. Locator 60 of FIG. 11 is shown being advanced less invasively to heart A. FIG. 61 is a same human torso cross section as shown in FIG. 60, except that locator 60 has been brought into engagement with heart A as shown from a different perspective in FIG. 12. FIG. 62 is yet another view of the same torso cross section where a locator 485 having scissor-like handle 486 and arms 488 are coupled by an elongate linkage 487. As can be appreciated by those skilled in art, arms 488 can be drawn together or spread apart by an operating handle 486. The distal end of arms 488 should be echogenic or radiopaque such that they can be viewed by echo imaging or fluoroscopy similarly to end 62 of locator 60. Locator 485 is shown advanced to heart A through a lateral left approach. Locator 485 is preferably advanced through a port not shown of a type known to those skilled in the art. It can be appreciated that locator 485 can be used to locate a splint at a different location than locator 60.

Figure 63:
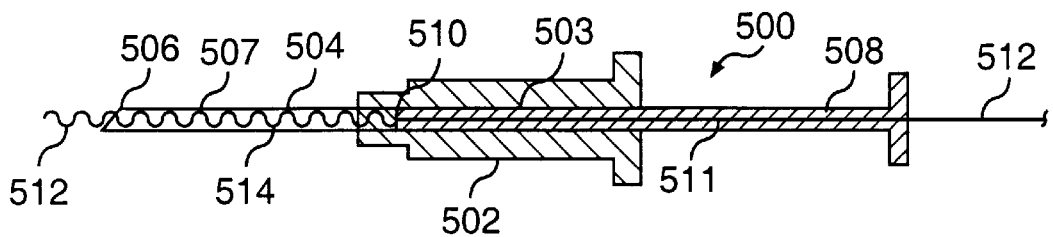
FIG. 63 is a cross sectional view of a thread pusher.

An alternate method of splint placement could advantageously use a thread pusher and snare. FIG. 63 is a view of a thread pusher 500. Thread pusher 500 includes a housing 502 defining a lumen 503 therethrough. Extending from lumen 503 is a shaft 504 having a sharpened distal tip 506. Shaft 504 defines a lumen 507 in fluid communication with lumen 503 of housing 502. Shown disposed within lumen 503 and advancable into lumen 507 is a plunger 508. Plunger 508 has a distal end 510. Plunger 508 defines an elongate lumen 511 extending the length of plunger 508. Disposed through lumens 503, 511 and 507 is a thread 512. Lumen 511 preferably has a diameter just slightly greater than the diameter of thread 512. Lumen 507, however, has a diameter great enough to coil a substantial length of thread 512 therein. The necessary length of thread 512 can be appreciated in view of the discussion which follows regarding the use of thread pusher 500.

Figure 64:
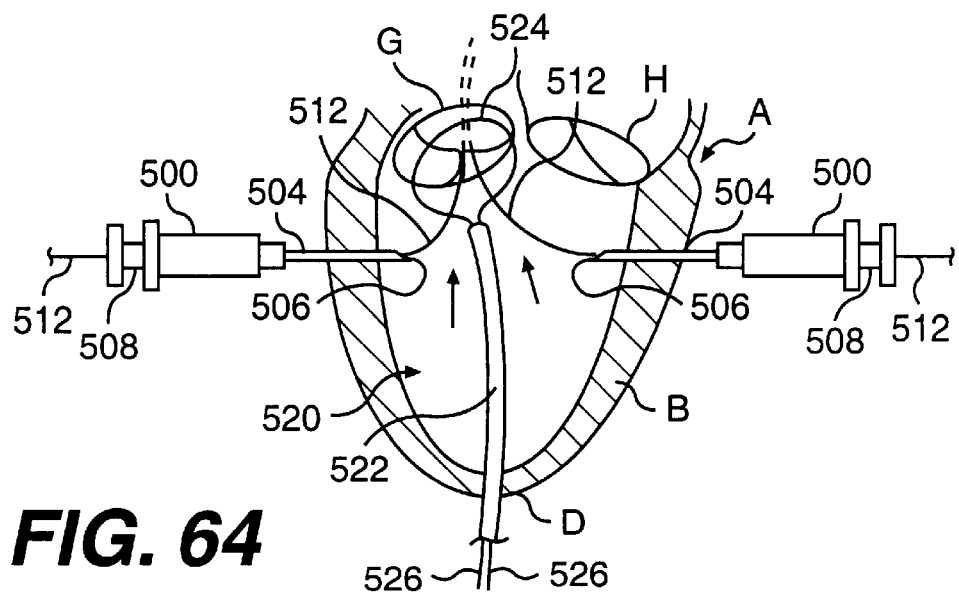
FIG. 64 is a cross sectional view of the left ventricle including two thread pushers and a snare.

FIG. 64 is a generally vertical cross sectional view of left ventricle B of heart A having apex D, aortic valve G and mitral valve H. Disposed within chamber B is a catheter 520 having an elongate catheter shaft 522 extending through apex D of heart A to proximate aortic valve G. A wire or line 526 extends through an elongate lumen through shaft 522, loops to form a snare 524 at the distal end of shaft 522 and returns back through the lumen. As shown in FIG. 64, snare 524 is disposed generally around or preferably through the orifice of aortic valve G. Two thread pushers have been advanced from opposite sides of heart A such that distal tips 506 of shafts 504 are disposed within chamber B. Plunger 508 of thread pusher 500 has been advanced to release previously coiled portion 514 of thread 512 into chamber B. As shown by the arrows, blood flow leaving chamber B exits through aortic valve G. As shown in FIG. 64, this blood flow has carried threads 512 through snare 524 and aortic valve G.

Figure 65:
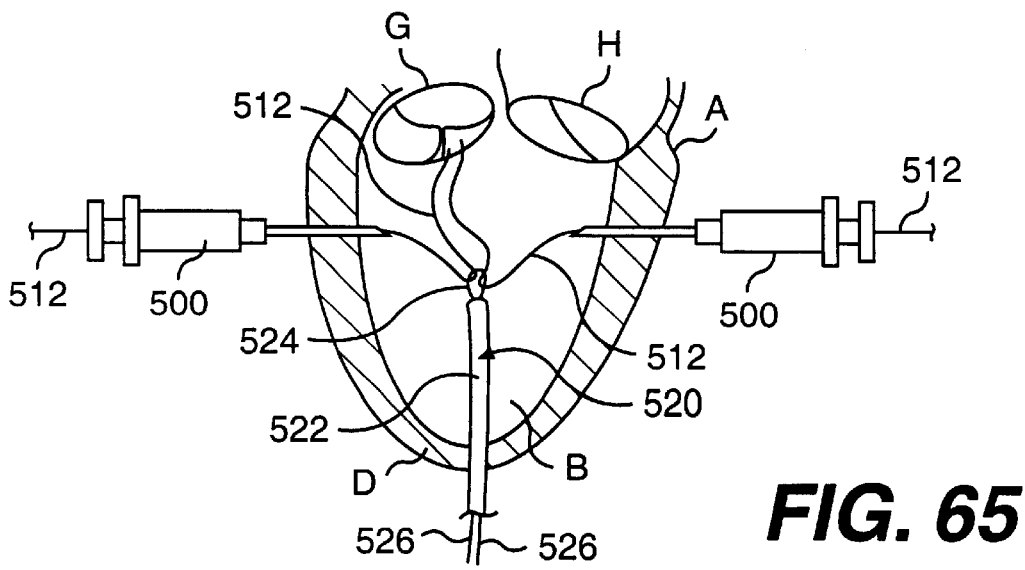
FIG. 65 is a subsequent view of the devices of FIG. 64.
Figure 66:
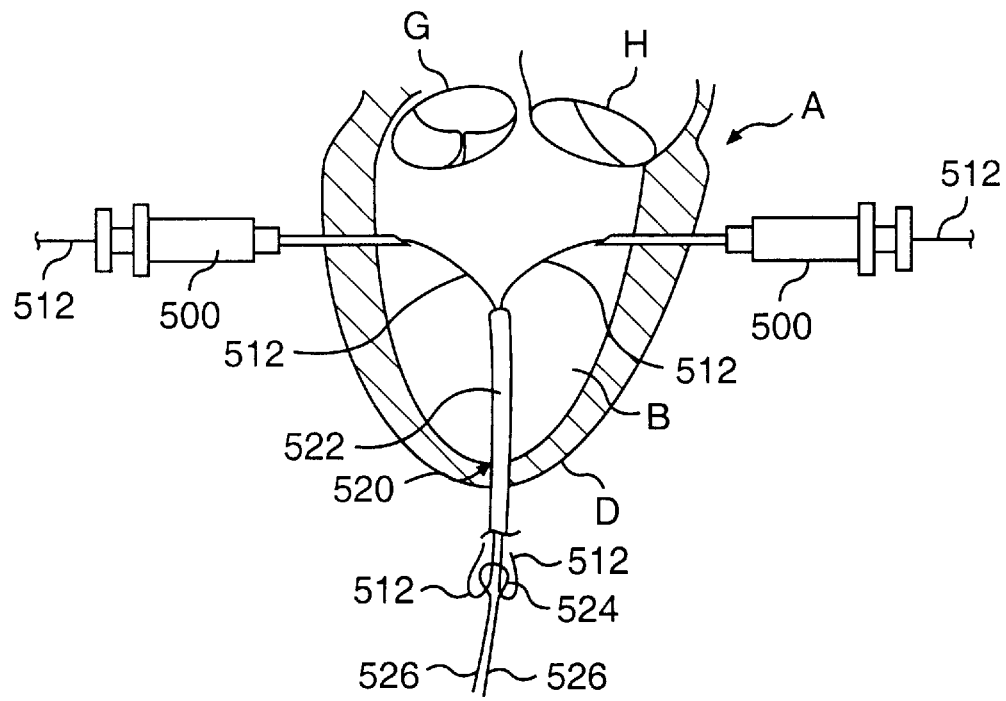
FIG. 66 is a subsequent view of the device of FIG. 65.

FIG. 65 shows the same cross sectional view of left ventricle B as FIG. 64, except that snare 524 has been partially retracted by pulling line 526 proximally. Catheter 520 has also been partially withdrawn in a proximal direction from chamber B. FIG. 66 is yet another view of the cross section of left ventricle B as shown in FIG. 64, except that snare 524 has been withdrawn proximally from catheter 522 such that an end of each thread 512 is disposed proximally of shaft 522.

Figure 67:
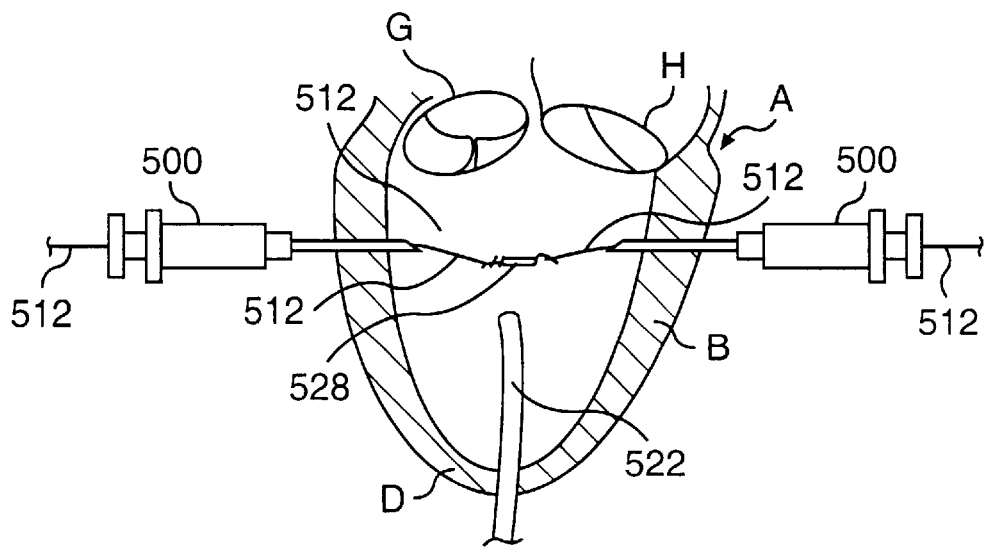
FIG. 67 is a subsequent view of the device of FIG. 66.

FIG. 67 is yet another view of the cross section of left ventricle B shown in FIG. 64, except that threads 512 have been joined and extend across left ventricle B. To achieve the configuration of FIG. 67, the ends of threads 512 disposed proximally of shaft 522 in FIG. 66 are tied together. Then the opposite ends of thread 522 are pulled proximally relative to respective thread pushers 500 until threads 512 are withdrawn from catheter shaft 522 and extend across chamber B. Thread pushers 500 can be withdrawn proximally from threads 512. Joined threads 512 can be used as a tension member to assemble a transventricular splint. Preferably, however, after thread pushers 500 are removed from threads 512, a tension member is connected to one of the free ends of thread 512 by, for example, tying the end of thread 512 to a loop formed in an end of a tension member. Then the remaining free end of thread 512 can be withdrawn proximally until both threads 512 are pulled from chamber B and the tension member extends across the chamber. Once the tension member extends across the chamber, the remainder of the splint can be assembled in a manner similar to that contemplated for the tension members placed in accordance with FIGS. 38–43.

It can be appreciated that the method of placing a tension member described with respect to FIG. 64 can advantageously be performed by an open chest or less invasive route. The method described, however, lends itself particularly well to a less invasive approach where oppositely disposed lateral ports are used to manipulate string pushers 500 and an anterior port is used to access apex D by catheter 520. As an alternative to the apical approach, snare 524 could be placed from an aortic or mitral valve approach. If the approach is by way of the aortic valve, the snare may be advanced thereto by way of the aorta from a carotid or femoral artery access point. The mitral valve approach could be made by way of a port or window. The mitral valve port may be particularly desirable if mitral valve repair or replacement is preformed in conjunction with splint implantation.

Figure 68:
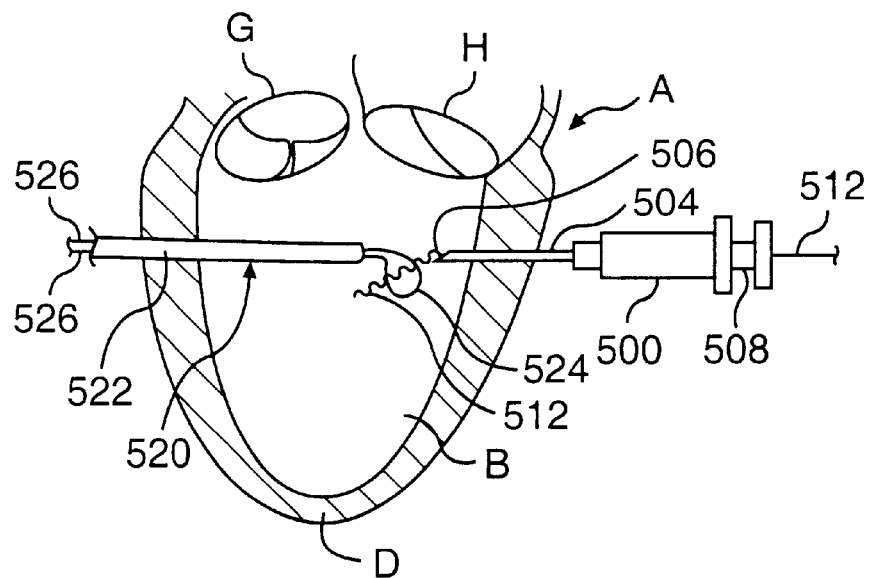
FIG. 68 is a cross sectional view of a left ventricle including a snare and thread pusher.
Figure 69:
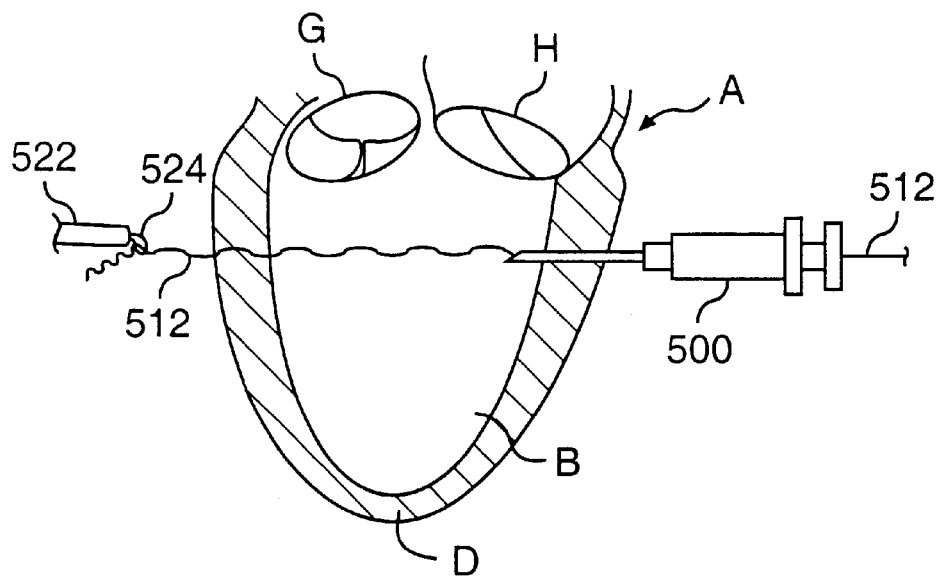
FIG. 69 is a subsequent view of the device of FIG. 68.

FIGS. 68 and 69 illustrate yet another method of placing a tension member across ventricle B using snare 524, and a thread pusher 500. Unlike the method described with respect to FIGS. 64–67, the lateral approaches are preferably used without requiring access to apex D. Catheter 520 is advanced from one side of chamber B and placed generally around distal tip 506 of shaft 504 of thread pusher 500 which is advanced into chamber B from the opposite side. Plunger 508 is depressed to push the coiled portion of thread 512 into chamber B. Thread 512 drifts toward aortic valve G and through snare 524 under the influence of blood flow.

As shown in FIG. 69, snare 524 is tightened around thread 512 and withdrawn from chamber B. It can be appreciated that catheter 520 and thread pusher 512 can be removed from thread 512 and a splint assembled in the manner described above with respect to the tension member placed in accordance with the method described in FIGS. 64–67. It can also be appreciated that this method can advantageously be applied to implant a splint either by an open chest or less invasively using two oppositely disposed lateral ports.

Figure 70:
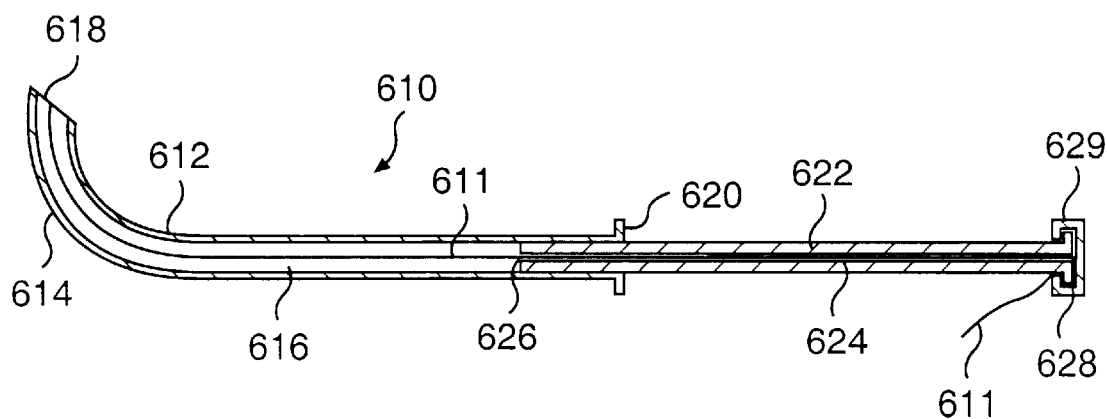
FIG. 70 is a cross sectional view of an alternate embodiment of a thread pusher.

FIG. 70 is a longitudinal cross sectional view of an alternate embodiment of a thread pusher 610. Thread pusher 610 includes a thread insertion shaft 612 having a lumen 612 extending therethrough. Shaft 612 can have a curved distal end 614 which preferably includes a sharpened portion 618 for insertion through the heart wall into the left ventricle. A handle 620 is preferably disposed at the proximal end of shaft 612. A plunger 622 is preferably disposed within shaft lumen 616. Plunger 622 includes a distal end 626 and a proximal end preferably including a handle 628. A lumen 624 extends through plunger 622. A thread or filament 611 is shown disposed within shaft lumen 616 and plunger lumen 624. Unlike thread pusher 500 of FIG. 63, the length of shaft 612 is preferably long enough that the portion of thread 611 to be advanced into the left ventricle can be disposed within lumen 616 without being coiled.

In use, distal tip 618 of thread pusher 610 is disposed in left ventricle B in a manner similar to that of tip 506 of thread pusher 500. Plunger 622 is then advanced into shaft lumen 616 to advance thread 611 into the left ventricle.

Thread 612 is preferably lightly friction within lumen 624 or held within lumen 624 by the user or holding cap 629.

Figure 71:
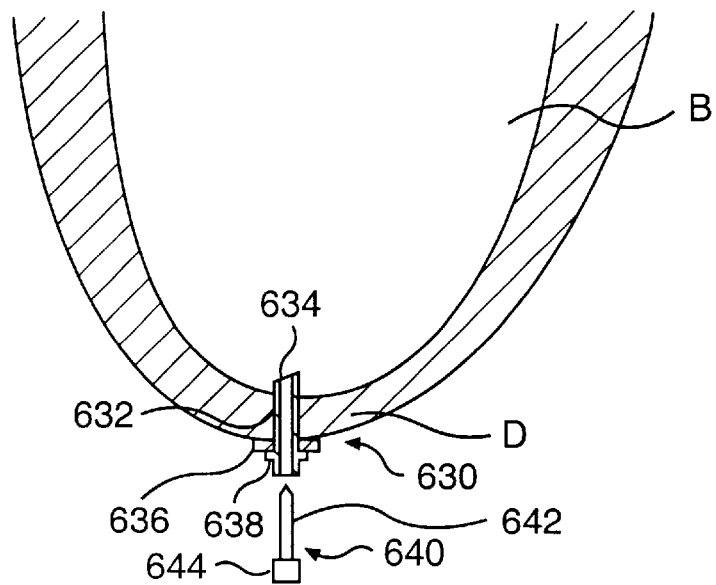
FIG. 71 is a cross sectional view of a snare insertion tube.

FIG. 71 is a generally vertical cross section of left ventricle B showing a longitudinal cross sectional of a snare insertion tube 630 disposed through apex D. Insertion tube 630 preferably includes an elongate shaft 632 having an elongate lumen extending therethrough. An annular flange 638 is preferably disposed at the proximal end of shaft 632. Disposed in engagement with, and distally of flange 638 is an annular felt pad 636. A stylet 640 having an elongate shaft 642 and a hub 644 can be inserted within the lumen of shaft 632.

In use, snare insertion tube 630 can be used to provide a stable access through apex D for catheter 520 when performing the procedure shown in FIGS. 64–67 above. Insertion tube 630 can be advanced into apex D as shown. As insertion tube 630 is advanced into apex D, stylet 640 is preferably disposed therein to limit bleeding through the lumen through shaft 632. Felt pad 636 is preferably sutured to apex D to limit bleeding around shaft 632 and stabilize insertion tube 630 on apex D. Stylet 640 is then removed and then catheter 520 can be advanced through insertion tube 630 to perform the splint implantation.

Up to this point, it has been assumed that access was obtained or obtainable to each end of the tension member for placement of an anchor or anchor pad thereon. Access to each end of the tension member placed across the left ventricle is generally obtainable by open chest access or lateral, anterior or posterior ports. It is contemplated, however, that under some circumstances, however, it may be difficult or undesirable to obtain access to one or both ends of the tension member. Under such circumstances, it may be desirable to be able to deliver an anchor or anchor pad to a wall of the ventricle to which direct access by open chest or port has not been obtained. In such an instance, it may be desirable to deliver the anchor or anchor pad from inside the heart to the outside.

Figure 72:
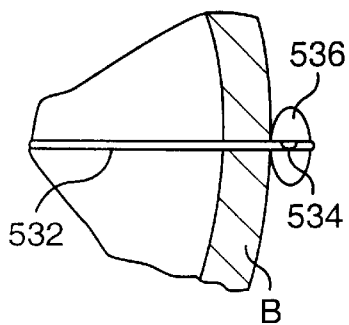
FIG. 72 is yet another alternate anchor pad embodiment.

FIG. 72 is a cross sectional view of a portion of left ventricle B including a distal portion of a tension member 532 having a balloon anchor 536 disposed at its distal end and outside of chamber B of heart A. Tension member 532 is preferably a tubular member such as a hypotube sealed at its distal end except for an orifice 534 disposed within balloon 536. The distal end of tension member 532 including balloon 536 can be advantageously and preferably advanced to the position shown by using any of the methods and devices disclosed above which advance the tension member from inside the heart to outside, for example, the method and device described above with respect to FIGS. 38–40. Once the distal end of tension member 532 is advanced to the position shown, balloon 536 can be inflated from a collapsed position to the expanded position shown. Balloon 536 is preferably expanded using quick cure polymer such as cyanoacrylate or mixed two-part epoxy or other biocompatible substance which will allow balloon 536 to remain in an expanded position chronically. Saline is preferably used as inflation fluid if the balloon is inflated acutely.

Figure 73:
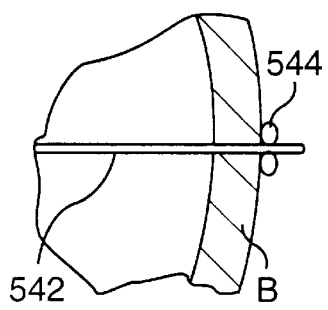
FIG. 73 is yet another alternate anchor pad embodiment.

FIG. 73 is a similar view to that of FIG. 72 except a tension member 542 having a pad 544 is shown disposed in left ventricle B. Pad 544 is preferably a coiled pad which can be delivered as described above with respect to the balloon of FIG. 72, except that it may be preferable to advance pad 544 through the heart wall through a tube. Coil 544 can be compressed within the tube and upon emerging from the tube and the heart, expand. Coil 544 could also could be formed from a shape memory alloy and be preset to expand at approximately body temperature.

Figure 74:
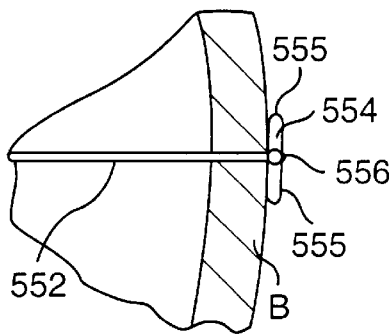
FIG. 74 is yet another alternate anchor pad embodiment.

FIG. 74 is yet another example of an anchor pad deployable from inside the heart to outside the heart. Pad 554 is shown disposed at the end of the tension member 552. Pad 554 includes two arms pivotally connected to tension member 522 by hinge 556. Hinge 556 preferably allows arms 555 to rotate from a first position parallel and adjacent to tension member 552, to a second position approximately perpendicular to tension member 552 as shown. To deploy pad 554, pad 554 is advanced from the heart through the heart wall with arms 555 disposed in the first position until the arms are completely advanced to the outside of the wall. Then tension member 552 is drawn in the opposite direction such that the ends of arms 555 engage the heart wall and pivot into the second position as tension member 552 continues to be pulled.

Figure 75:
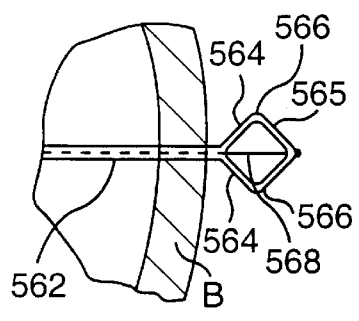
FIG. 75 is yet another alternate anchor pad embodiment.

FIG. 75 is yet another embodiment of an anchor pad 565 which can be placed from inside the heart to outside by the methods applicable to the device of FIG. 72. Pad 565 includes two arms 564 hingably connected to tension member 562. Arms 564 include a hinge 566. Pad 565 can be advanced through the heart wall while arms 564 are parallel and adjacent to each other. Once arms 564 have been advanced to the outside of the heart, a wire or line 568 connected to the distal end of arms 566 and extending proximally through tension member 562 can be pulled proximately to shorten the distance between the ends of arms 564 and bend arms 564 outward at hinges 566.

Figure 76:
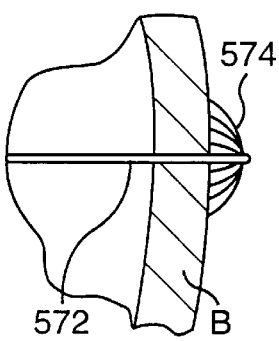
FIG. 76 is yet another alternate anchor pad embodiment.

FIG. 76 is yet another embodiment of an anchor pad 574 disposed on a distal end of tension member 572. Pad 574 has an umbrella-like shape, the top of the umbrella being disposed away from the heart wall and the broad base of the umbrella being disposed toward the heart wall. Pad 574 is advanced through the heart wall in a collapsed position. Pad 574 can be biased to expand upon passing through the heart wall or can be expanded in a manner similar to pad 554 of FIG. 74.

Figure 77:
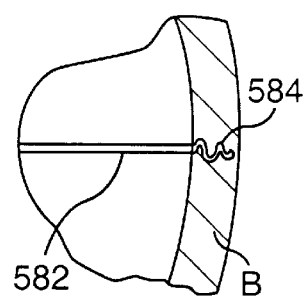
FIG. 77 is a view of an anchor screw.

FIG. 77 is a view of anchor or anchor screw 584 disposed at the distal end of a tension member 582. Screw 584 unlike the anchor pads of FIGS. 72–76 does not have to pass through the heart wall to secure tension member 582 in place. Rather, anchor 584 has a corkscrew or auger shape. Screw 584 is anchored to the myocardium by rotating tension member 582 while advancing anchor 584 into the myocardium.

Figure 78:
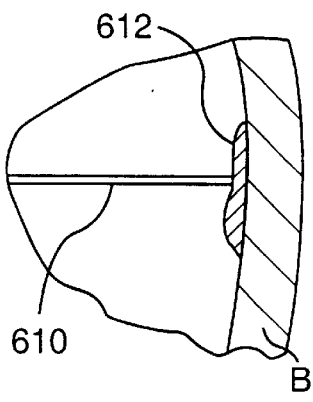
FIG. 78 is a view of yet another alternate anchor pad embodiment.

FIG. 78 is a view of yet another embodiment of anchor pad 612 disposed on an end of a tension member 610. Pad 612 is preferably a fabric such as dacron or PTFE. A fast acting adhesive can secure pad 612 to the heart wall as shown. The adhesive can be, for example, cyanoacrylate. The adhesive can be triggered by reaction with the heart wall tissue, be pressure sensor, be activated by an accelerator or energy source.

Figure 79:
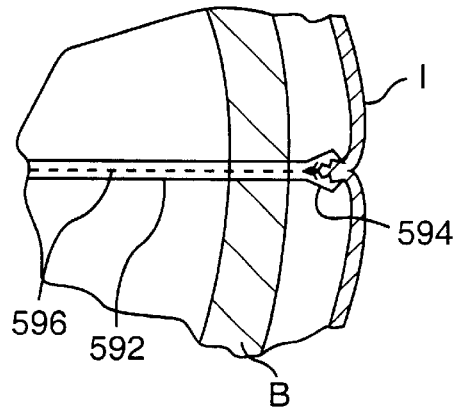
FIG. 79 is a view of an anchor epicardial jaw embodiment.

FIG. 79 is a cross section of a portion of left ventricle B similar to that shown in FIGS. 72–78 except that the epicardium I is shown. The device of FIG. 79 includes a tubular tension member 592 including an anchor or an epicardial jaw anchor 594 disposed at its distal end. Jaw anchor 594 is connected to a wire or line disposed through the lumen of tension member 592. The jaw anchor 594 is biased to open when unrestrained by the distal end of tension member 592. If wire 596 is pulled proximally, jaws 594 will engage the distal end of tension member 592 tending to close anchor jaws 594, by a mechanism similar to that of the device of FIG. 51, except that anchor jaws 594 are not intended to cut but rather grip.

It should be noted that not only can the anchors and anchor pads of FIGS. 72–79 be advantageously employed when one of the ends of the tension member extending outside the heart will not be directly accessible to deploy a pad thereon, but also where neither end of the tension member will be accessible to place a pad thereon. In such an instance, two tension members having anchors or anchor pads as shown in FIGS. 72–79 can be placed through an apical approach similarly to how guide members 270 and 271 were placed in FIG. 41. Once the anchors or anchor pads are deployed, however, the two tension members are preferably connected to form effectively a single tension member.

Figure 80:
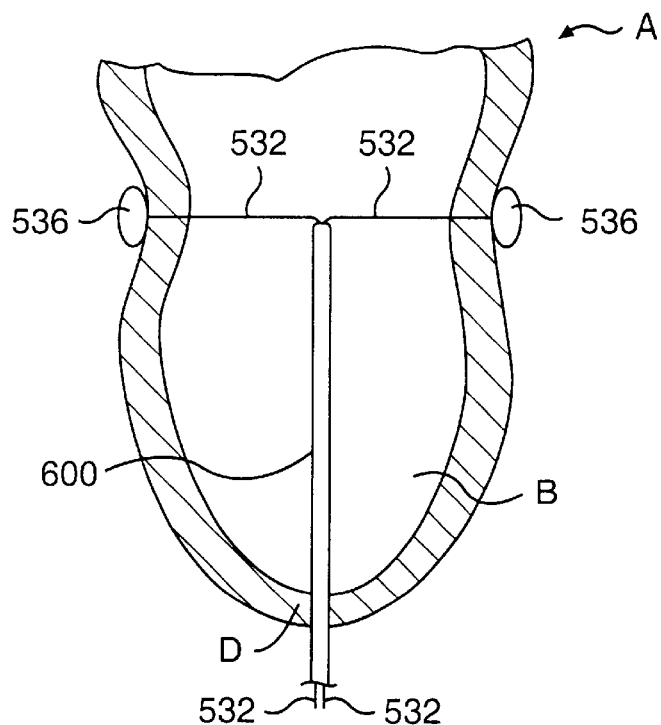
FIG. 80 is vertical cross sectional view of the heart including anchors deployed from within the heart.

FIG. 80 is a vertical cross sectional view of the left ventricle B of heart A having apex D. For purposes of illustrating the deployment of two tension members and anchors or anchor pads without direct access to the distal ends of the tension members, outside the heart, for placement of the pads thereon, two tension members 532 having balloons 536 disposed at their distal ends are shown placed on left ventricle B. It can be appreciated that tension members 532 and balloons 536 can be placed on the heart in a manner similar to guide members 270 and 271 of FIG. 41. Then catheter tube 600 can be advanced over tension members 532. Tension members 532 can then be drawn proximally to reduce the distance between pads 536 to create either a full cycle or restrictive splint.

Figure 81:
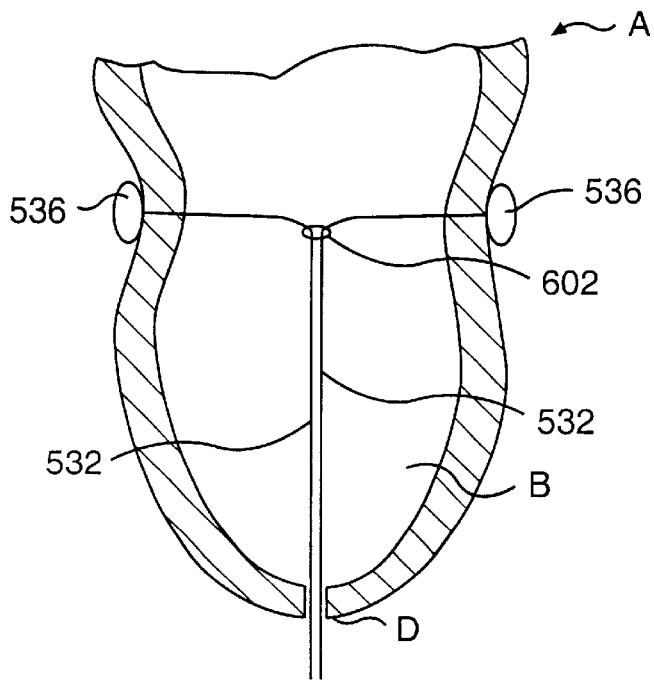
FIG. 81 is a vertical cross sectional view of a heart showing tension members deployed from within the heart connected within the heart.

FIG. 81 is the same cross sectional view as FIG. 80 except that catheter 600 has been removed from chamber B and a tension member fastener 602 has been placed to interconnect tension members 532. Fastener 602 can be formed from a disc similar to pad 382 of FIG. 49, but form with an additional tension member receiving aperture 390. To place fastener 602, fastener 602 can be advanced through catheter 600 over tension members 532 by an elongate spreader. The spreader can be removed and fastener 602 clamped to tension members 532. Then the catheter 600 can be removed to obtain the configuration shown in FIG. 80. It should also be noted that prior to removing catheter 600, tension member cutter 420 of FIG. 1 could be advanced over the tension members to remove the excess length shown extending through apex D.

It can be appreciated that the method of FIGS. 80 and 81 can be performed open chest or less invasively. When performed less invasively, an anterior access port is preferably used. In addition to performing the methods of FIGS. 80 and 81 by way of apex D, access could be gained to left ventricle B by way of the aortic valve or mitral valve as described above.

The effective length of the tension member between anchor pads 536 can be determined by knowing the overall length of each tension member and the length of catheter 600. The effective length of the tension member will be the sum of the lengths of the tension members less two times the length of catheter 600 and less the length of each tension member extending proximally from catheter 600 when the distal end of catheter 600 abuts fastener 602. If pads 536 were made from echogenic or radiopaque material the effective length of the tension could be estimated by echo imaging or fluoroscopic techniques. It can also be appreciated that the length of the tension member can be measured directly be advancing a measuring device into chamber B.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is, of course, defined in the language in which the appended claims are expressed.

What is claimed is:

1. An alignment system for aligning an elongate member during insertion into a heart chamber, comprising:
    an elongate member; and an alignment device comprising:
        a first arm and a second arm adapted to move relative to each other and extend around at least a portion of a wall of a heart chamber;
        a first positioning member disposed on an end of said first arm; and
        a second positioning member disposed on an end of said second arm to substantially oppose said first positioning member,
    wherein the first and second positioning members respectively define first and second apertures configured to receive the elongate member so as to assist in aligning the elongate member with respect to a heart chamber during insertion of the elongate member into the heart chamber.

2. The system of claim 1, wherein at least one of the first and second positioning members includes a stabilization mechanism for stabilizing the positioning member with respect to the heart wall.

3. The system of claim 2, wherein the stabilization mechanism comprises a vacuum aperture for fluid communication with a vacuum source.

4. The system of claim 3, wherein the at least one of the first and second positioning members are stabilized with respect to said heart wall when the vacuum aperture is connected to the vacuum source.

5. The system of claim 2, wherein the stabilization mechanism comprises a friction surface for stabilizing said positioning member with respect to said heart wall.

6. The system of claim 1, wherein the first positioning member includes a stopping mechanism adapted to stop advancement of the elongate member.

7. The system of claim 1, further comprising first and second handles respectively attached to said first and second arms.

8. The device of 7, wherein said first handle and said first arm are pivotally connected to said second handle and said second arm.

9. The device of claim 8, wherein at least one of said first positioning member and said second positioning member is rotatably connected to said respective first arm and second arm.

10. The device of claim 9, wherein a band extends between said positioning members.

11. The device of claim 1, wherein the first and second arm include curved portions.

12. The device of claim 1, wherein the first arm is configured to be connected to a guide tube.

13. The device of claim 1, wherein at least one of the first positioning member and the second positioning member defines a suction chamber.

14. The device of claim 1, wherein the first positioning member and the second positioning member are heart-engaging members.

15. An alignment device for aligning an elongate member during insertion into a heart chamber, comprising:
    a first arm and a second arm adapted to move relative to each other and extend around at least a portion of a wall of a heart chamber;
    a first positioning member disposed on an end of said first arm;

a second positioning member disposed on an end of said second arm to substantially oppose said first positioning member;

first and second handles respectively attached to said first and second arms; and a spring adapted to bias said handles away from each other and said first and second alignment arms toward each other, wherein the first and second positioning members respectively define first and second apertures.

16. An alignment device comprising:

a first arm supporting a first tissue-engaging member, the first tissue-engaging member having a first tissue-contacting surface and defining at least one suction chamber;

a second arm supporting a second tissue-engaging member, the second tissue-engaging member having a second tissue-contacting surface and defining at least one suction chamber;

a stop associated with the second tissue-engaging member, the stop being configured to stop advancement of a member past the stop as the member is being advanced from the first tissue-engaging member to the second tissue-engaging member; and a handle assembly connected to the first and second arms.

17. The alignment device of claim 16, wherein the first and second tissue engaging members are heart-engaging members.

18. The alignment device of claim 16, wherein the first and second arms include curved portions.

19. The alignment device of claim 16, further comprising a guide tube connected to the first arm.

20. The alignment device of claim 19, wherein an outlet of the guide tube is aligned with a center of the first tissue-engaging member.

21. The alignment device of claim 16, wherein the at least one suction chamber of each of the first and second arms is configured to be connected to a vacuum source.

22. The alignment device of claim 16, wherein the handle assembly includes a first handle portion supporting the first arm and a second handle portion supporting the second arm.

* * * * *

UNITED STATES PATENT AND TRADEMARK OFFICE
CERTIFICATE OF CORRECTION

PATENT NO. : 6,746,471 B2
DATED : June 8, 2004
INVENTOR(S) : Todd J. Mortier et al.

It is certified that error appears in the above-identified patent and that said Letters Patent is hereby corrected as shown below:

<u>Title page,</u>
Item [57], ABSTRACT,
Line 3, replace "hearts" with -- heart --;
Line 6, replace "tensions" with -- tension --;

<u>Column 28,</u>
Line 42, replace "of 7" with -- of claim 7, --.

Signed and Sealed this

Third Day of August, 2004

JON W. DUDAS
*Acting Director of the United States Patent and Trademark Office*